United States Patent
Kim et al.

(10) Patent No.: US 12,117,455 B2
(45) Date of Patent: Oct. 15, 2024

(54) EARLY DETECTION MARKER FOR DEGENERATIVE OSTEOARTHRITIS WITH TRIM24-RIP3 AXIS

(71) Applicant: AJOU UNIVERSITY INDUSTRY-ACADEMIC COOPERATION FOUNDATION, Suwon-si (KR)

(72) Inventors: You-Sun Kim, Suwon-si (KR); Siyoung Yang, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 346 days.

(21) Appl. No.: 17/475,753

(22) Filed: Sep. 15, 2021

(65) Prior Publication Data

US 2022/0091136 A1   Mar. 24, 2022

(30) Foreign Application Priority Data

Sep. 16, 2020   (KR) .................. 10-2020-0119158

(51) Int. Cl.
*C12Q 1/6883*   (2018.01)
*G01N 33/68*   (2006.01)

(52) U.S. Cl.
CPC ..... *G01N 33/6893* (2013.01); *G01N 2500/00* (2013.01); *G01N 2800/105* (2013.01)

(58) Field of Classification Search
None
See application file for complete search history.

(56) References Cited

U.S. PATENT DOCUMENTS

2019/0195891 A1 * 6/2019 Wallach .................. C07B 63/04

FOREIGN PATENT DOCUMENTS

| CN | 108203732 A * | 6/2018 | ............. A61K 45/00 |
|---|---|---|---|
| JP | 2016-514693 A | 5/2016 | |
| JP | 2018191568 A * | 12/2018 | |
| KR | 10-1858346 B1 | 5/2018 | |
| WO | 2005/105830 A1 | 11/2005 | |
| WO | WO-2013033627 A2 * | 3/2013 | ........... C12Q 1/6883 |
| WO | WO-2017208001 A1 * | 12/2017 | ......... G01N 33/6893 |

OTHER PUBLICATIONS

Ying et al. Mixed Lineage Kinase Domain-like Protein MLKL Breaks Down Myelin following Nerve Injury. Molecular Cell. 72 (3): 457-468; Published: Nov. 1, 2018 (Year: 2018).*
Wang et al. FKBP12 mediates necroptosis by initiating RIPK1-RIPK3-MLKL signal transduction in response to TNF receptor 1 ligation. Journal of Cell Science. 132 (10): jcs227777; Published: May 20, 2019 (Year: 2019).*
Zhang et al. Catalytically inactive RIP1 and RIP3 deficiency protect against acute ischemic stroke by inhibiting necroptosis and neuroinflammation. Cell Death & Disease. 11: 565; Published: Jul. 23, 2020 (Year: 2020).*
Jeon et al. TRIM24-RIP3 axis perturbation accelerates osteoarthritis pathogenesis. Annuals of Rheumatic Diseases. 79: 1635-1643 ; Published: Sep. 7, 2020 (Year: 2020).*
Lv et al. TRIM24 is an oncogenic transcriptional co-activator of STAT3 in glioblastoma. Nature Communications. 8: 1454; Published : Nov. 13, 2017 (Year: 2017).*
Yu et al. BMP8A promotes survival and drug resistance via Nrf2/TRIM24 signaling pathway in clear cell renal cell carcinoma. Cancer Science. 111: 1555-1566; Published: May 2020 (Year: 2020).*
Guan et al. Epigenetic silencing of miR-137 induces resistance to bicalutamide by targeting TRIM24 in prostate cancer cells. American Journal of Translational Research. 11 (5): 3226-3237; Published: May 30, 2019 (Year: 2019).*
Yang et al. RIP3 b and RIP3 c, two novel splice variants of receptor-interacting protein 3 (RIP3), downregulate RIP3-induced apoptosis. Biochemical and Biophysical Research Communications. 332: 181-187: Published: Apr. 28, 2005 (Year: 2005).*
E. M. Schott. The Pathobiology of Osteoarthritis in Obesity: The Role of Synovial Inflammation, Joint Insulin Resistance, and Dysbiosis of the Gut Microbiome. University of Rochester Thesis; Available: May 14, 2019 (Year: 2019).*
Stolberg-Stolberg et al .Cartilage Trauma Induces Necroptotic Chondrocyte Death and Expulsion of Cellular Contents. International Journal of Molecular Sciences. 21: 4204; Published: Jun. 12, 2020 (Year: 2020).*
Armaka et al. The p55TNFR-IKK2-Ripk3 axis orchestrates arthritis by regulating death and inflammatory pathways in synovial fibroblasts. Nature Communications. 9: 618; Published: Feb. 12, 2018 (Year: 2018).*
Riegger and Brenner. Evidence of necroptosis in osteoarthritic disease: investigation of blunt mechanical impact as possible trigger in regulated necrosis. Cell Death & Disease. 10: 683; Published: Sep. 17, 2019 (Year: 2019).*
Riegger et al. Crucial role of the terminal complement complex in chondrocyte death and hypertrophy after cartilage trauma. Osteoarthritis and Cartilage. 28: 685-697: Published: Jun. 22, 2020 (Year: 2020).*
Sun et al. Biological Effects of Phosphocitrate on Osteoarthritic Articular Chondrocytes. The Open Rheumatology Journal. 11: 62-74 ; Published: Apr. 8, 2017 (Year: 2017).*
Zhao et al. Overexpression of FES might inhibit cell proliferation, migration, and invasion of osteosarcoma cells. Cancer Cell International. 20: 102: Published: Mar. 20, 2020 (Year: 2020).*

(Continued)

*Primary Examiner* — Juliet C Switzer
*Assistant Examiner* — Katherine Ann Holtzman
(74) *Attorney, Agent, or Firm* — Sughrue Mion, PLLC

(57) ABSTRACT

Disclosed is the novel use of TRIM24 and RIP3 as biomarkers for diagnosing osteoarthritis, in which it is first identified that TRIM24 and RIP3 can be used as biomarkers for diagnosing osteoarthritis by confirming the tendency of TRIM24 expression to decrease and RIP3 expression to increase at the onset of osteoarthritis. These two proteins are useful in confirming the change in the expression level from the onset of osteoarthritis, thus enabling early diagnosis of osteoarthritis and effectively blocking the progression of osteoarthritis at an early stage.

5 Claims, 64 Drawing Sheets

Specification includes a Sequence Listing.

(56) References Cited

OTHER PUBLICATIONS

Zhou et al. Emodin induced necroptosis in the glioma cell line U251 via the TNF-α/RIP1/RIP3 pathway. Investigational New Drugs. 38: 50-59; Published Online: Mar. 28, 2019 (Year: 2019).*

Jana Riegger et al., "Evidence of necroptosis in osteoarthritic disease: investigation of blunt mechanical impact as possible trigger in regulated necrosis", Cell Death and Disease, 2019, vol. 10, No. 683, pp. 1-12 (12 pages total).

Jean-Pierre Pelletier et al., "Osteoarthritis, an Inflammatory Disease Potential Implication for the Selection of New Therapeutic Targets", Arthritis & Rheumatism, vol. 44, No. 6, Jun. 2001, pp. 1237-1247 (11 pages total).

J-H Ryu et al., "Hypoxia-inducible factor-2α regulates Fas-mediated chondrocyte apoptosis during osteoarthritic cartilage destruction", Cell Death and Differentiation, 2012, vol. 19, pp. 440-450 (11 pages total).

C. M. Thomas et al., "Chondrocyte death by apoptosis is associated with cartilage matrix degradation", OsteoArthritis and Cartilage, 2007, vol. 15, pp. 27-34 (8 pages total).

Kate E. Lawlor et al., "RIPK3 promotes cell death and NLRP3 inflammasome activation in the absence of MLKL", Nature Communications, Feb. 18, 2015, vol. 6, No. 6282, pp. 1-19 (19 pages total).

Armaka et al., "The p55TNFR-IKK2-Ripk3 axis orchestrates arthritis by regulating death and inflammatory pathways in synovial fibroblasts", Nature Communications, 2018, vol. 9, No. 618, pp. 1-12 (12 pages total).

Han-Hee Park et al., "HS-1371, a novel kinase inhibitor of RIP3-mediated necroptosis", Experimental & Molecular Medicine, 2018, vol. 50, No. 125, pp. 1-15 (15 pages total).

* cited by examiner

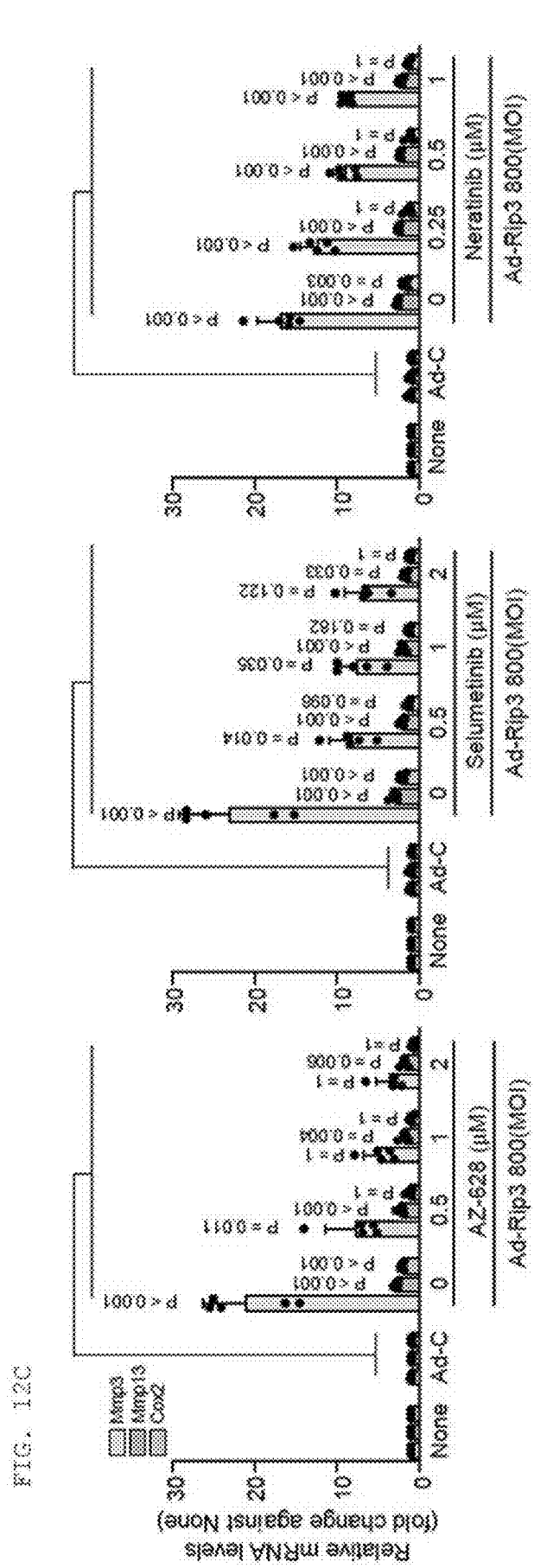

FIG. 13A

| Compound | PubChem CID | Molecular Formula | Binding Affinity, $\Delta G$ (kcal/mol) |
|---|---|---|---|
| Dabrafenib | 44462760 | $C_{23}H_{20}F_3N_5O_2S_2$ | -8.6 |
| Erk-inhibitor | 135523966 | $C_{20}H_{17}Cl_2FN_4O_2$ | -8.4 |
| AZ-628 | 11676786 | $C_{27}H_{25}N_5O_2$ | -8.4 |
| Geldanamycin | 5288382 | $C_{29}H_{40}N_2O_9$ | -7.9 |
| Trametinib | 11707110 | $C_{26}H_{23}FIN_5O_4$ | -7.8 |
| Neratinib | 9915743 | $C_{30}H_{29}ClN_6O_3$ | -7.6 |
| HS-1371 | 134817449 | $C_{24}H_{34}N_4O$ | -7.6 |
| PD98059 | 4713 | $C_{16}H_{13}NO_3$ | -7.1 |
| PD0325901 | 9826528 | $C_{16}H_{14}F_3IN_2O_4$ | -7.0 |
| GSK872 | 54674134 | $C_{19}H_{17}N_5O_2S_2$ | -6.6 |
| AZD8330 | 16666708 | $C_{18}H_{17}FIN_3O_4$ | -6.4 |
| AS605240 | 5289247 | $C_{13}H_9N_3O_2S$ | -6.3 |
| PD184352 | 6918454 | $C_{17}H_{14}ClF_2IN_2O_2$ | -5.9 |
| Selumetinib | 10127622 | $C_{17}H_{15}BrClFN_4O_3$ | -5.7 |

EARLY DETECTION MARKER FOR DEGENERATIVE OSTEOARTHRITIS WITH TRIM24-RIP3 AXIS

CROSS REFERENCE TO RELATED APPLICATIONS

This application claims priority based on Korean Patent Application No. 10-2020-0119158 filed Sep. 16, 2020 in the Korea Intellectual Property Office, of which content is incorporated herein by reference in its entirety.

INCORPORATION BY REFERENCE OF SEQUENCE LISTING

The content of the electronically submitted sequence listing, file name: Q267839_Substitute_ Sequence_Listing_as_filed.txt; size: 17.7 kilobytes; and date of creation: Dec. 21, 2023, filed herewith, is incorporated herein by reference in its entirety.

TECHNICAL FIELD

The present invention relates to a biomarker for diagnosing osteoarthritis, and more particularly to a composition for diagnosing osteoarthritis comprising an agent for measuring the expression or activity level of TRIM24 and/or RIP3, and to a guide for therapeutic application.

BACKGROUND ART

Osteoarthritis (OA) is a degenerative joint disease mainly caused by inhibition of cartilage extracellular matrix (ECM) synthesis and promotion of cartilage destruction. Many age-related pathologic risk factors and pathophysiological processes contribute to the progression of osteoarthritis. Factors associated with mechanical stress, including joint instability and damage, and aging, which increases the incidence of osteoarthritis, are potential osteoarthritis-inducing mechanisms. These factors lead to degradation of the extracellular matrix (ECM) by matrix metalloproteinase (MMP) due to the activation of biochemical pathways in chondrocytes, which are a unique type of cell that produces various catabolic and anabolic factors, and also to disruption of ECM synthesis through dedifferentiation and apoptosis of chondrocytes (Pelletier J. P. et al., Arthritis Rheum., 44:1237-47, 2001). In particular, once damaged, cartilage which makes up the joints, is not normally regenerated in vivo. When joint cartilage is damaged, daily activities are restricted due to severe pain, and when chronic, it causes critical osteoarthritis, which interferes with normal life and professional activities.

Osteoarthritis, characterized by articular cartilage destruction, is caused by an imbalance of anabolic and catabolic factors due to mechanical stress, and these factors alter biochemical pathways in chondrocytes, reduce the ability to produce ECM, and degrade ECM molecules via catabolic matrix-degrading enzymes to thus exert an inflammatory response. Numerous data suggest that chondrocyte death is involved in osteoarthritis pathogenesis (Ryu J. H. et al., Cell Death Differ 2012; 19(3):440-50; Thomas C. M., F. et al., Osteoarthritis Cartilage 2007; 15(1):27-34). Apoptosis is considered to eliminate dedifferentiated chondrocytes without releasing type II collagen or other ECM components, whereas necroptosis is a recently described form of pathophysiological cell death that causes the cell membrane to burst, having detrimental effects on surrounding tissues. Necroptotic cells release damage-associated molecular patterns that trigger a strong inflammatory response, and thus necroptosis is more immunogenic than apoptosis and promotes inflammation and ECM degradation.

Necroptosis is mainly mediated by receptor-interacting protein kinase 1 (RIP1), RIP3, and mixed-lineage kinase domain-like protein (MLKL). Assembly and activation of the RIP1-RIP3 complex is dependent on the kinase activity of both proteins. RIP3 activation leads to the phosphorylation of MLKL, which translocates to the cell membrane and disrupts the same. The complex role of RIP3 in cell death, inflammation, tumorigenesis, and metabolism has been extensively studied, along with tissue injury mediators and circulating markers of disease progression and severity. RIP1 and RIP3 inhibition has been reported to improve outcomes in numerous mouse pathology models, including kidney, brain and heart ischemic reperfusion injury, pancreatitis, and acetaminophen-induced hepatitis models. Moreover, RIP3 is able to act both independently and dependently of the substrate MLKL, suggesting that RIP3 and MLKL exert tissue-specific effects.

A recent report suggested that RIP3 promotes arthritis pathogenesis through the TLRTRIF-RIP3-IL-1β axis independent of MLKL (Lawlor K. E. et al., Nat. Commun. 2015; 6:6282), and another study found that the p55TNFR-IKK2-RIP3 axis orchestrates synovial fibroblast arthritogenic and cell death responses (Armaka M. et al., Nat. Commun. 2018; 9(1):618), but these are all studies based on rheumatoid arthritis models. The physiological and pathological roles of RIP3 in cartilage have not yet been addressed, and there has been no study on whether RIP3-mediated signaling is involved in osteoarthritis pathogenesis.

The present inventors have studied the basic molecular mechanism of how RIP3 is involved in osteoarthritis pathogenesis using human osteoarthritis cartilage samples and destabilization of medial meniscus (DMM) surgery-induced osteoarthritis mouse models, and thus ascertained that, when osteoarthritis develops and progresses, the expression of TRIM24, which is a regulator of RIP3 expression, is decreased, whereby the expression of RIP3 is increased, and particularly, it has been identified through the present invention that the time when the expression of RIP3 is increased and the expression of TRIM24 is decreased, which are inversely correlated, is the time when the joint is destroyed, indicating that TRIM24 and RIP3 may be useful as biomarkers for early diagnosis of osteoarthritis, thereby culminating in the present invention.

CITATION LIST

Non-Patent Literature (Non-Patent Document 1) Pelletier J. P. et al., Arthritis Rheum., 44:1237-47, 2001

(Non-Patent Document 2) Ryu J. H. et al., Cell Death Differ., 19(3):440-50, 2012

(Non-Patent Document 3) Thomas C. M., F. et al., Osteoarthritis Cartilage, 15(1):27-34, 2007

(Non-Patent Document 4) Lawlor K. E. et al., Nat. Commun., 6:6282, 2015

(Non-Patent Document 5) Armaka M. et al., Nat. Commun., 9(1):618, 2018

DISCLOSURE

Technical Problem

It is an object of the present invention to provide a novel use of TRIM24 and RIP3 as biomarkers for diagnosing osteoarthritis.

Technical Solution

In order to accomplish the above object, the present invention provides a composition for diagnosing osteoarthritis comprising an agent for measuring the expression or activity level of TRIM24 and/or RIP3.

In addition, the present invention provides a kit for diagnosing osteoarthritis comprising the composition.

In addition, the present invention provides a method of screening a material for preventing or treating osteoarthritis comprising (a) treating cells with a candidate material for preventing or treating osteoarthritis; and (b) selecting a material that increases the expression of TRIM24 and/or decreases the expression of RIP3 in the cells as a material for preventing or treating osteoarthritis.

In addition, the present invention provides a method of diagnosing osteoarthritis comprising using an agent for measuring the expression or activity level of TRIM24 and/or RIP3.

In addition, the present invention provides the use of the agent for measuring the expression or activity level of TRIM24 and/or RIP3 in the diagnosis of osteoarthritis.

DESCRIPTION OF THE DRAWINGS

FIG. 1A shows Protein Atlas data showing RIP1, RIP3 and MLKL tissue expression patterns (modified from Protein Atlas), FIG. 1B shows expression levels of necroptosis regulators in various tissue samples, with protein extracts analyzed through Western blotting (upper panel) and quantification of Western blotting (lower panel), FIG. 1C shows quantification of Western blotting results in FIG. 2A (n=3), FIG. 1D shows chondrocytes lysed in an M2 buffer, Laemmli SDS buffer (L), RIPA buffer (R), or RIPA buffer (R+So) with sonication, in which the lysates were analyzed through Western blotting and vimentin was used as a positive control for insoluble protein detection (n=3), FIG. 1E shows the results of Western blotting of cell lysates after treatment of chondrocytes with MG132, CQ, or 10 mg/mL E64d+10 mg/mL pepstatin A for 6 hours, in which NIK and LC3II were controls that blocked proteasome- and lysosome-dependent degradation, respectively (n=3), FIG. 1F shows quantification of Western blotting results in FIG. 2B (n=3), FIG. 1G shows the results of Western blotting of cell lysates after treatment of MEFs and chondrocytes with TSZ (TNF+zVAD+SMAC mimetic) for a predetermined time (n=3), and FIG. 1H shows the results of Western blotting of cell lysates after treatment of MEFs and chondrocytes with TSZ (TNF+zVAD+SMAC mimetic) (left panel) (n=3), of analysis of cytotoxicity through MTT assay or phase-contrast microscopy after treatment of MEFs and chondrocytes with TSZ for a predetermined time (middle), and of LDH assay of TNF-induced cell death (right), values being represented as mean±SEM, statistical analyses being performed using a two-tailed t-test.

FIG. 2A shows the expression levels of necroptosis regulators in chondrocytes, in which proteins extracted from wild-type and MLKL knockout MEFs, bone-marrow-derived monocytes (BMDM), macrophages, cartilage, and primary mouse articular chondrocytes were analyzed through Western blotting (n=3), FIG. 2B shows the results of Western blotting of cell lysates after treatment of MEFs and chondrocytes with TSZ (TNF+zVAD+SMAC mimetic) (n=3), FIG. 2C shows undamaged and damaged human cartilage stained using Alcian blue, Safranin-O, and RIP3, p-MLKL and MLKL immunostaining (n=5), with a scale bar of 100 μm, FIG. 2D shows RIP3 expression in undamaged and damaged human osteoarthritis cartilage measured by qPCR (n=5), values being represented as mean±SEM, statistical analyses being performed using a two-tailed t-test, FIG. 2E shows the results of Western blotting of RIP3, p-RIP3, MLKL and p-MLKL in chondrocytes infected with Ad-C (control) or Ad-Rip3 at the indicated MOIs (n=3), and FIG. 2F shows gene set enrichment analysis (GSEA) of RIP3-related genes (listed in Table 3) in treated cells compared to controls.

FIG. 3A shows relative expression levels of indicated proteins determined based on immunohistochemistry of undamaged and damaged human cartilage shown in FIG. 2C (n=5), FIG. 3B shows quantification of Western blotting results in FIG. 2E (n=3), FIG. 3C shows the results of Western blotting of necroptosis regulators in Ad-Rip3- and Ad-C-infected RIP1−/− MEFs and Flag-RIP3-transfected MEFs (n=3), FIG. 3D shows the results of Western blotting (left) and gene expression (right) of RIP3 and p-RIP3 in chondrocytes infected with Ad-C or Ad-Rip3, in which differentially expressed genes (DEGs) between Ad-Rip3- and Ad-C-infected chondrocytes were selected using fold change (FC)>3, the top 10 upregulated DEGs (Up-DEGs) and the top 10 osteoarthritis-related Up-DEGs were listed by RIP3 overexpression (middle), functional annotation was significantly enhanced in Up-DEGs, hypergeometric tests were performed using hallmark gene annotation in MSigDB (software.broadinstitute.org/gsea/msigdb), an enrichment score defined as −log 10 (q-value) was calculated, and RT-PCR analysis of MMP3 was performed in chondrocytes infected with Ad-C or Ad-Rip3 (right), and FIG. 3E shows significantly rich functional terms in Up-DEGs, functional annotation being obtained from the curated gene set (C2) of MSigDB, values being represented as mean±SEM, statistical analyses being performed using a two-tailed t-test.

FIG. 4A shows the results of RT-PCR (left) and qPCR (right) of RIP3, MMP3, MMP13 and COX2 in chondrocytes infected with Ad-C or Ad-Rip3 at the indicated MOIs (n=5), FIG. 4B shows the results of Western blotting thereof, FIG. 4C shows the results of qPCR analysis of Adamts4, Adamts5, aggrecan, and Col2a1 in Ad-Rip3-infected chondrocytes (n=5), FIG. 4D shows the activity of aggrecanase (left) and collagenase (right) by Ad-Rip3 infection in chondrocytes (n=5), FIG. 4E shows cartilage destruction and osteoarthritis development in mouse knee joints injected intra-articularly with Ad-C and Ad-Rip3 assessed by Safranin-O staining, OARSI grading, osteophyte formation, and subchondral bone plate thickness (n=9), and FIG. 4F shows the results of RIP3, MMP3, MMP13, COX2, MLKL and p-MLKL immunostaining in Ad-C- or Ad-Rip3-injected cartilage, statistical analyses being performed using one-way ANOVA with Bonferroni's test (FIGS. 4A, 4C and 4D), a nonparametric Mann-Whitney U test (FIG. 4E, OARSI grading, osteophyte formation), and a two-tailed t-test (FIG. 4E, subchondral bone plate), with a scale bar of 100 μm.

FIGS. 5A and 5B respectively show the results of relative expression levels of Western blotting results in FIG. 2B and of RT-PCR analysis for the indicated proteins or transcript levels in chondrocytes infected with Ad-C or Ad-Rip3 at the indicated MOIs (n=5), FIGS. 5C and 5D show relative expression levels of the indicated proteins determined based on immunohistochemistry in Ad-C- or Ad-Rip3-injected cartilage in FIG. 4F and on cartilage of DMM-operated WT or Rip3 KO mice in FIG. 6B (n=9), respectively, FIG. 5E shows the results of analysis of cytotoxicity through LDH assay or phase-contrast microscopy in chondrocytes infected with Ad-C or Ad-Rip3 at the indicated MOIs, in which control MEFs were treated with TSZ for the indicated time and analyzed for cytotoxicity by LDH assay or phase-contrast microscopy, FIG. 5F shows the results of apoptosis-related protein pattern analysis of chondrocytes infected with Ad-C or Ad-Rip3 at the indicated MOIs under apoptosis-inducing conditions, TC (30 ng/mL TNF+1 mg/mL cycloheximide (CHX)), in which chondrocytes were also treated with TC without RIP3 overexpression and cell lysates were analyzed through Western blotting, and FIG. 5G shows TNF-induced downstream signals in chondrocytes and RIP3-overexpressing chondrocytes, in which cells were treated with TNF for a predetermined time and cell lysates were analyzed through Western blotting, values being represented as mean±SEM and assessed using one-way ANOVA with Bonferroni's test (FIGS. 5A and 5D) or a two-tailed t-test (FIG. 5C).

FIG. 6A shows the results of assessment of cartilage destruction through Safranin-O staining, OARSI grading, osteophyte formation, and subchondral bone plate thickness, and FIG. 6B shows the results of assessment of cartilage destruction through RIP3, MMP3, MMP13, COX2, MLKL, and p-MLKL immunohistochemical staining, values being represented as mean±standard deviation of the indicated number of independent experiments, statistical analyses being performed using one-way ANOVA with Bonferroni's test (FIG. 6A), a nonparametric Mann-Whitney U test (FIG. 6A, OARSI grading, osteophyte formation), or a two-tailed t-test (FIG. 6A, subchondral bone plate thickness), with a scale bar of 100 μm.

FIG. 7A shows the results of analysis of transcriptional regulators analyzed with Ingenuity Pathway Analysis (IPA) software (QIAGEN, www.qiagenbioinformatics.com/products/ingenuitypathway-analysis) to predict upstream regulators based on microarray data, analyzed data were filtered by activation Z-score>1 or <−1, and regulators were not required to be expressed in the analyzed samples.

FIGS. 7B and 7C respectively show MEFs and chondrocytes infected with Ad-C or Ad-Trim24 shRNA at the indicated MOIs, in which cell lysates were analyzed through Western blotting (left) (n=3) and qPCR (right) (n=4), and FIG. 7D shows the results of Western blotting of RIP3, p-RIP3, and TRIM24 in chondrocytes infected with Ad-C or Ad-Rip3 (left) (n=3) and of qPCR analysis of Rip3 and Trim24 in chondrocytes infected with Ad-C or Ad-Rip3 (right) (n=4), values being represented as mean±standard deviation, statistical analyses being performed using a two-tailed t-test.

FIGS. 8A, 8B, and 8C show quantification of Western blotting results in FIG. 7B, FIG. 7C, and FIG. 7D (n=3), respectively, FIG. 8D shows the results of Western blotting of TRIM24, RIP3, and COX2 in MEFs infected with Ad-C or Ad-Trim24 shRNA at the indicated MOIs (n=3) (left), of quantification of Western blotting results represented as mean±standard deviation based on 3 independent experiments (middle), and of qPCR analysis of Mmp3, Mmp13 and Cox2 in MEFs infected with Ad-C or Ad-Trim24 shRNA (n=4) (right), FIG. 8E shows relative expression levels of the indicated proteins determined based on Western blotting in FIG. 9B in chondrocytes infected with Ad-C or Ad-Trim24 shRNA at the indicated MOIs (n=5), and FIG. 8F shows the results of analysis of cytotoxicity through phase-contrast microscopy in chondrocytes infected with Ad-C or Ad-Trim24 shRNA at the indicated MOIs (left) and of qPCR analysis of Rip3, Mmp3, Cox2 and Trim24 in chondrocytes infected with Ad-C or Ad-Trim24 shRNA (right) (n=9), values being represented as mean±standard deviation, statistical analyses being performed using a two-tailed t-test (FIGS. 8A to 8D) or one-way ANOVA with Bonferroni's test (FIG. 8E).

FIGS. 9A and 9B respectively show the results of RT-PCR (left) and qPCR (right) and of Western blotting of TRIM24, RIP3, MMP3 and COX2 in chondrocytes infected with Ad-C or Ad-Trim24 shRNA at the indicated MOIs (n=5), FIG. 9C shows the results of assessment of cartilage destruction, osteophyte formation, and subchondral bone thickness through scoring in knee joint cartilage of WT mice intra-articularly injected with Ad-C or Ad-Trim24 shRNA stained with Safranin-O (n=9), FIG. 9D shows the results of TRIM24, RIP3, MMP3, MMP13, and COX2 immunostaining in cartilage injected with Ad-C or Ad-Trim24 shRNA, and FIG. 9E shows relative expression levels of the indicated proteins determined based on immunohistochemistry of cartilage every 2 weeks after DMM surgery (n=9), values being represented as means, data being analyzed using one-way ANOVA with Bonferroni's test (FIG. 9A), a nonparametric Mann-Whitney U test (FIG. 9C; OARSI grading, osteophyte formation) or a two-tailed t-test (FIG. 9C; subchondral bone plate thickness), with a scale bar of 100 μm.

FIG. 10A shows relative expression levels of the indicated proteins determined based on immunohistochemistry of chondrocytes infected with Ad-C or Ad-Trim24 shRNA at the indicated MOIs according to FIG. 9D (n=9), WT mice being subjected to DMM surgery to induce cartilage destruction (n=5) (FIGS. 10B and 10C), FIG. 10B shows scoring of osteoarthritis symptoms using the OARSI score and by assessing osteophyte formation and subchondral bone formation, and FIG. 10C shows relative expression levels of the indicated proteins determined based on immunohistochemistry of DMM-operated cartilage according to FIG. 9E, values being represented as mean±standard deviation, data being analyzed using a two-tailed t-test (FIG. 10A) or one-way ANOVA with Bonferroni's test (FIGS. 10B and 10C).

FIG. 11A schematically shows in silico drug screening using a CMap approach and the top 10 predicted compounds, FIG. 11B shows the results of analysis of binding affinities of AZ-628, neratinib and selumetinib to RIP3 using AutoDock Vina, FIG. 11C shows MMP3, MMP13 and COX2 expression determined by RT-PCR (upper) and Western blotting (lower) in chondrocytes infected with Ad-C or Ad-Rip3 in the presence or absence of AZ-628, selumetinib, or neratinib at the indicated dose (n=5), FIG. 11D shows the inhibition of RIP3 kinase activity by AZ-628, in which chondrocytes were infected with adenovirus Ad-C or Ad-Rip3 and treated with GSK'872, AZ-628, and HS-1371 and cell lysates were analyzed through Western blotting (n=3), FIG. 11E shows the results of qPCR analysis of Mmp3 under the same conditions as FIG. 11C (n=9), FIG. 11F shows the results of cytotoxicity assessed using LDH release assay (n=6), and FIG. 11G shows a diagram of RIP3-mediated osteoarthritis and the inhibitory effects of AZ-628, values being represented as mean±SEM, statistical analyses being performed using a two-tailed t-test.

FIGS. 12A to 12D show selection of novel inhibitors to modulate RIP3 kinase activity. FIG. 12A shows the 3D structures of the inhibitor molecules from PubChem, FIG. 12B shows the effects of AZ-628, selumetinib, and neratinib on chondrocyte viability detected by LDH assay (n=5), FIG. 12C shows the results of qPCR of relative expression levels of the indicated proteins in chondrocytes infected with Ad-C or Ad-Rip3 in the presence or absence of AZ-628, selumetinib, and neratinib at the indicated doses (n=5), and FIG. 12D shows the confirmation of Western blotting results in FIG. 11C, data being analyzed using one-way ANOVA with Bonferroni's test.

FIGS. 13A to 13F show that AZ-628 acts as a potent inhibitor of RIP3-mediated osteoarthritis pathogenesis. FIG. 13A shows the results of analysis of binding affinity of 14 compounds using RIP3, FIG. 13B shows computational docking models for RIP3 and small molecules, FIG. 13C shows quantification results of Western blotting in FIG. 11D (n=3), FIG. 13D shows the results of qPCR analysis of Rip3, Cox2, and Mmp3 expression in chondrocytes infected with Ad-C or Ad-Rip3 (n=9), FIG. 13E shows cytotoxicity assessed through Western blotting (left) and phase-contrast microscopy (right) in chondrocytes infected with Ad-C or Ad-Rip3, and FIG. 13F shows a diagram of AZ-628 or phosphate binding to the RIP3 kinase domain, values being represented as mean±standard deviation, statistical analyses being performed using a two-tailed t-test.

DETAILED DESCRIPTION AND EXEMPLARY EMBODIMENTS

Figure 1A:
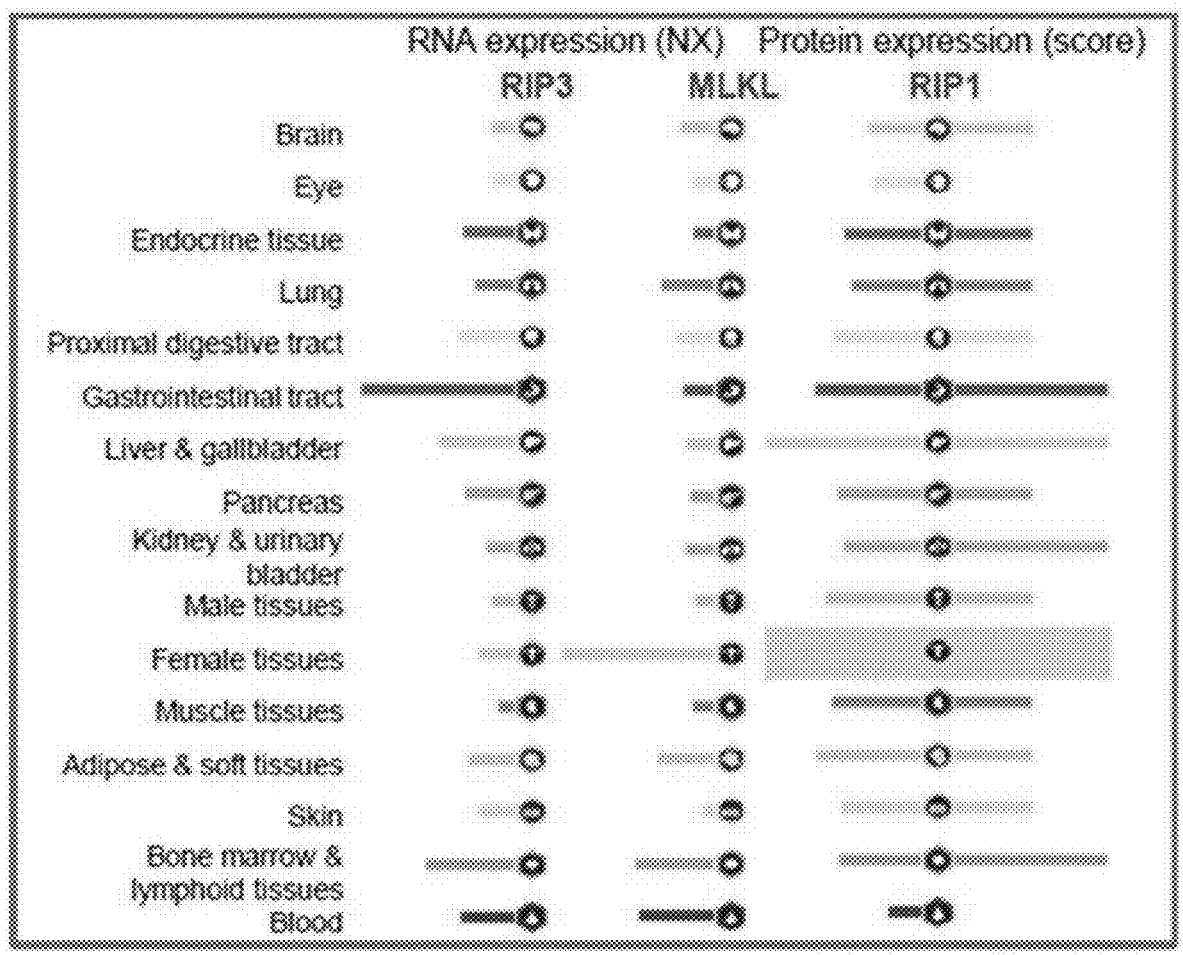
FIGS. 1A to 1H show that MLKL expression is not detected in chondrocytes.

Unless otherwise defined, all technical and scientific terms used herein have the same meanings as those typically understood by those skilled in the art to which the present invention belongs. Generally, the nomenclature used herein is well known in the art and is typical.

Arthritis is broadly divided into non-inflammatory arthritis and inflammatory arthritis. Non-inflammatory arthritis and inflammatory arthritis are representatively exemplified by osteoarthritis (OA, degenerative arthritis) and rheumatoid arthritis, respectively.

Osteoarthritis is also called degenerative arthritis, and although the cause thereof is not yet clear, it is known that various triggers, such as heredity, external injury, obesity, aging, metabolic abnormalities and the like are involved therein. It has been reported that such triggers break the balance between attack and defense factors in chondrocytes, promote cartilage destruction and deepen cartilage abrasion, so pathological changes of osteoarthritis cause the patient to feel pain and limit joint movement.

On the other hand, in the case of rheumatoid arthritis (RA), progression of the disease due to an autoimmune reaction is known to be an important cause, unlike osteoarthritis caused by destruction of chondrocytes and cartilage. Rheumatoid arthritis is a chronic autoimmune disease characterized by inflammation and proliferation of synovial cells, and osteoporosis and bone erosion around the joints occur, unlike osteoarthritis. In rheumatoid arthritis, inflammation of the synovial membrane spreads to joint capsules, ligaments, and tendons, invades the bone, and progresses. Therefore, the causes and progression stages of osteoarthritis and rheumatoid arthritis are completely different, and the treatment methods therefor are also different.

In the present invention, the basic molecular mechanism of how RIP3 is involved in osteoarthritis pathogenesis was studied using human osteoarthritis cartilage samples and destabilization of medial meniscus (DMM) surgery-induced osteoarthritis mouse models. As a result, it was confirmed that the expression of TRIM24, which is a regulator of RIP3 expression, was decreased with development and progression of osteoarthritis, thereby increasing RIP3 expression.

Accordingly, an aspect of the present invention pertains to a composition for diagnosing osteoarthritis comprising an agent for measuring the expression or activity level of TRIM24 and/or RIP3.

In the present invention, TRIM24 may be represented by the amino acid sequence of SEQ ID NO: 25.

In the present invention, RIP3 may be represented by the amino acid sequence of SEQ ID NO: 27.

In the present invention, the agent may be an antibody that specifically binds to TRIM24, an antigen-binding fragment thereof, or an aptamer and/or an antibody that specifically binds to RIP3, an antigen-binding fragment thereof, or an aptamer, but is not limited thereto.

In the present invention, the agent may be a primer or probe that specifically binds to a polynucleotide encoding TRIM24 and/or a primer or probe that specifically binds to a polynucleotide encoding RIP3, but is not limited thereto.

Another aspect of the present invention pertains to a kit for diagnosing osteoarthritis comprising the composition.

In the present invention, the kit may be a PCR assay kit, an immunoassay kit, or a microarray kit, but is not limited thereto.

Still another aspect of the present invention pertains to a method of screening a material for preventing or treating osteoarthritis comprising (a) treating cells with a candidate material for preventing or treating osteoarthritis and (b) selecting a material that increases the expression of TRIM24 and/or decreases the expression of RIP3 in the cells as a material for preventing or treating osteoarthritis.

Yet another aspect of the present invention pertains to a method of diagnosing osteoarthritis comprising using an agent for measuring the expression or activity level of TRIM24 and/or RIP3.

Still yet another aspect of the present invention pertains to the use of the agent for measuring the expression or activity level of TRIM24 and/or RIP3 in the diagnosis of osteoarthritis.

In the present invention, the terms "osteoarthritis (OA) and "degenerative arthritis" are used interchangeably, and should be understood to have the same meaning.

In an embodiment of the present invention, the expression or activity level of TRIM24 and/or RIP3 may be measured in a biosample. As used herein, the term "biosample" refers to any sample obtained from the human body, including but not limited to samples of cells or tissues of cartilage (especially articular cartilage), urine, saliva, blood, plasma, or serum. In the present invention, the biosample is preferably a cartilage sample isolated from a subject suspected of osteoarthritis or a body fluid sample isolated from cartilage, particularly preferably a cartilage sample suspected of being damaged by osteoarthritis or a body fluid isolated from cartilage.

As used herein, the term "diagnosis" refers to determining the susceptibility of a subject to a specific disease or disorder, determining whether a subject currently has a specific disease or disorder, determining the prognosis of a subject with a specific disease or disorder (e.g. identifying osteoarthritis status, determining the stage of arthritis, or determining the responsiveness of osteoarthritis to treatment), or therametrics (e.g. monitoring the status of a subject to provide information about the efficacy of treatment).

As used herein, the term "prognosis" includes prediction of the likely course of disease, particularly remission of disease, regeneration of disease, or recurrence of arthritis. "Prognosis" in the present invention preferably means the possibility of the disease of the osteoarthritis patient being cured.

The antibody used in the present invention is a polyclonal or monoclonal antibody, preferably a monoclonal antibody. Antibodies may be prepared through methods commonly used in the art, for example, fusion methods, recombinant DNA methods, or phage antibody library methods. Although a general process for preparing an antibody is known and a detailed description thereof is omitted, for example, the preparation of a monoclonal-antibody-producing hybridoma cell may be accomplished by fusing an immortalized cell line with an antibody-producing lymphocyte. A polyclonal antibody may be obtained by injecting a protein antigen into a suitable animal, collecting antisera from the animal, and then isolating the antibody from the antisera using known affinity techniques.

When the present invention is implemented using an antibody or an aptamer, the present invention may be used to diagnose osteoarthritis according to a typical immunoassay method.

Such immunoassays may be performed according to various previously developed quantitative or qualitative immunoassay protocols. These immunoassay formats include radioimmunoassay, radioimmunoprecipitation, immunoprecipitation, immunohistochemical staining, enzyme-linked immunosorbent assay (ELISA), capture-ELISA, inhibition or competition assay, sandwich assay, flow cytometry, immunofluorescence staining, and immunoaffinity purification, but are not limited thereto.

For example, when the method of the present invention is performed using a radioimmunoassay method, an antibody labeled with a radioisotope (e.g. C14, I125, P32, or S35) may be used to detect a marker molecule of the present invention.

When the present invention is implemented using an ELISA method, a specific embodiment of the present invention includes 1) coating the surface of a solid substrate with a lysate of an unknown biosample to be analyzed, 2) reacting the lysate with an antibody against a marker as a primary antibody, 3) reacting the product of step 2 with an enzyme-conjugated secondary antibody, and 4) measuring the activity of the enzyme.

Here, a suitable solid substrate is a hydrocarbon polymer (e.g. polystyrene or polypropylene), glass, metal or gel, most preferably a microtiter plate. The enzyme bound to the secondary antibody includes, but is not limited to, an enzyme catalyzing a color reaction, a fluorescence reaction, a luminescence reaction, or an infrared reaction, examples of which include alkaline phosphatase, β-galactosidase, horseradish peroxidase, luciferase, and cytochrome P450. When alkaline phosphatase is used as the enzyme binding to the secondary antibody, a substrate for a color reaction, such as bromochloroindolyl phosphate (BCIP), nitroblue tetrazolium (NBT), naphthol-AS-BI-phosphate, or ECF (enhanced chemifluorescence), may be used, and when horseradish peroxidase is used, a substrate, such as chloronaphthol, aminoethylcarbazole, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (tetramethylbenzidine), ABTS (2,2'-azine-di[3-ethylbenzthiazoline sulfonate]), o-phenylenediamine (OPD), naphthol/pyronine, glucose oxidase, t-NBT (nitroblue tetrazolium), or m-PMS (phenazine methosulfate), may be used.

When the present invention is implemented using a capture-ELISA method, a specific embodiment of the present invention includes 1) coating the surface of a solid substrate with an antibody against a marker of the present invention as a capture antibody, 2) reacting the capture antibody with a sample, 3) reacting the product of step 2 with a detecting antibody to which a signal-generating label is bound and which specifically responds to TRIM24 and/or RIP3, and 4) measuring a signal generated from the label.

Here, the detecting antibody has a label that generates a detectable signal. Examples of the label may include, but are not limited to, chemicals (e.g. biotin), enzymes (alkaline phosphatase, β-galactosidase, horseradish peroxidase, and cytochrome P450), radioactive materials (e.g. C14, I125, P32 and S35), fluorescent materials (e.g. fluorescein), luminescent materials, chemiluminescent materials, and fluorescence resonance energy transfer (FRET).

In the ELISA method and the capture-ELISA method, the final enzyme activity measurement or signal measurement may be performed according to various methods known in the art. Such signal detection enables qualitative or quantitative analysis of the marker of the present invention. The signal may be easily detected with streptavidin when biotin is used as the label, and with luciferin when luciferase is used.

According to another embodiment of the present invention, an aptamer that specifically binds to the marker of the present invention may be used instead of the antibody. The aptamer is an oligonucleic acid or peptide molecule, and such an aptamer is generally well known, so a detailed description thereof will be omitted.

By analyzing the final signal intensity in the immunoassay process described above, osteoarthritis may be diagnosed. Specifically, upon high expression of the RIP3 protein in a biosample, when the signal is stronger than in a normal biosample (e.g. articular chondrocytes or cartilage, blood, plasma, or serum), particularly by 20% or more, preferably 30% or more, and more preferably 50% or more, 80% or more, or 100% or more, osteoarthritis may be diagnosed.

Conversely, upon low expression of the TRIM24 protein in a biosample, when the signal is weaker than in a normal biosample (e.g. articular chondrocytes or cartilage, blood, plasma, or serum), particularly by 70% or less compared to a normal control, preferably 50% or less, and more preferably 30% or less, 20% or less, or 10% or less, osteoarthritis may be diagnosed.

Since the changes in TRIM24 and RIP3 expression levels may be observed 4 weeks after induction of osteoarthritis, the diagnosis time may be significantly accelerated compared to diagnosis of osteoarthritis using MMP3, MMP13, and COX2, which increase in expression levels from 6 weeks, and the present invention may be advantageously utilized for early diagnosis.

When the composition of the present invention is a composition for a microarray, a probe is immobilized on the solid surface of the microarray. When the composition of the present invention is a composition for gene amplification, it may comprise a primer.

The primer or probe used in the present invention may comprise a primer or probe that specifically binds to a polynucleotide encoding TRIM24 and/or a primer or probe that specifically binds to a polynucleotide encoding RIP3, each having a sequence complementary to a portion of a polynucleotide sequence encoding TRIM24 or a portion of a polynucleotide sequence encoding RIP3. As used herein, the term "complementary" means having complementarity to the extent of being capable of selectively hybridizing to the nucleotide sequence described above under certain hybridization or annealing conditions. Therefore, the term "complementary" has a meaning different from the term "perfectly complementary", and the primer or probe of the present invention may comprise at least one mismatched nucleotide sequence, so long as it is capable of selectively hybridizing to the nucleotide sequence described above.

In the microarray comprising the composition of the present invention, the probe is used as a hybridizable array element, and is immobilized on a substrate. Preferred examples of the substrate include suitable rigid or semi-rigid supports, such as membranes, filters, chips, slides, wafers, fibers, magnetic or non-magnetic beads, gels, tubes, plates, polymers, microparticles, and capillaries. The hybridizable array element described above is arranged and immobilized on the substrate. Such immobilization is carried out using a chemical bonding method or a covalent bonding method such as UV. For example, the hybridizable array element may be bound to a glass surface modified to include an epoxy compound or an aldehyde group, and may also be bound to a polylysine-coated surface by UV. In addition, the hybridizable array element may be bound to the substrate via a linker (e.g. ethylene glycol oligomer and diamine). Meanwhile, the sample DNA applied to the microarray comprising the composition of the present invention may be labeled and hybridized with the array element on the microarray. The hybridization conditions may vary. Detection and analysis of the extent of hybridization may be variously performed depending on the labeling material.

A kit comprising the composition for diagnosing or prognosing osteoarthritis according to the present invention may be used based on hybridization. Here, a probe having a sequence complementary to the nucleotide sequence of the marker of the present invention is used.

Whether osteoarthritis is present may be determined through hybridization-based analysis using the probe that hybridizes to the nucleotide sequence of the marker of the present invention. The label of the probe may provide a signal to detect hybridization, and may be linked to an oligonucleotide. Suitable examples of the label include, but are not limited to, fluorophores (e.g. fluorescein, phycoerythrin, rhodamine, lissamine, and Cy3 and Cy5 (Pharmacia)), chromophores, chemiluminophores, magnetic particles, radioisotopes (P32 and S35), mass labels, electron-dense particles, enzymes (alkaline phosphatase or horseradish peroxidase), cofactors, substrates for enzymes, heavy metals (e.g. gold), antibodies, streptavidin, biotin, digoxigenin, and haptens with specific binding partners such as chelating groups. Labeling may be performed through any of various methods commonly practiced in the art, such as nick translation methods, random priming methods (Multiprime DNA labeling systems booklet, "Amersham" (1989)), and kination methods (Maxam & Gilbert, Methods in Enzymology, 65:499 (1986)). The label provides a signal that is detectable using fluorescence, radioactivity, chromometry, gravimetry, X-ray diffraction or absorption, magnetism, enzymatic activity, mass spectrometry, binding affinity, hybridization radiofrequency, or nanocrystals.

A nucleic acid sample to be analyzed may be prepared using mRNA obtained from various biosamples, and hybridization-based analysis may be performed by labeling target cDNA instead of the probe.

When the probe is used, the probe is hybridized with a cDNA molecule. In the present invention, suitable hybridization conditions may be determined in a series of processes by an optimization procedure. These procedures are carried out through a series of processes by those skilled in the art to establish protocols for use in the laboratory. For example, conditions such as temperature, concentration of components, hybridization and washing times, buffer components, and pH and ionic strength depend on various factors such as the length of the probe, the amount of GC, and the target nucleotide sequence. For example, high-stringency conditions among stringent conditions include hybridization using 0.5 M $NaHPO_4$, 7% sodium dodecyl sulfate (SDS), and 1 mM EDTA at 65° C., and washing using 0.1×SSC (standard saline citrate)/0.1% SDS at 68° C. Alternatively, high-stringency conditions include washing at 48° C. using 6×SSC/0.05% sodium pyrophosphate. Low-stringency conditions include washing at 42° C. using 0.2×SSC/0.1% SDS.

After the hybridization reaction, a hybridization signal emitted through the hybridization reaction is detected. The hybridization signal may be detected in various ways depending on the type of label that is bound to the probe. For example, when the probe is labeled with an enzyme, hybridization may be checked by reacting the substrate of the enzyme with a hybridization reaction product. Enzyme/substrate combinations that may be used include peroxidase (e.g. horseradish peroxidase) and a substrate such as chloronaphthol, aminoethylcarbazole, diaminobenzidine, D-luciferin, lucigenin (bis-N-methylacridinium nitrate), resorufin benzyl ether, luminol, Amplex red reagent (10-acetyl-3, 7-dihydroxyphenoxazine), HYR (p-phenylenediamine-HCl and pyrocatechol), TMB (tetramethylbenzidine), ABTS (2,2'-azine-di[3-ethylbenzothiazoline sulfonate]), 0-phenylenediamine (OPD), or naphthol/pyronine, alkaline phosphatase and a substrate such as bromochloroindolyl phosphate (BCIP), nitroblue tetrazolium (NBT), naphthol-AS-BI-phosphate, or ECF, and glucose oxidase and a substrate such as t-NBT (nitroblue tetrazolium) or m-PMS (phenazine methosulfate). When the probe is labeled with gold particles, detection may be carried out through a silver staining method using silver nitrate.

Therefore, when the method of detecting the osteoarthritis marker of the present invention is carried out based on hybridization, it specifically comprises 1) hybridizing a probe having a sequence complementary to the nucleotide sequence of the marker of the present invention to a nucleic acid sample and 2) detecting whether the hybridization reaction has occurred. By analyzing the intensity of the hybridization signal through the hybridization process, it is possible to determine whether osteoarthritis is present.

When the hybridization signal to the nucleotide sequence of the RIP3 marker in the sample is stronger than in a normal sample (e.g. articular chondrocytes or cartilage), particularly 1.5 times or more, preferably 2 times or more, and more preferably 3 times or more, osteoarthritis is diagnosed. In addition, when the hybridization signal to the nucleotide sequence of the TRIM24 marker in the sample is weaker than in a normal sample (e.g. articular chondrocytes or cartilage), particularly ½ or less, preferably ⅓ or less, and more preferably ⅕ or less, osteoarthritis is diagnosed.

The kit for diagnosing or prognosing osteoarthritis according to the present invention may be a gene amplification kit, and the term "amplification" refers to a reaction for amplifying a nucleic acid molecule. Various amplification reactions have been reported in the art, including polymerase chain reaction (PCR), reverse transcription-polymerase chain reaction (RT-PCR), ligase chain reaction (LCR), repair chain reaction, transcription-mediated amplification, self-sustained sequence replication (WO 90/06995), selective amplification of target polynucleotide sequences, consensus sequence primed polymerase chain reaction (CP-PCR), arbitrarily primed polymerase chain reaction (AP-PCR), nucleic-acid-sequence-based amplification (NASBA), strand displacement amplification, and loop-mediated isothermal amplification (LAMP), but the present invention is not limited thereto.

PCR is the best-known nucleic acid amplification method, and many modifications and applications thereof have been developed. For example, touchdown PCR, hot-start PCR, nested PCR, and booster PCR have been developed by modifying typical PCR procedures to increase the specificity or sensitivity of PCR. In addition, real-time PCR, differential display PCR (DD-PCR), rapid amplification of cDNA ends (RACE), multiplex PCR, inverse polymerase chain reaction (IPCR), vectorette PCR, and TAIL-PCR (thermal asymmetric interlaced PCR) have been developed for specific applications.

Therefore, in principle, the present invention performs a gene amplification reaction using a primer that binds to mRNA or cDNA and using mRNA in a biosample as a template.

In order to obtain mRNA, total RNA is isolated from the sample. Isolation of total RNA may be carried out according to typical methods known in the art. For example, total RNA in cells may be easily isolated using TRIzol. Then, cDNA is synthesized from the isolated mRNA, and this cDNA is amplified. Since total RNA of the present invention is isolated from a human sample, the end of the mRNA has a poly-A tail, so cDNA may be easily synthesized using an oligo dT primer and reverse transcriptase using this sequence characteristic. Then, the synthesized cDNA is amplified through a gene amplification reaction.

The primer used in the present invention may be hybridized or annealed to one site of the template to form a double-stranded structure. A variety of DNA polymerases may be used for the amplification of the present invention, including the "Klenow" fragment of *E. coli* DNA polymerase I, thermostable DNA polymerase, and bacteriophage T7 DNA polymerase. Preferably, the polymerase is a thermostable DNA polymerase obtainable from a variety of bacterial species. When carrying out the polymerization reaction, it is preferable to place excess amounts of the components necessary for the reaction in the reaction vessel. The excess amounts of the components required for the amplification reaction means amounts such that the amplification reaction is not substantially limited by the concentration of the components. It is required to add the reaction mixture with cofactors such as $Mg^{2+}$, dATP, dCTP, dGTP and dTTP such that the desired extent of amplification may be achieved. All enzymes used in the amplification reaction may be active under the same reaction conditions. In practice, the buffer provides approximately optimal reaction conditions for all enzymes. Therefore, the amplification process of the present invention may be performed in a single reactant without changing conditions such as addition of reactants. In the present invention, annealing is performed under stringent conditions that enable specific binding between the target nucleotide sequence and the primer. The stringent conditions for annealing are sequence-dependent, and vary according to environmental variables.

The cDNA of the nucleotide sequence of the marker of the present invention thus amplified is analyzed through a suitable method to investigate the expression level of the nucleotide sequence of the marker of the present invention. For example, the expression level of the nucleotide sequence of the marker of the present invention is measured by performing gel electrophoresis on the amplification reaction product described above and observing and analyzing the resulting band. Through this amplification reaction, when the expression of the nucleotide sequence of the RIP3 marker in the biosample is higher than in a normal sample (e.g. normal articular chondrocytes or cartilage, blood, plasma, or serum), particularly 1.5 times or more, preferably 2 times or more, and more preferably 3 times or more, osteoarthritis is diagnosed. In addition, when the expression of the nucleotide sequence of the TRIM24 marker in the biosample is lower than in a normal sample (e.g. normal articular chondrocytes or cartilage, blood, plasma, or serum), particularly ½ or lower, preferably ⅓ or lower, and more preferably ⅕ or lower, osteoarthritis is diagnosed.

Therefore, when the method of detecting the arthritis marker according to the present invention is performed based on an amplification reaction using cDNA, it specifically comprises 1) performing an amplification reaction using a primer annealed to the nucleotide sequence of the marker of the present invention and 2) analyzing the product of the amplification reaction to determine the expression level of the nucleotide sequence of the marker of the present invention. The marker of the present invention is a biomolecule, the expression level of which is significantly changed in the presence of osteoarthritis. A change in the expression level of this marker may be measured at the mRNA or protein level. As used herein, the term "high expression" refers to the case in which the expression level of a target nucleotide sequence in a sample to be investigated is higher than in a normal sample. For example, when expression analysis is performed according to an expression analysis method commonly used in the art, such as an RT-PCR method or an ELISA method, it means the case in which expression is determined to be high. For example, upon analysis according to the above-described analysis method, when the RIP3 marker is expressed about 1.5-10 times higher than in normal cells or tissues, osteoarthritis may be determined in the present invention. Conversely, as used herein, the term "low expression" refers to the case in which the expression level of a target nucleotide sequence in a sample to be investigated is lower than in a normal sample. For example, when expression analysis is performed according to an expression analysis method commonly used in the art, such as an RT-PCR method or an ELISA method, it means the case in which expression is determined to be low. For example, upon analysis according to the analysis method described above, when the TRIM24 marker is expressed to the low level corresponding to about ½-1/50 of that of normal cells or tissues, osteoarthritis may be determined in the present invention.

In the present invention, it can be confirmed that TRIM24 is expressed in normal tissues, but that TRIM24 is no longer expressed or the expression level thereof is decreased due to cartilage disruption in tissues in which osteoarthritis has occurred or is progressing.

In the present invention, it can be confirmed that RIP3 is not expressed in normal tissues or the expression level thereof is insignificant, but that RIP3 is expressed or the expression level thereof is significantly increased due to cartilage disruption in tissues in which osteoarthritis has occurred or is progressing.

Also, in the present invention, it can be confirmed that RIP3 has no activity or very weak activity in normal tissues, but that the activity thereof is observed or significantly increased due to cartilage disruption in tissues in which osteoarthritis has occurred or is progressing.

Therefore, it is possible to determine the stage of progression of osteoarthritis based on an increase in the expression level or activity of RIP3 in the present invention.

In the present invention, the expression level of TRIM24 in cartilage damaged by osteoarthritis is decreased by 10% or more, 20% or more, 30% or more, 40% or more, or 50% or more compared to a normal subject or undamaged tissue, but the present invention is not limited thereto.

In the present invention, the expression level or activity of RIP3 in cartilage damaged by osteoarthritis is increased by 10% or more, 20% or more, 30% or more, 40% or more, or 50% or more compared to a normal subject or undamaged tissue, but the present invention is not limited thereto.

In the present invention, TRIM24 expression is clearly confirmed in a normal subject, but TRIM24 is hardly expressed or the expression level thereof is significantly decreased in the presence of osteoarthritis, and the decrease in the expression level thereof may be easily determined by those skilled in the art.

Also, in the present invention, RIP3 expression is not confirmed or is insignificant in a normal subject, but the expression of RIP3 is confirmed or the level thereof is significantly increased in the presence of osteoarthritis, and the increase in the expression level thereof may be easily determined by those skilled in the art.

In the present invention, the expression levels of TRIM24 and RIP3 were detected in osteoarthritis mouse models, but when an antibody or antigen-binding fragment thereof, aptamer, primer, or probe, suitable for the detection of human TRIM24 and RIP3, is used, it will be apparent to those skilled in the art that osteoarthritis may be diagnosed in humans. Any antibody or antigen-binding fragment thereof, aptamer, primer, or probe, suitable for the detection of human TRIM24 and RIP3, may be used without limitation, so long as it is able to specifically detect the corresponding gene or protein.

EXAMPLES

Hereinafter, the present invention will be described in more detail with reference to examples. These examples are merely set forth to illustrate the present invention, and are not to be construed as limiting the scope of the present invention, as will be apparent to those skilled in the art.

Example 1. Experimental Method 1-1. Construction of Human Osteoarthritis Samples and Experimental Osteoarthritis Mouse Models Human cartilage samples were obtained from individuals 63 to 80 years old who had undergone total knee arthroplasty (Table 1). All patients provided written informed consent, and sample collection was approved by the IRB of the Catholic University of Korea (UC14CNSI0150).

Male C57BL/6 and Rip3−/− mice (C57BL/6; Dr. V. M. Dixit, Genentech, San Francisco, USA) were maintained according to the guidelines of the Institutional Animal Care and Use Committee, which approved all animal procedures at the Laboratory Animal Research Center of Ajou University.

TABLE 1

| No. | Age/gender | ICRS[a] grade | Joint | Weight (kg) | Height (m) | BMI[b] (kg/m$^2$) | Use |
|---|---|---|---|---|---|---|---|
| 1 | 65/F | 4 | Knee | 158 | 53 | 21.23 | IHC/qPCR |
| 2 | 80/F | 4 | Knee | 143.3 | 55.1 | 26.83 | IHC/qPCR |
| 3 | 72/F | 4 | Knee | 165 | 65 | 23.88 | IHC/qPCR |
| 4 | 63/F | 4 | Knee | 152 | 52 | 22.51 | IHC/qPCR |
| 5 | 69/F | 4 | Knee | 151 | 60 | 26.31 | IHC/qPCR |
| 6 | 73/F | 4 | Knee | 153.8 | 70.75 | 29.89 | IHC |
| 7 | 63/F | 4 | Knee | 156 | 72.2 | 29.67 | IHC |
| 8 | 73/F | 4 | Knee | 154 | 83 | 35 | IHC |
| 9 | 75/F | 4 | Knee | 154 | 55 | 23.19 | IHC |
| 10 | 63/F | 4 | Knee | 163 | 74.3 | 27.96 | IHC |

[a]ICRS, International Cartilage Repair Society;
[b]BMI, Body Mass Index

In order to produce experimental osteoarthritis models, 12-week-old male mice were subjected to DMM surgery and sacrificed 10 weeks after surgery. Female mice were not used because of the influence of female hormones on osteoarthritis pathogenesis. Adenoviruses for intra-articular injection were purchased from Vector Biolabs (Malvern, USA): Ad-C (1060), Ad-Rip3 (ADV-270614), and Ad-shRNA Trim24 (shADV-274975). Wild-type mice were injected in the knee joint with adenovirus ($1\times10^9$ PFUs/10 μL) twice weekly and sacrificed 3 weeks after the first adenovirus injection.

1-2. Isolation and Cell Culture of Primary Mouse Articular Chondrocytes

Mouse articular chondrocytes were isolated from the cartilage of ICR mice on the 5th day after birth, enzymatically digested with protease and collagenase, and then maintained in DMEM (Capricorn Scientific GmbH: Hessen, Germany) supplemented with 10% FBS, 100 units/mL penicillin and 100 μg/mL streptomycin. On the $3^{rd}$ day, cells ($4.25\times10^5$ cells/well) were infected with adenovirus or treated with recombinant protein. Mlkl+/+ and Mlkl−/− MEFs were maintained in DMEM supplemented with 10% FBS and penicillin-streptomycin.

1-3. Reagents

Antibodies were purchased from Enzo Biochem (New York, USA: RIP3), BD-Transduction Laboratories (Breda, Netherlands: RIP1), Santa Cruz Biotechnology (Dallas, USA: GAPDH, Actin, IκBα, Vimentin), Cell Signaling Technology (Danvers, USA: p-ERK, p-JNK, PARP, Caspase3, p-RIPK1, NIK), Abcam (Cambridge, UK: p-MLKL, p-RIP3, MLKL, TRIM24, COX2, MMP3, MMP13), and Sigma-Aldrich (St Louis, USA: LC3B, Vinculin). TNF-α and zVAD were purchased from R&D Systems (Minneapolis, USA). Cycloheximide, Pepstatin A, and MG132 were purchased from Calbiochem (San Diego, USA). Chloroquine diphosphate (CQ) and AZ-628 were purchased from Sigma-Aldrich. GSK 872 was purchased from Selleckchem (Houston, USA). Selumetinib was purchased from Abcam. Neratinib was purchased from MedChemExpress (Princeton, USA). HS-1371 was manufactured in house (Park H. H., Park S. Y., Mah S. et al., HS-1371, A novel kinase inhibitor of RIP3-mediated necroptosis. Exp. Mol. Med. 2018:50(9): 125).

1-4. Cell Viability Assay

Cell viability was assessed using a lactate dehydrogenase (LDH) colorimetric assay kit (Bio Vision (Milpitas, CA, USA)). Chondrocytes were dispensed into a 96-well dish ($1.5 \times 10^4$ cells/well), cultured for 24 hours (5% $CO_2$, 37° C.), and treated with various concentrations of AZ-628, selumetinib, and neratinib for 24 hours. The supernatant was analyzed using a microplate reader at 495 nm. Untreated (100% viable) and Triton X-100 treated (0% viable) samples were used for normalization. The viability was calculated as follows.

a protease inhibitor. Equal amounts of cell extracts were separated using SDS-PAGE (6% stacking gel and 10% running gel) and analyzed through immunoblotting.

1-6. Reverse Transcription (RT)-PCR and qPCR

Total RNA was extracted from articular chondrocytes using a TRIzol reagent (Molecular Research Center (Cincinnati, OH, USA)) and then reverse-transcribed into complementary DNA (cDNA) using ImProm-II™ Transcriptase (Promega (Madison, WI, USA)), followed by amplification through PCR or qPCR using the primers shown in Table 2 below. qPCR was performed using SYBR premix Ex Taq (TaKaRa Bio., Kusatsu, Shiga, Japan), and the results thereof were normalized to Gapdh and represented as fold changes compared to controls.

TABLE 2

| Gene | Origin | Strand | Sequence | Size (bp) | AT[a] (° C.) |
|---|---|---|---|---|---|
| ACAN | Mouse | [b]S | 5'-GAAGACGACATCACCATCCAG-3' (SEQ ID NO: 1) | 581 | 55 |
|  |  | [c]As | 5'-CTGTCTTTGTCACCCACACATG-3' (SEQ ID NO: 2) |  |  |
| Adamts4 | Mouse | S | 5'-CATCCGAAACCCTGTCAACTTG-3' (SEQ ID NO: 3) | 281 | 58 |
|  |  | As | 5'-GCCCATCATCTTCCACAATAGC-3' (SEQ ID NO: 4) |  |  |
| Adamts5 | Mouse | S | 5'-ATGTCGTGCGTCAAGTTATGG-3' (SEQ ID NO: 5) | 292 | 58 |
|  |  | As | 5'-TCAGTCCCATCCGTAACCTTTG-3' (SEQ ID NO: 6) |  |  |
| Col2a1 | Mouse | S | 5'-CACACTGGTAAGTGGGGCAAGA-3' (SEQ ID NO: 7) | 173 | 55 |
|  |  | As | 5'-GGATTGTGTTGTTTCAGGGTTCG-3' (SEQ ID NO: 8) |  |  |
| Cox2 | Mouse | S | 5'-GGTCTGGTGCCTGGTCTGATGAT-3' (SEQ ID NO: 9) | 724 | 63 |
|  |  | As | 5'-GTCCTTTCAAGGAGAATGGTGC-3' (SEQ ID NO: 10) |  |  |
| Gapdh | Mouse | S | 5'-TCACTGCCACCCAGAAGAC-3' (SEQ ID NO: 11) | 450 | 60 |
|  |  | As | 5'-TGTAGGCCATGAGGTCCAC-3' (SEQ ID NO: 12) |  |  |
| Mmp3 | Mouse | S | 5'-CTGTGTGTGGTTGTGTGCTCATCCTAC-3' (SEQ ID NO: 13) | 350 | 58 |
|  |  | As | 5'-GGCAAATCCGGTGTATAATTCACAATC-3' (SEQ ID NO: 14) |  |  |
| Mmp13 | Mouse | S | 5'-TGATGGACCTTCTGGTCTTCTGGC-3' (SEQ ID NO: 15) | 473 | 58 |
|  |  | As | 5'-CATCCACATGGTTGGGAAGTTCTG-3' (SEQ ID NO: 16) |  |  |
| Rip3 | Human | [b]S | 5'-ATGTCGTGCGTCAAGTTATGG-3' (SEQ ID NO: 17) | 138 | 60 |
|  |  | [c]As | 5'-CATAGGAAGTGGGGCTACGAT-3' (SEQ ID NO: 18) |  |  |
| Rip3 | Mouse | S | 5'-CAGTGGGACTTCGTGTCCG-3' (SEQ ID NO: 19) | 157 | 60 |
|  |  | As | 5'-CAAGCTGTGTAGGTAGCACATC-3' (SEQ ID NO: 20) |  |  |
| Trim24 | Mouse | S | 5'-CGAATGAAACTCATGCAACAACA-3' (SEQ ID NO: 21) | 152 | 60 |
|  |  | As | 5'-AGGTGCCGTAACCTGTATGTAA-3' (SEQ ID NO: 22) |  |  |
| Trim24 | Human | S | 5'-TGTGAAGGACACTACTGAGGTT-3' (SEQ ID NO: 23) | 138 | 60 |
|  |  | As | 5'-GCTCTGATACACGTCTTGCAG-3' (SEQ ID NO: 24) |  |  |

[a]AT, annealing temperature; [b]S, sense primer; [c]As, antisense primer $$100 - \frac{sampleLDH - \text{negative control}}{maxLDH - \text{negative control}} \times 100$$

1-5. Western Blotting

Cells were lysed in an M2 buffer, and mouse tissues were lysed in a lysis buffer containing 50 mM Tris-HCl (pH 7.5), 150 mM NaCl, 50 mM NaF, 1% Tween 20, 0.2% NP-40, and

1-7. Collagenase and Aggrecanase Activity Assay

Chondrocytes were dispensed into a 6-well dish ($2 \times 10^5$ cells/well) and infected with Ad-C or Ad-Rip3 adenovirus (Ad-C (1060), Ad-Rip3 (ADV-270614), Vector Biolabs (Malvern, USA)). Cells were cultured in FBS-free DMEM for 36 hours. The culture medium was collected and concentrated to equal volumes using Viva® Columns (Sartorius Stedim Biotech, Gottingen, Germany) according to the manufacturer's protocol. The concentrated samples were analyzed for total collagenase activity using EnzCheck™

Assay kits (Molecular Probes, Eugene, OR, USA). Collagenase activity was measured based on a fluorescence signal at Ex/Em=485/530 nm using a SYNERGY HI microplate reader (BioTek Instruments, Inc., Winooski, VT, USA). Aggrecanase activity was analyzed using the Aggrecanase Activity Assay Kit (Abnova, Taipei, Taiwan). Aggrecanase levels were quantified in the concentrated supernatant by measuring absorbance at 430 nm according to the manufacturer's protocol.

1-8. Histology and Immunohistochemistry

Human osteoarthritis cartilage and mouse knee joints were fixed in 4% paraformaldehyde and embedded in paraffin. Mouse knee joints were calcified in 0.5 M EDTA (pH 7.4) for 2 weeks. Paraffin-embedded samples were stained with Safranin-O or Alcian blue or through immunostaining. Cartilage destruction was assessed in experimental osteoarthritis mouse models by three observers unaware of the experimental grouping, followed by scoring according to the OARSI (Osteoarthritis Research Society International) grading system (grades 0-6). OARSI scores are represented as the mean of the maximum score for each mouse. Representative Safranin-O staining images were selected from the most advanced lesions of each section, and osteophyte maturity was quantified as previously described. Subchondral bone sclerosis was determined by measuring the thickness of the subchondral bone plate. Immunohistochemical staining was performed on human and mouse cartilage sections using MMP3, MMP13 and MLKL (Abcam), COX2, TRIM24 (Proteintech), and RIP3 (Enzo Biochem) antibodies.

1-9. Microarray Analysis

Mouse articular chondrocytes were infected with Ad-Rip3 or Ad-C (MOI, 800) for 36 hours. Total RNA was isolated using a TRIzol reagent (Molecular Research Center) and analyzed with an Affymetrix Mouse GeneChip 2.0 ST Array (Macrogen, Seoul, Korea) according to the manufacturer's protocol. Microarray data were stored in the gene expression omnibus with access code GSE154669 (www.ncbi.nlm.nih.gov/geo/query/acc.cgi?acc=GSE154669) (for Rip3).

1-10. In Silico Binding Assay

The chemical structure of the ligand that was used (FIG. 10A) was retrieved from the PubChem database (pubchem.ncbi.nlm.nih.gov). Molecular docking assays were performed using AutoDock Vina (ver. 1.1.2), which is widely used to determine protein-ligand binding affinity and localization. All docking assays were performed with rigid receptors and fully flexible ligands. Receptor coordinates and docking parameters were prepared using AutoDock MGLTools (ver. 1.5.6). Ligand binding affinity was assessed using the negative Gibbs free energy (A). Docking structures were visualized using PyMOL (ver. 1.3: DeLanoScientific, San Carlos, CA, USA).

1-11. Gene Set Enrichment Analysis (GSEA)

GSEA was performed using Java GSEA software (ver. 4.0.3: Broad Institute, MIT). Genes were ranked according to expression. Those upregulated or downregulated after RIP3 overexpression were selected as RIP3-related gene sets.

1-12. Statistical Analysis

All experiments were performed independently at least 4 times. Two independent groups were compared using a Shapiro-Wilk normality test, a Levene's homogeneity of variance test, and a two-tailed independent t-test. Multiple comparisons were performed using a Shapiro-Wilk test, a Levene's test, and a one-way analysis of variance with Bonferroni's post-hoc test. Data based on an ordinal grading system were analyzed using nonparametric Mann-Whitney U tests. P values less than 0.05 were considered statistically significant.

Figure 1B:
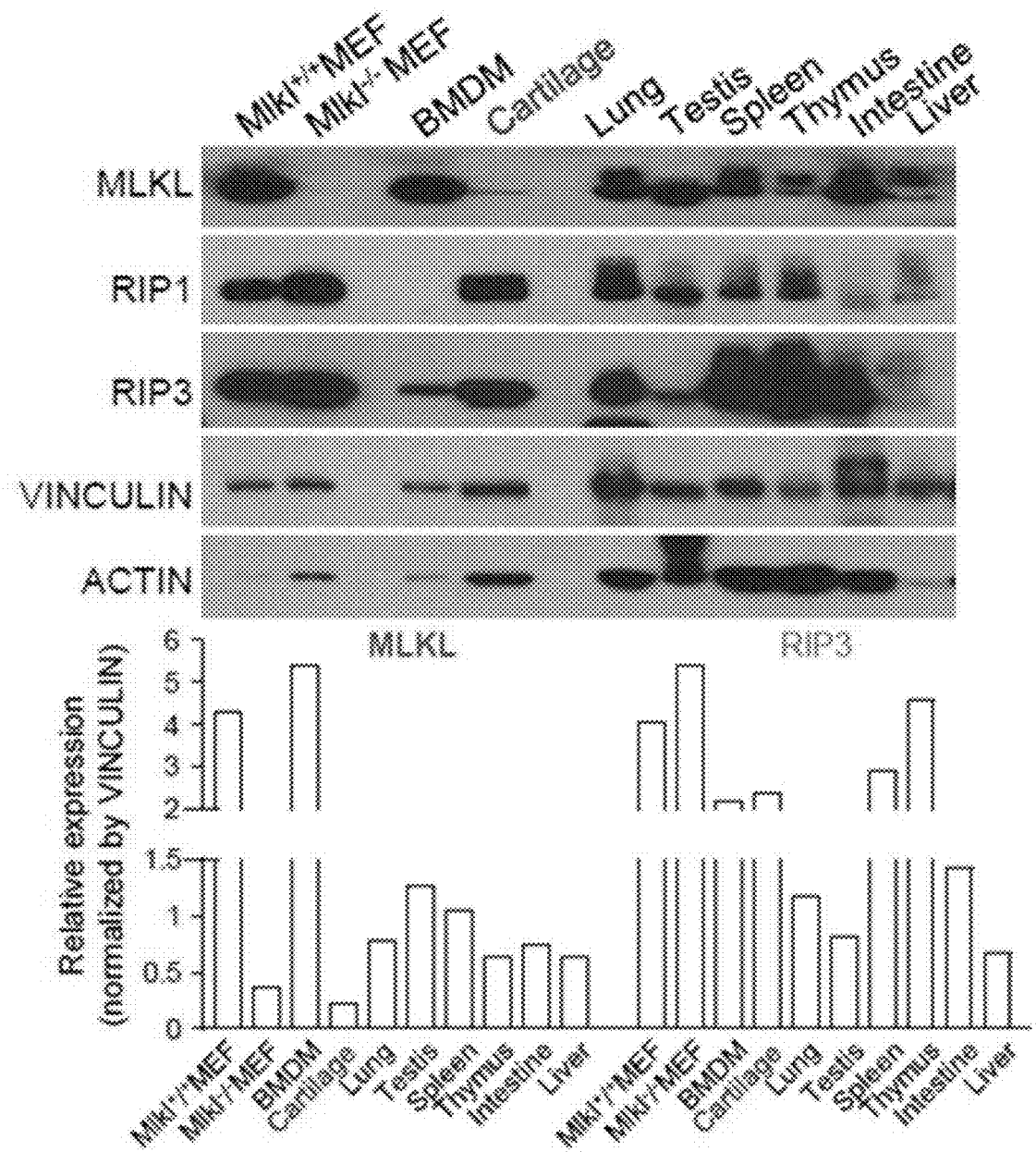
Figure 1C:
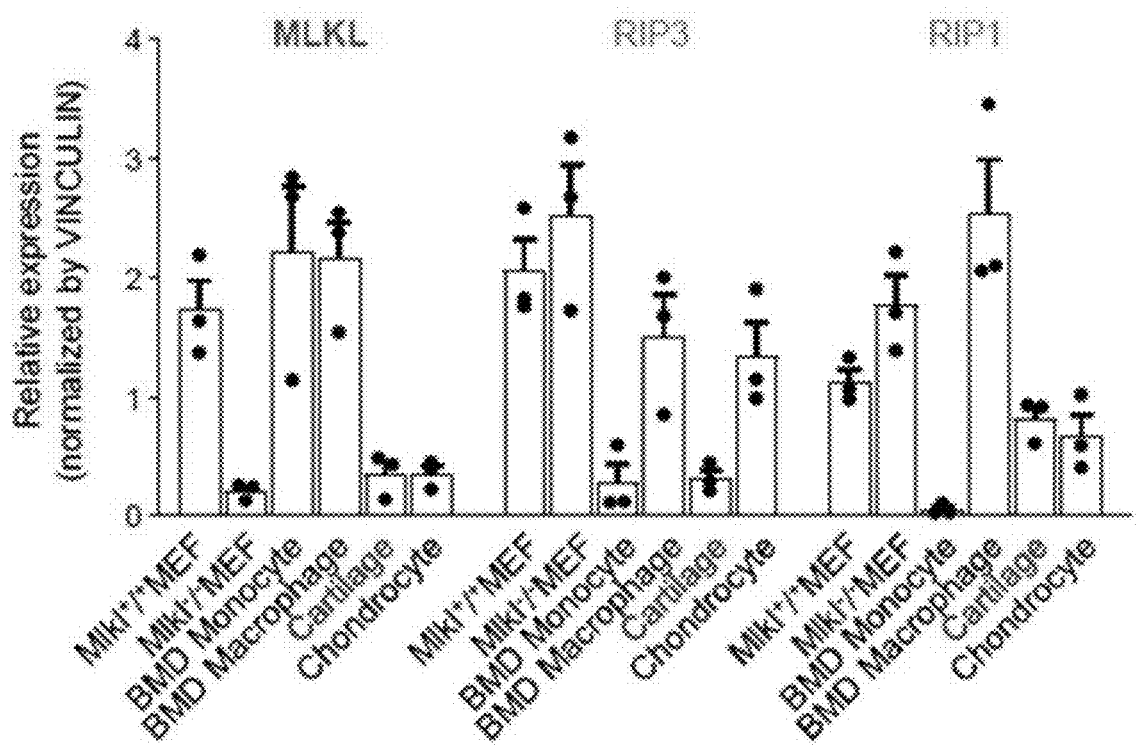
Figure 1D:
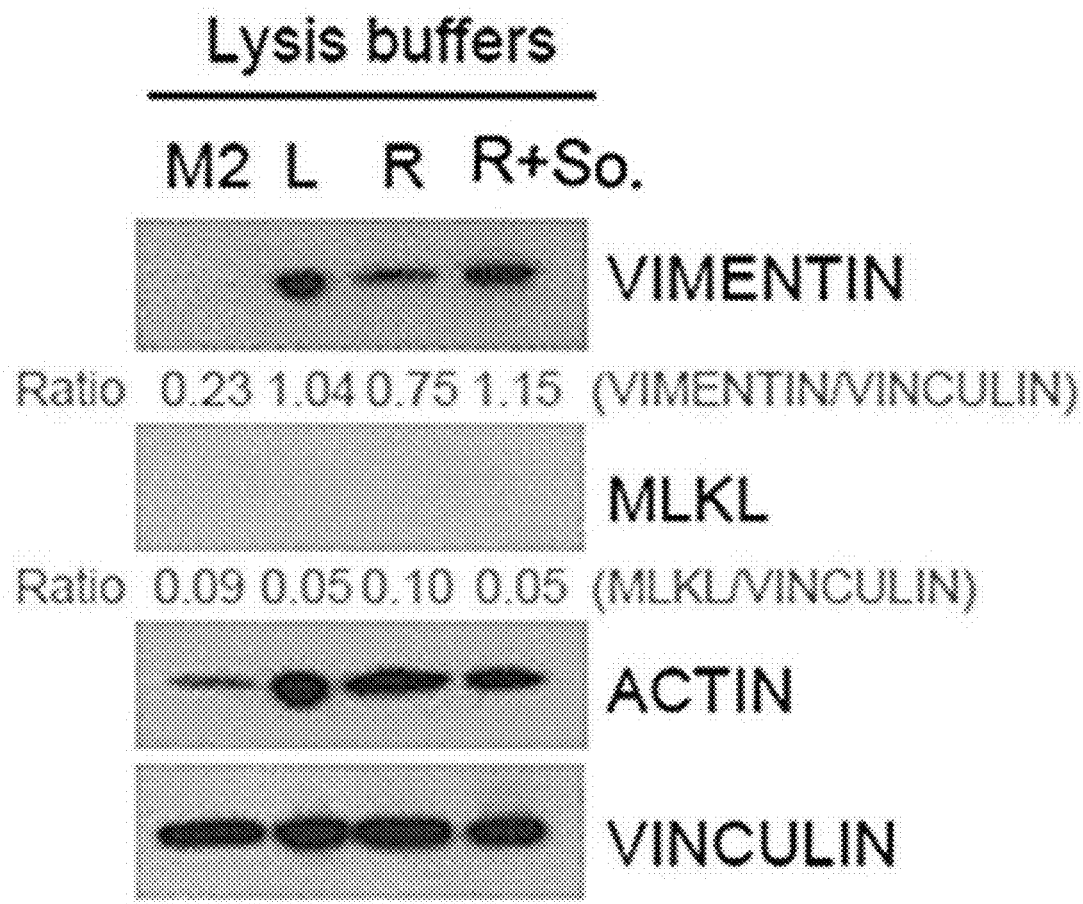
Figure 1E:
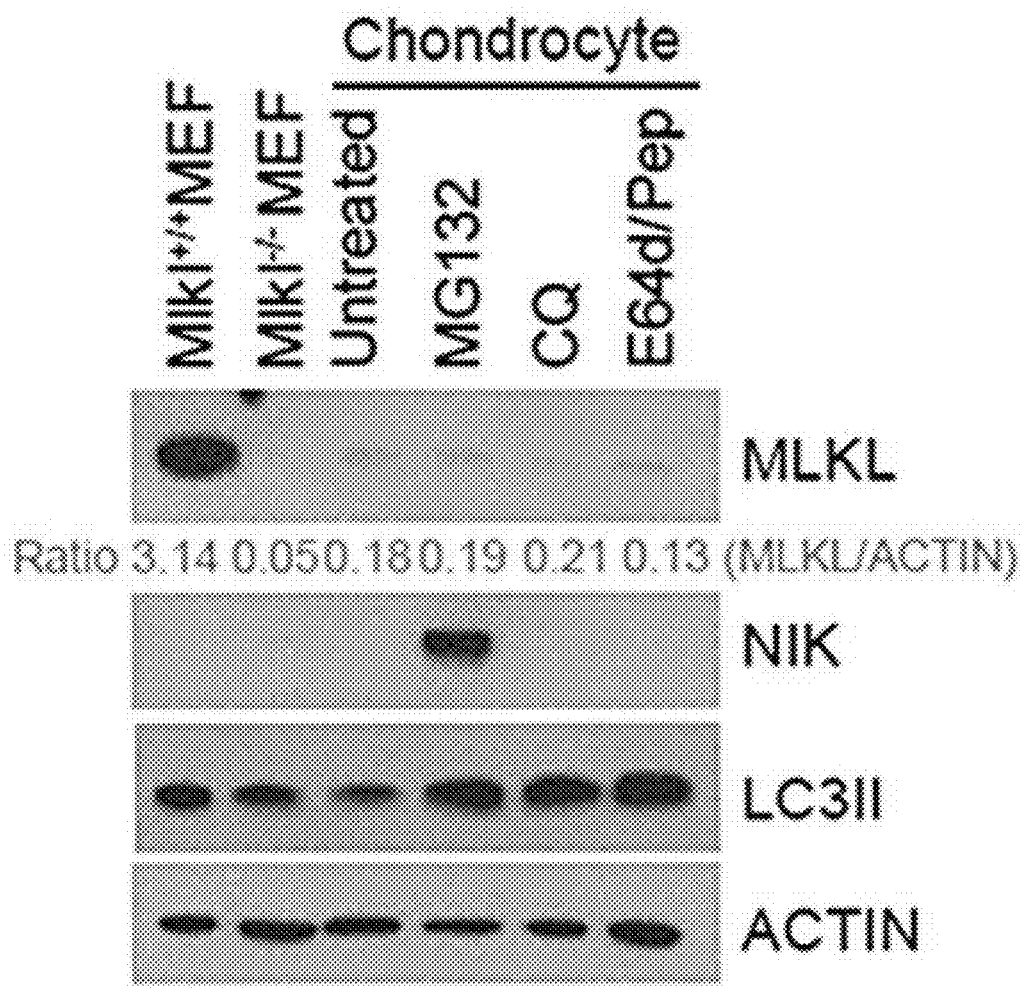
Figure 1F:
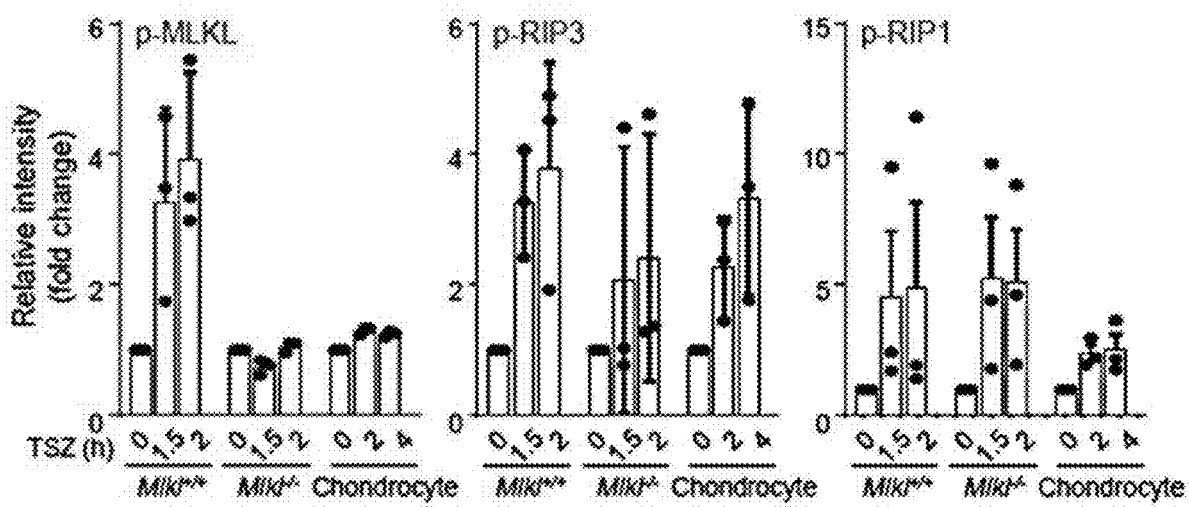
Figure 1G:
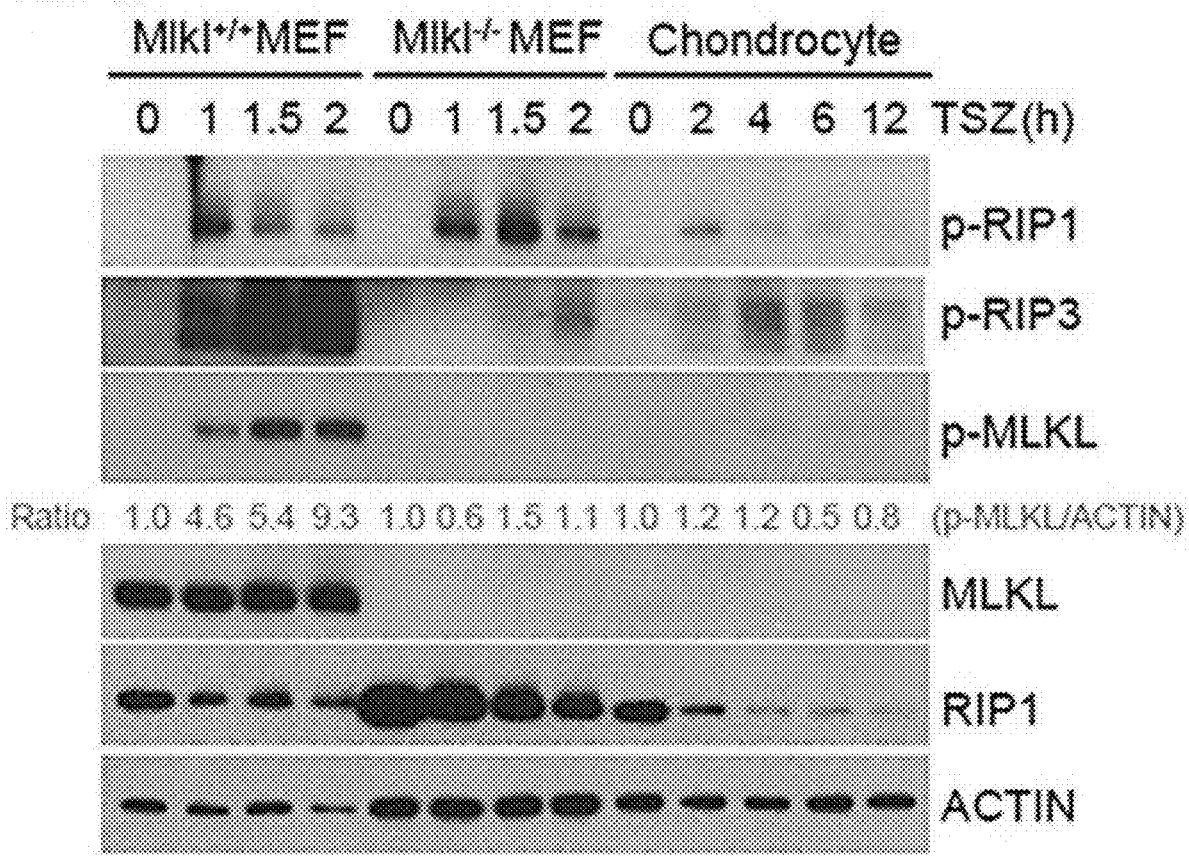
Figure 1H:
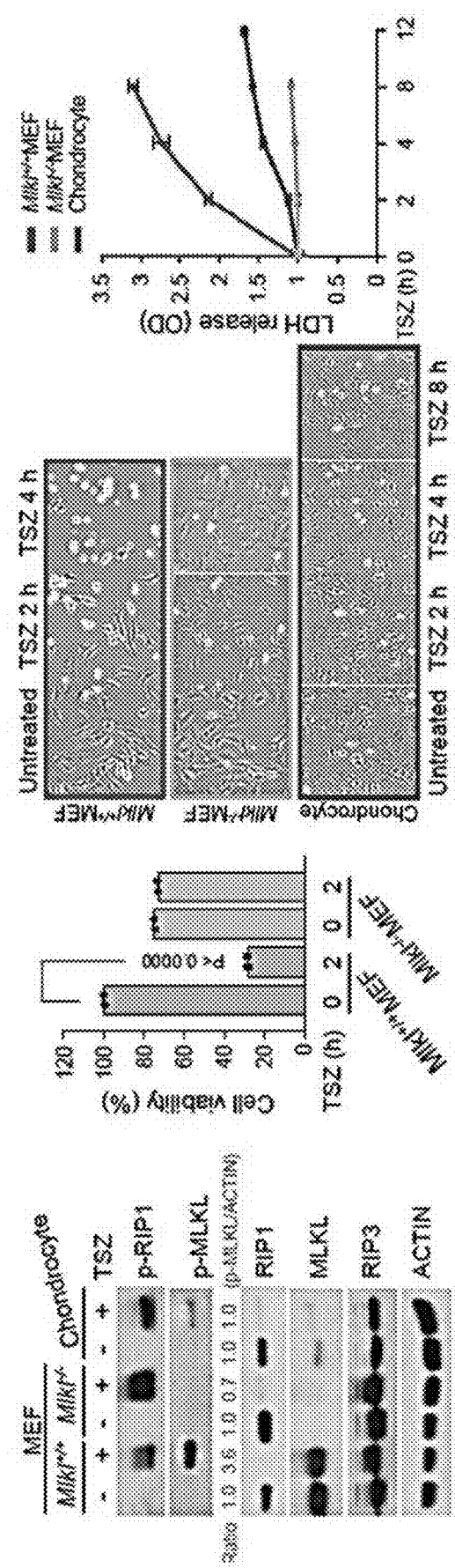
Figure 2A:
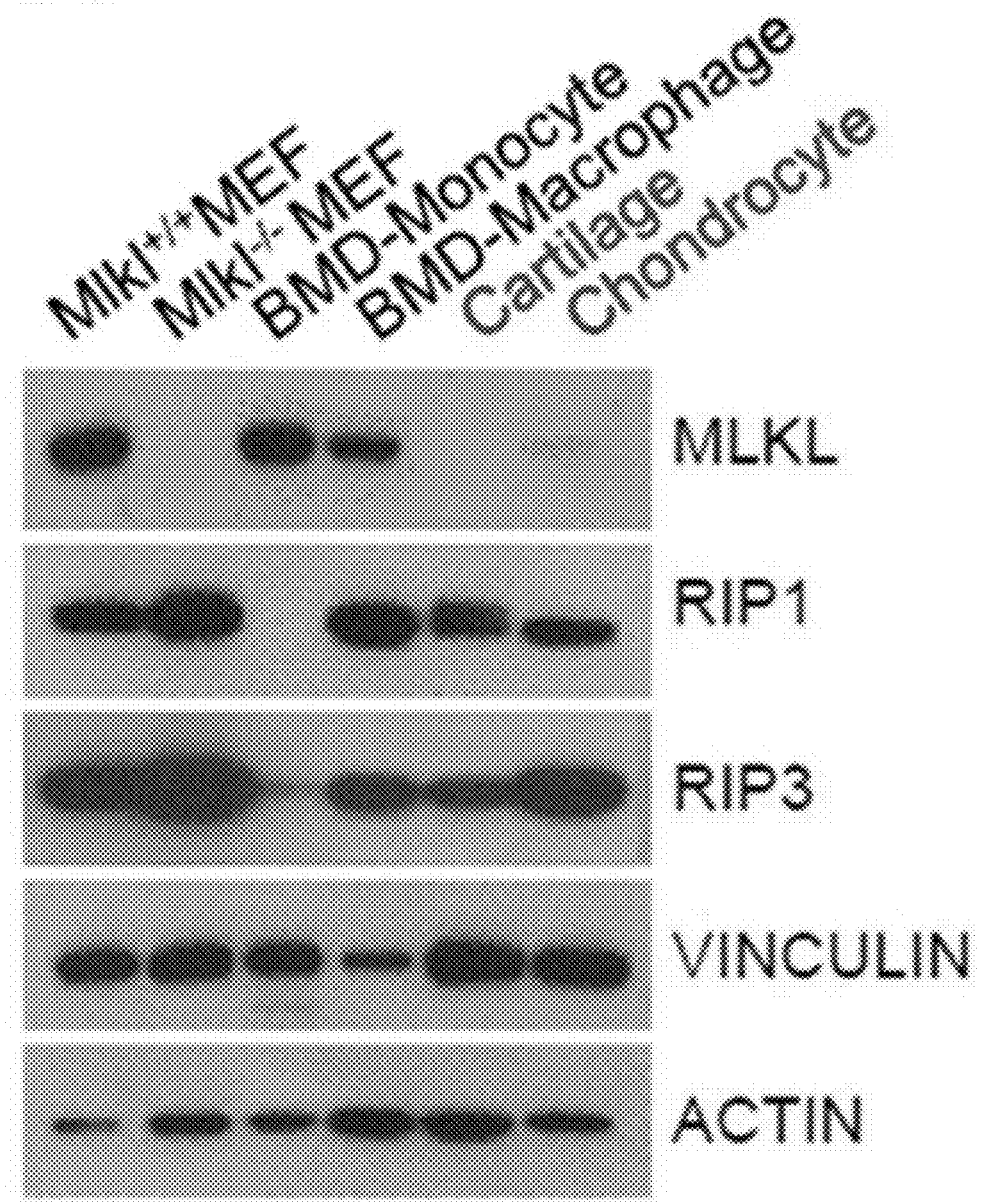
FIGS. 2A to 2F show that a non-canonical role of RIP3 in chondrocytes is associated with osteoarthritis pathogenesis.
Figure 2B:
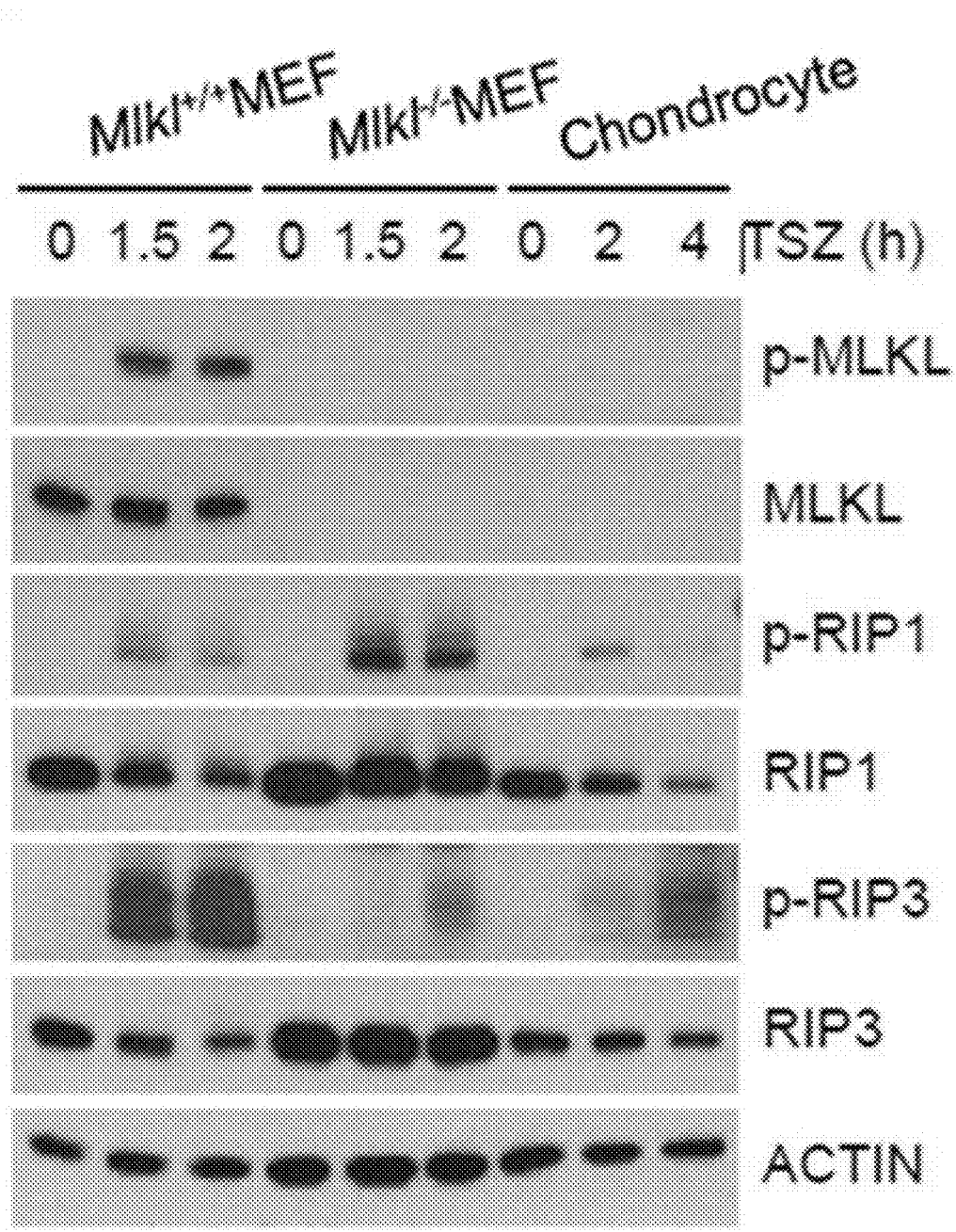

Example 2. Association Between RIP3 Overexpression-Mediated Gene Expression Pattern Change and Osteoarthritis In order to investigate the role of necroptosis in cartilage degeneration, RIP3 and MLKL expression patterns in various mouse tissue samples were measured. RIP3 expression did not differ significantly between tissues, but MLKL expression was extremely low in cartilage (FIGS. 1A and 1B) and in primary mouse articular chondrocytes which are the predominant cell type in cartilage (FIGS. 1C and 2A). Low MLKL expression was not due to protein insolubility, constitutive protein turnover, or protein stability, because proteasome (MG132) or lysosome (CQ, E64d/Pep A) inhibitors did not change the MLKL protein levels (FIGS. 1D and 1E). Necroptotic stimuli (TNFα+zVAD+SMAC mimetic: TSZ) may activate RIP3, which phosphorylates MLKL to induce necroptosis. After TSZ treatment, MLKL phosphorylation was strongly detected in mouse embryonic fibroblasts (MEFs) but not in chondrocytes (FIG. 2B; FIGS. 1F and 1G), whereas TNF failed to induce necroptosis in chondrocytes due to defective MLKL phosphorylation (FIG. 1H).

Figure 2C:
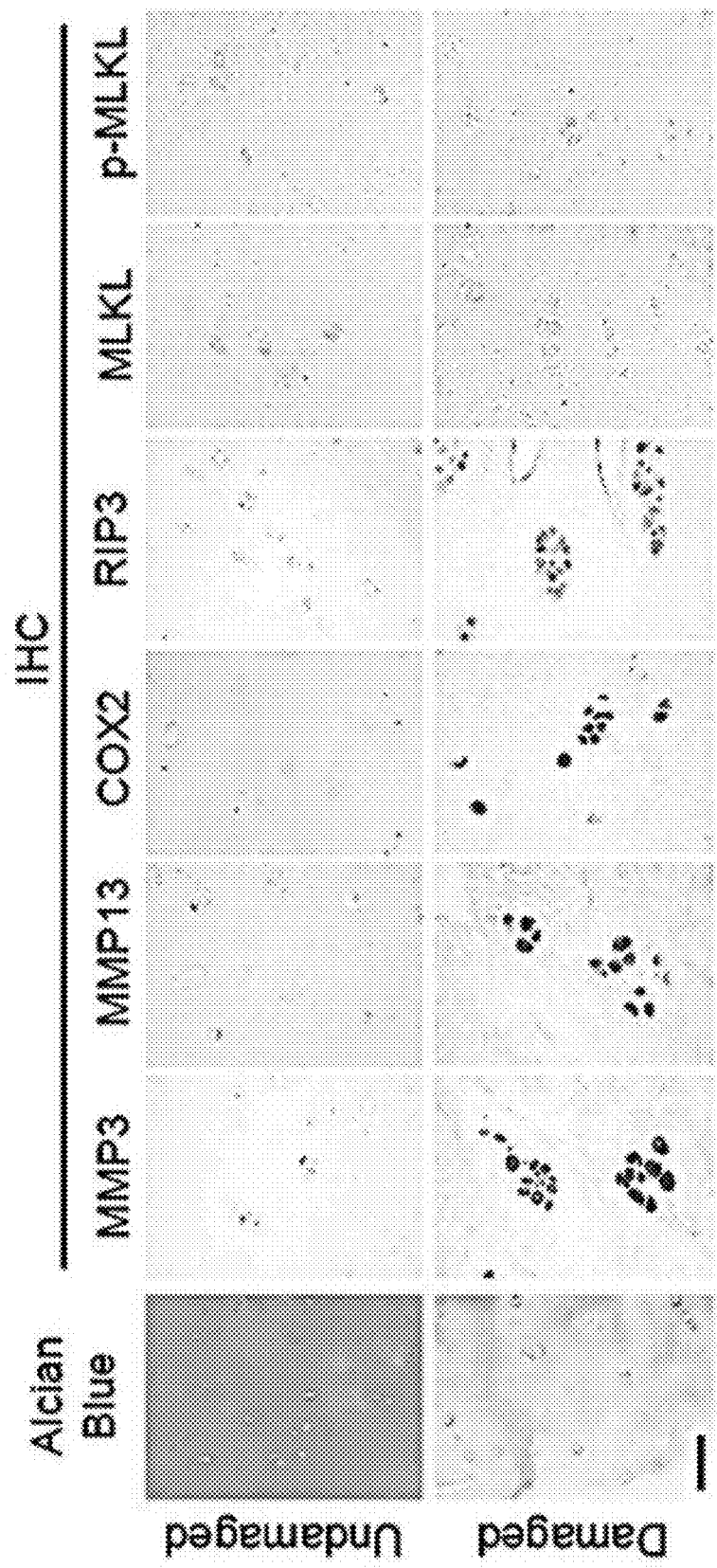
Figure 2D:
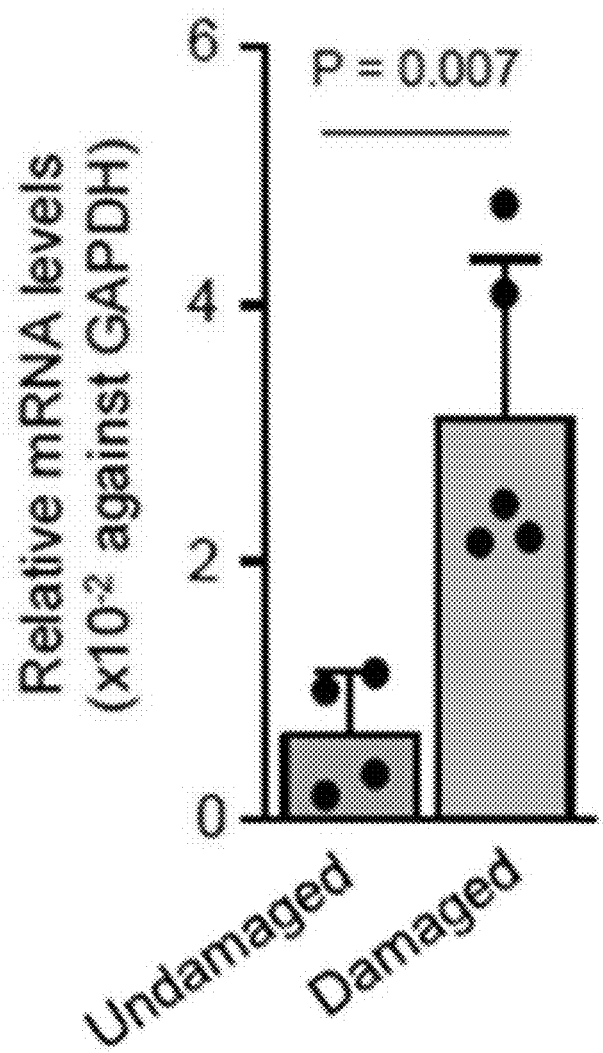
Figure 2E:
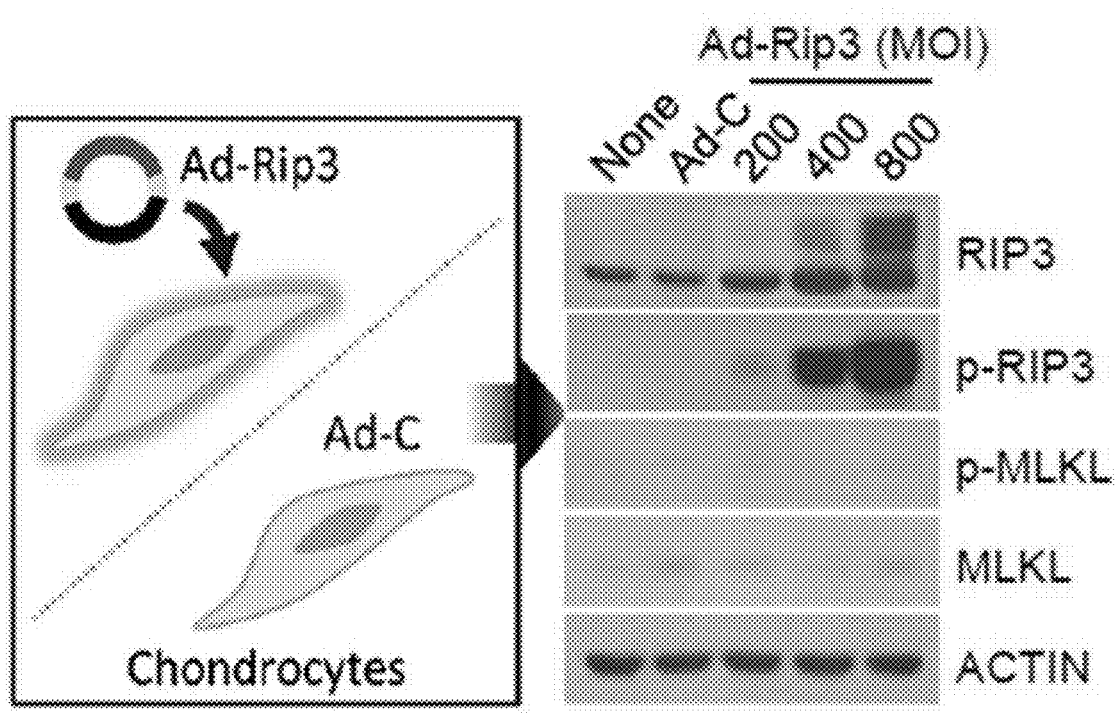
Figure 3A:
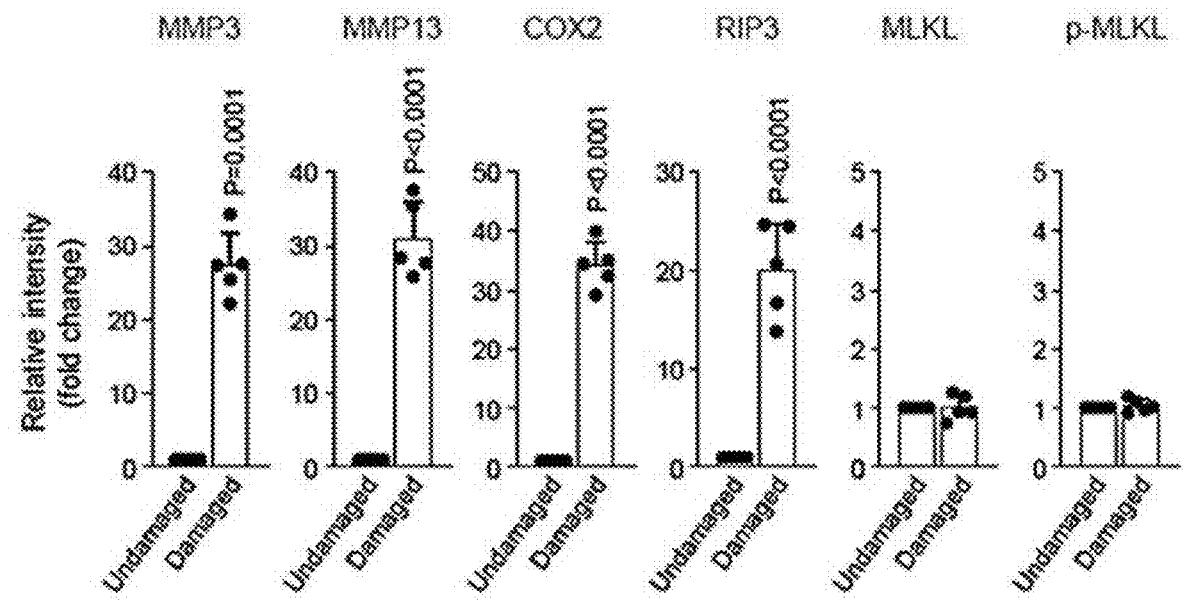
FIGS. 3A to 3E show that elevated RIP3 expression is correlated with osteoarthritis-pathogenesis-related gene expression patterns in chondrocytes.
Figure 3B:
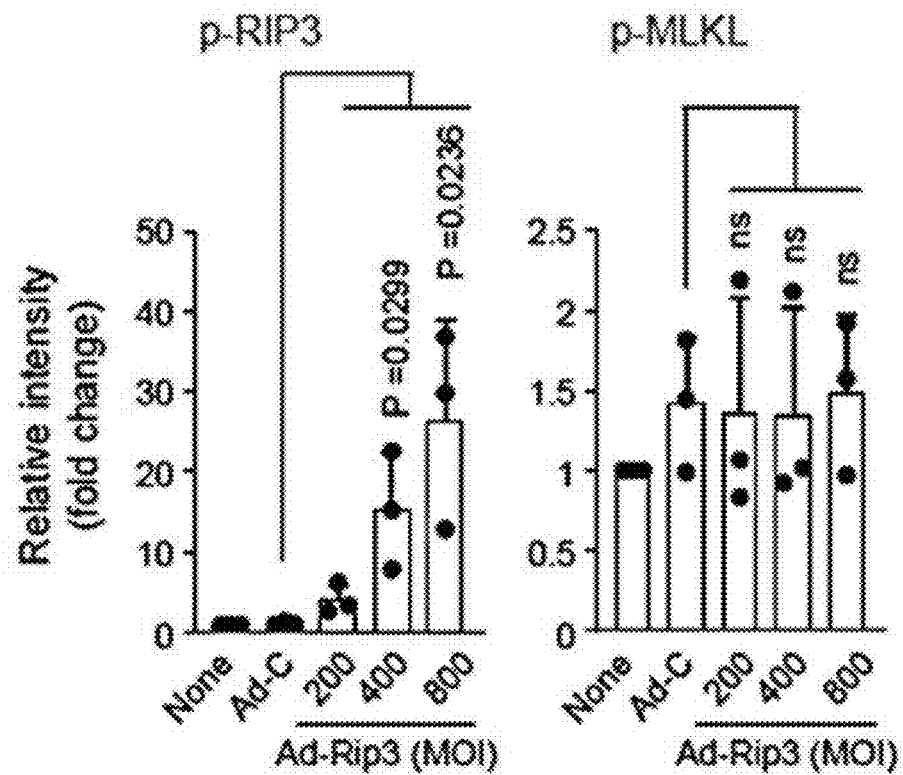
Figure 3C:
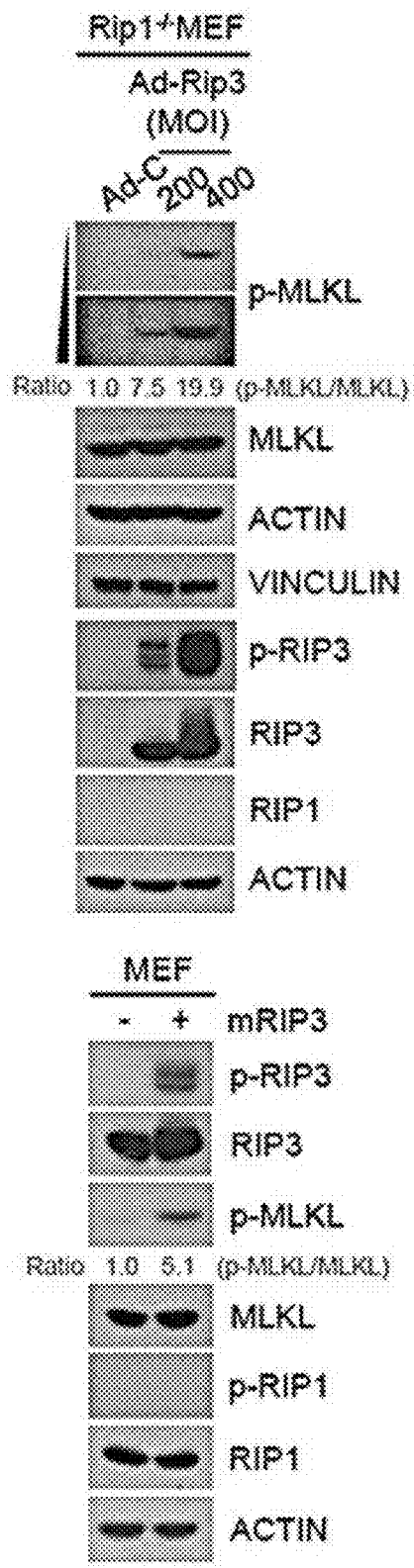

In order to explore the possible role of RIP3 in cartilage, the present inventors examined RIP3 expression in undamaged and damaged human osteoarthritis cartilage samples. RIP3 expression was significantly higher in damaged osteoarthritis cartilage than in undamaged samples (FIGS. 2C and 2D; FIG. 3A), whereas MLKL and p-MLKL expression did not differ, and was undetectable. Next, the present inventors ectopically expressed RIP3 in Ad-Rip3-infected primary mouse articular chondrocytes. RIP3 overexpression did not cause MLKL phosphorylation capable of inducing necroptosis (FIG. 2E; FIG. 3B). Therefore, RIP3 overexpression in osteoarthritis pathogenesis may be distinct from canonical necroptosis-dependent functions thereof. It is known that upregulated RIP3 expression leads to RIP1-independent necroptosis through MLKL phosphorylation. For testing thereof, RIP3 was overexpressed in RIP1-deficient MEFs, showing that RIP3 activation is sufficient to trigger downstream events. Upregulated RIP3 expression potentiated MLKL phosphorylation in the absence of RIP1 phosphorylation, suggesting that the role of RIP3 in osteoarthritis development is unlikely to be necroptosis-independent (FIG. 3C).

Figure 3D:
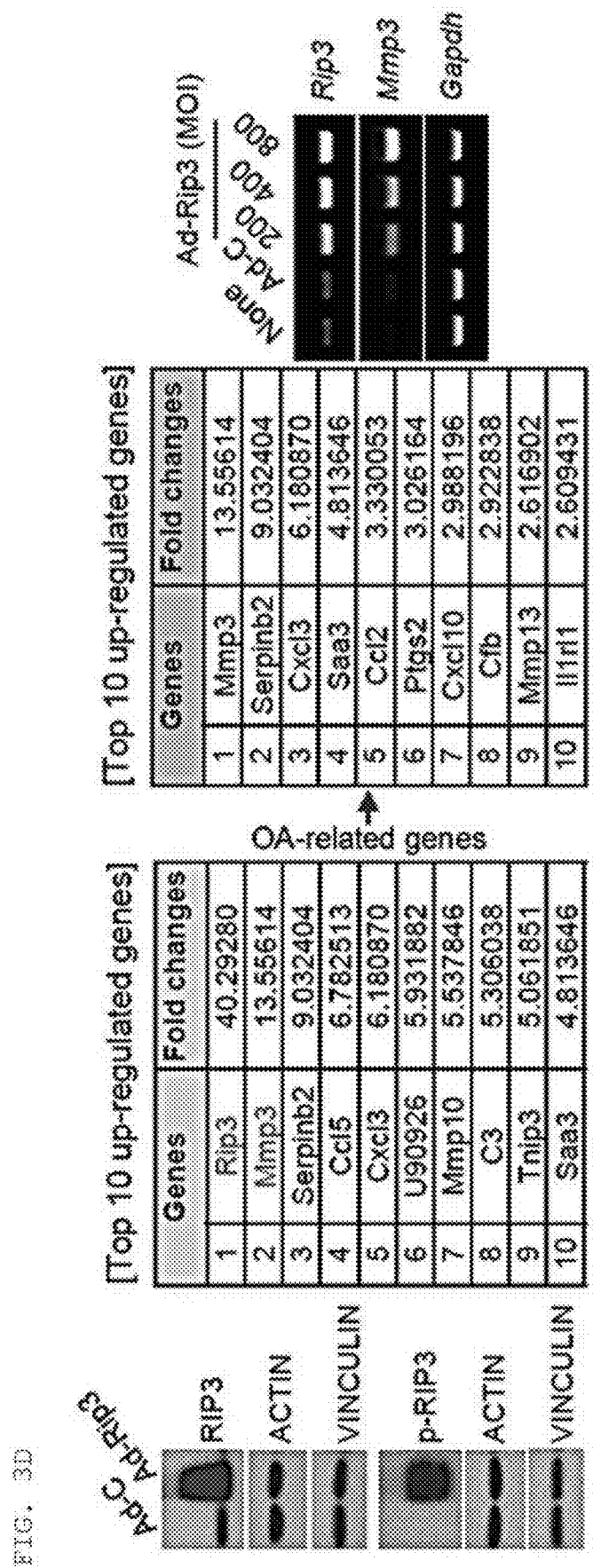
Figure 3E:
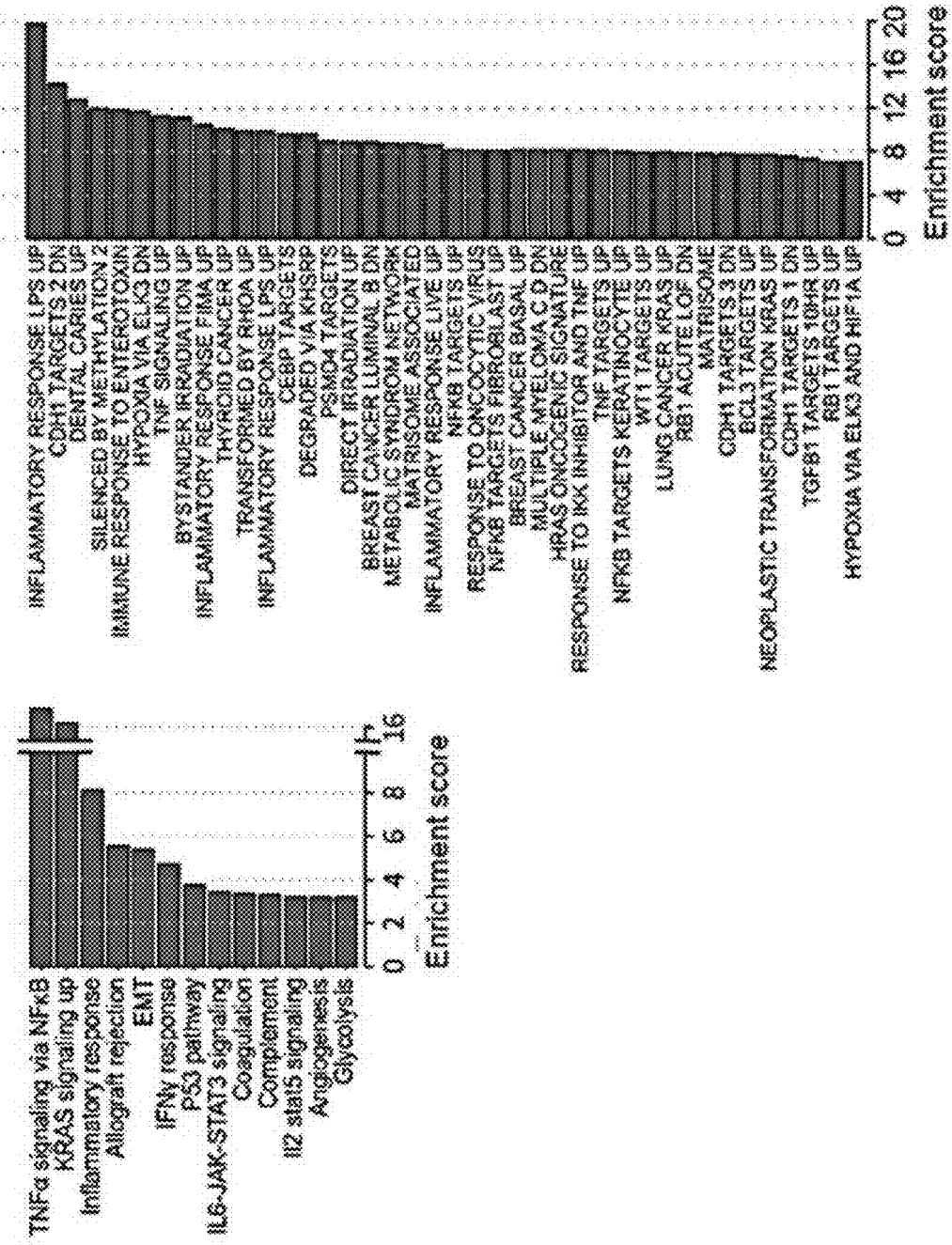

Next, the present inventors performed genome-wide expression profiling using microarrays to investigate transcriptomic changes in Ad-Rip3-infected chondrocytes. RIP3 overexpression increased the expression of catabolic factor-matrix metalloproteinase 3 (Mmp3), which plays a key role in osteoarthritis pathogenesis, inflammation, MMP activation, and ECM degradation (FIG. 3D). Functional enhancement analysis revealed that RIP3 overexpression-induced genes are involved in TNFα signaling and inflammation (FIG. 3E).

Figure 2F:
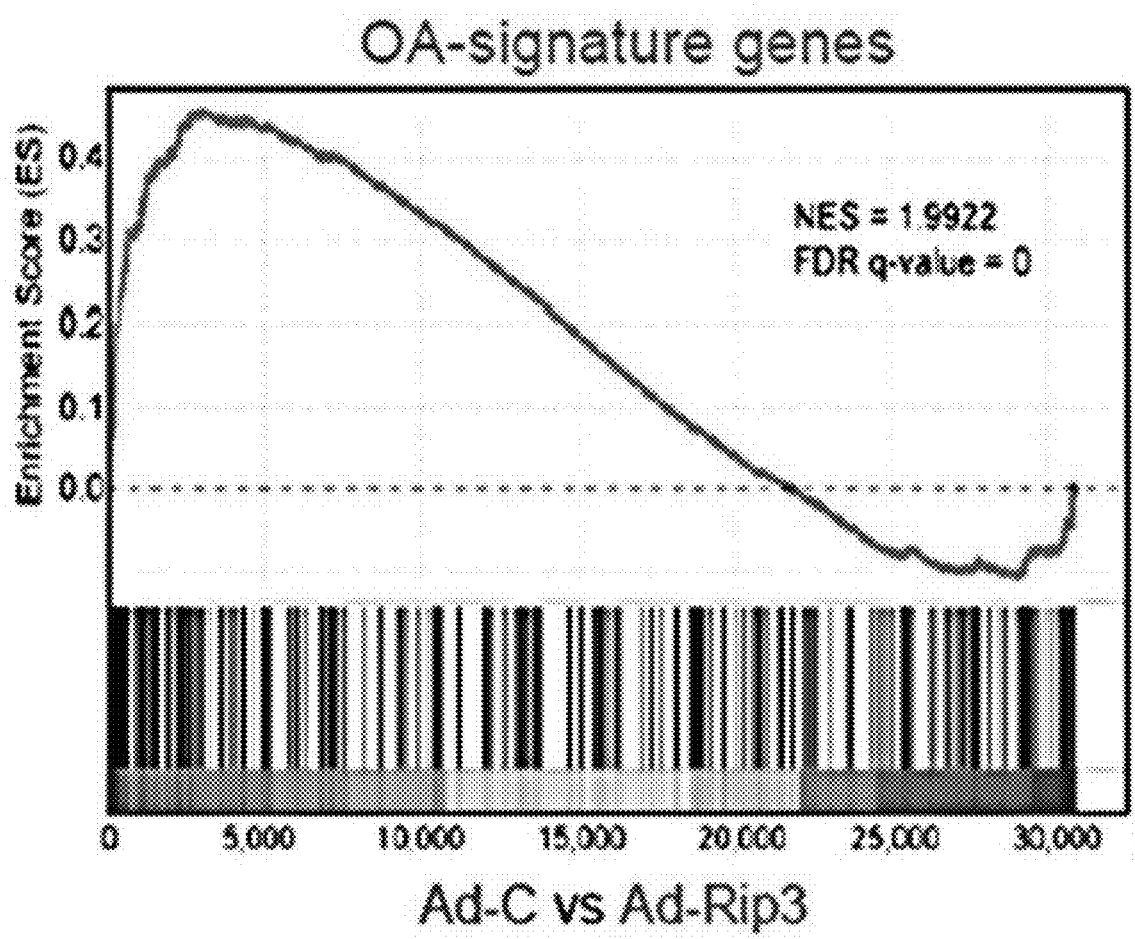
Figure 4A:
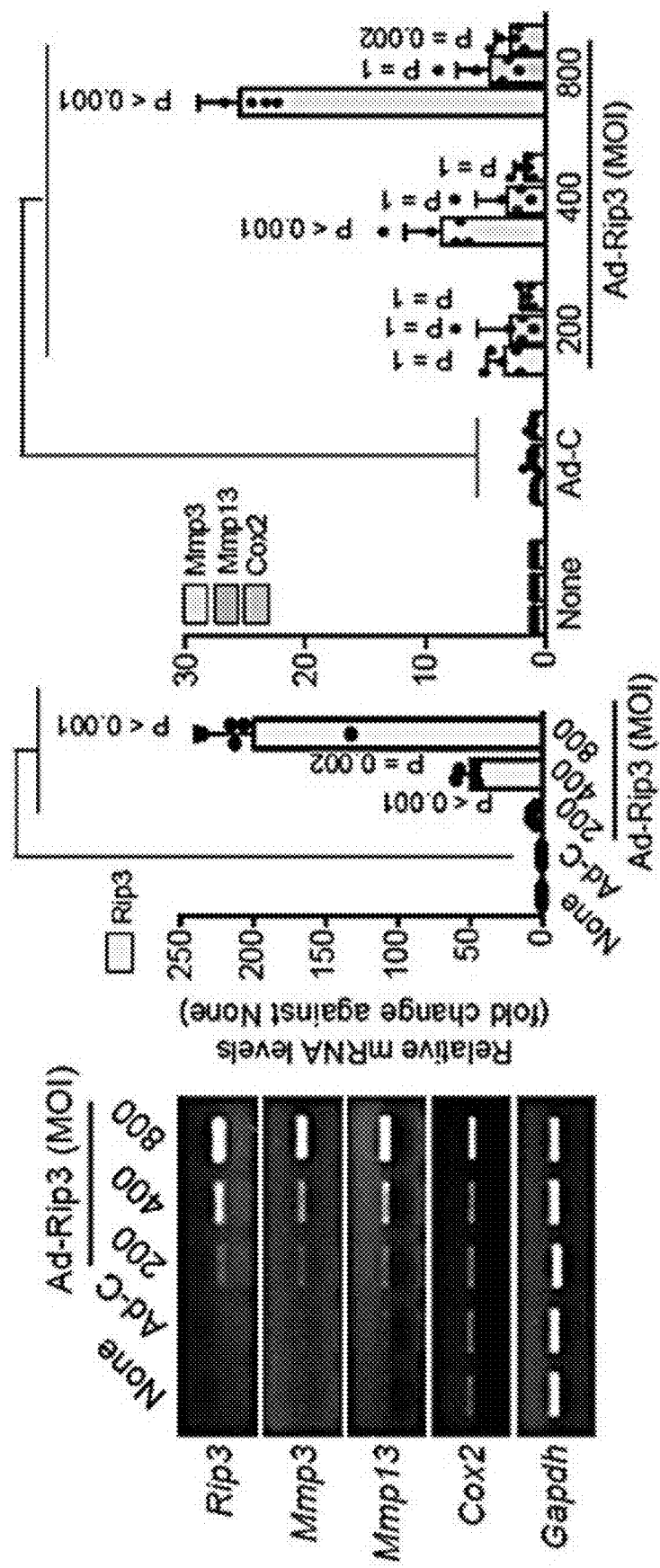
FIGS. 4A to 4F show that modulation of RIP3 expression is correlated with osteoarthritis.
Figure 4B:
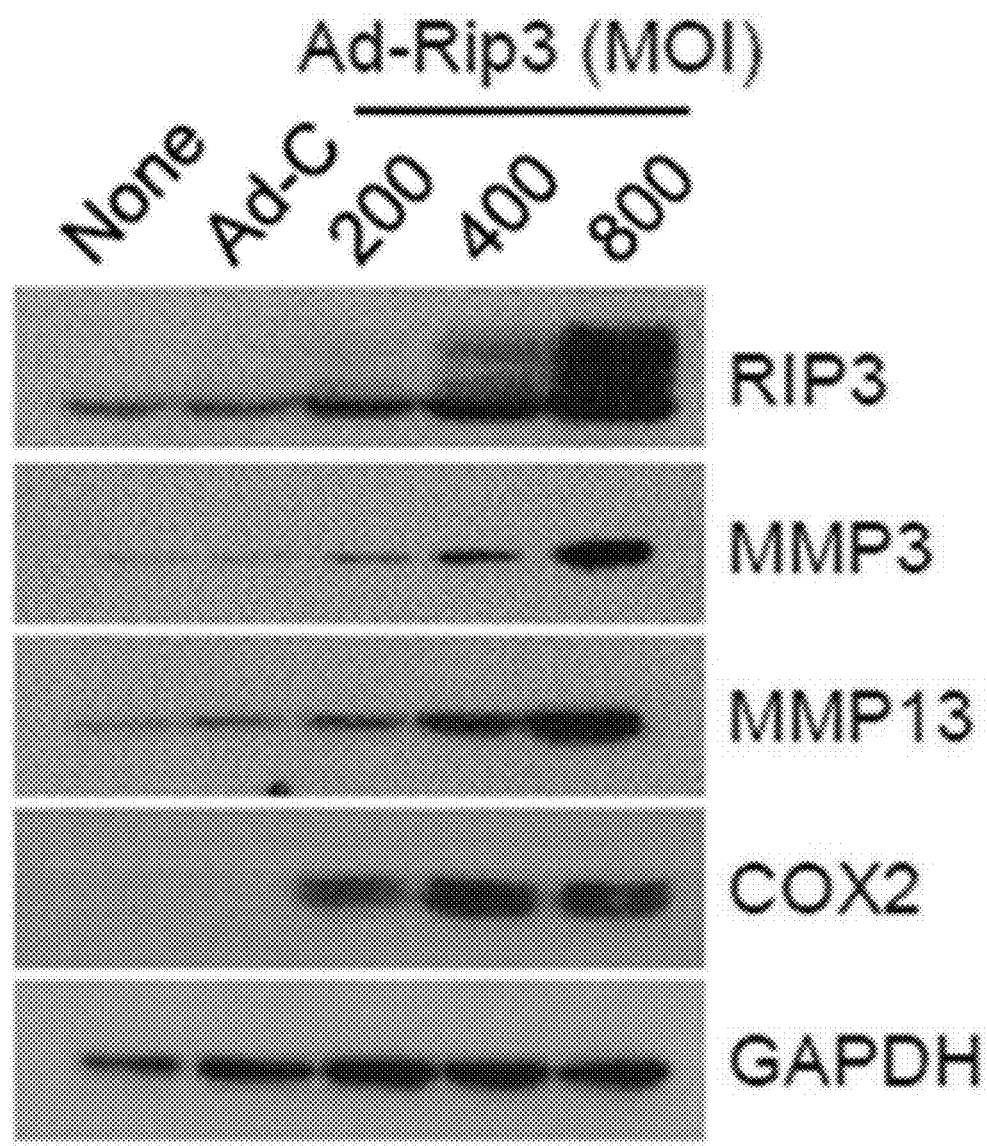
Figure 4C:
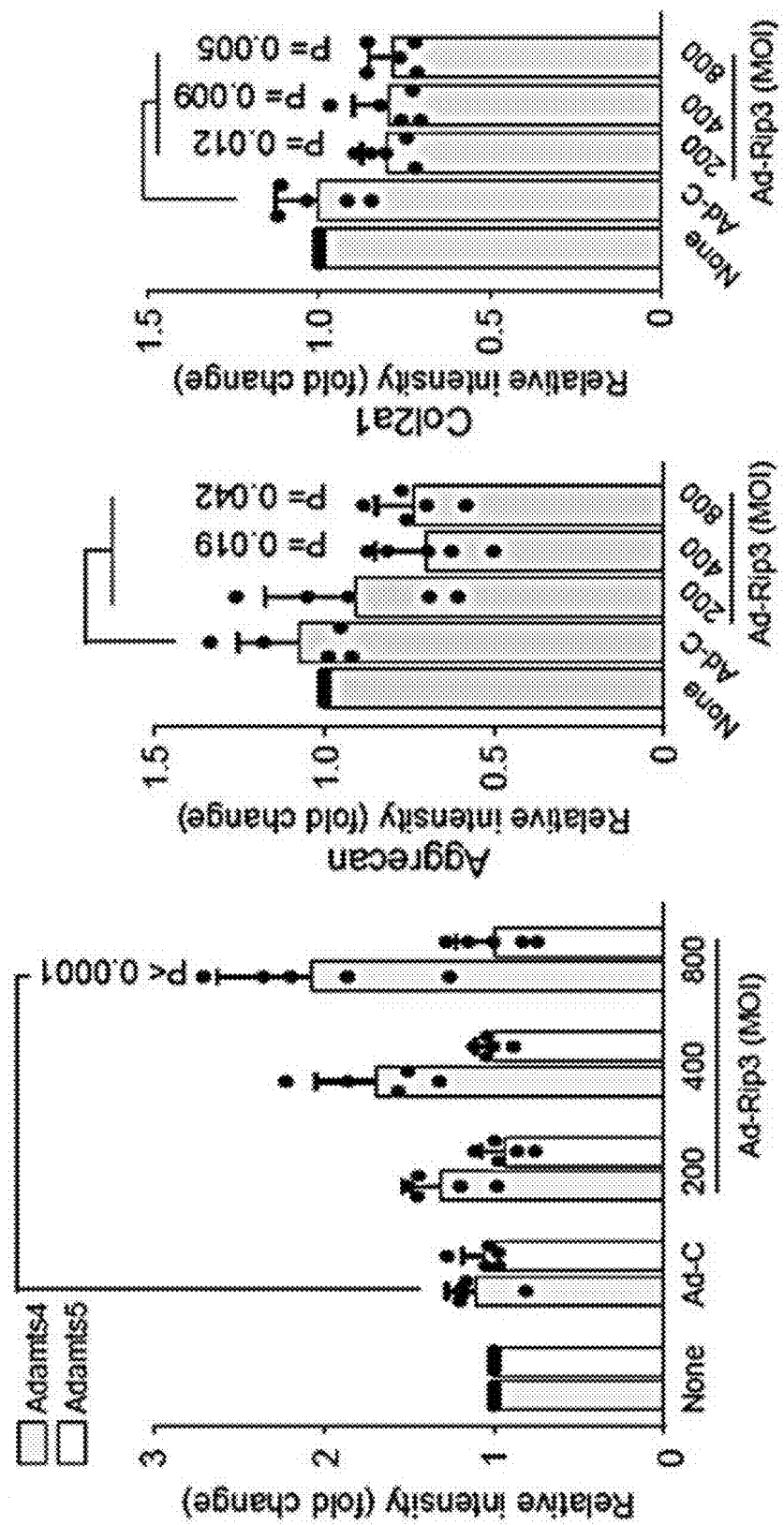
Figure 4D:
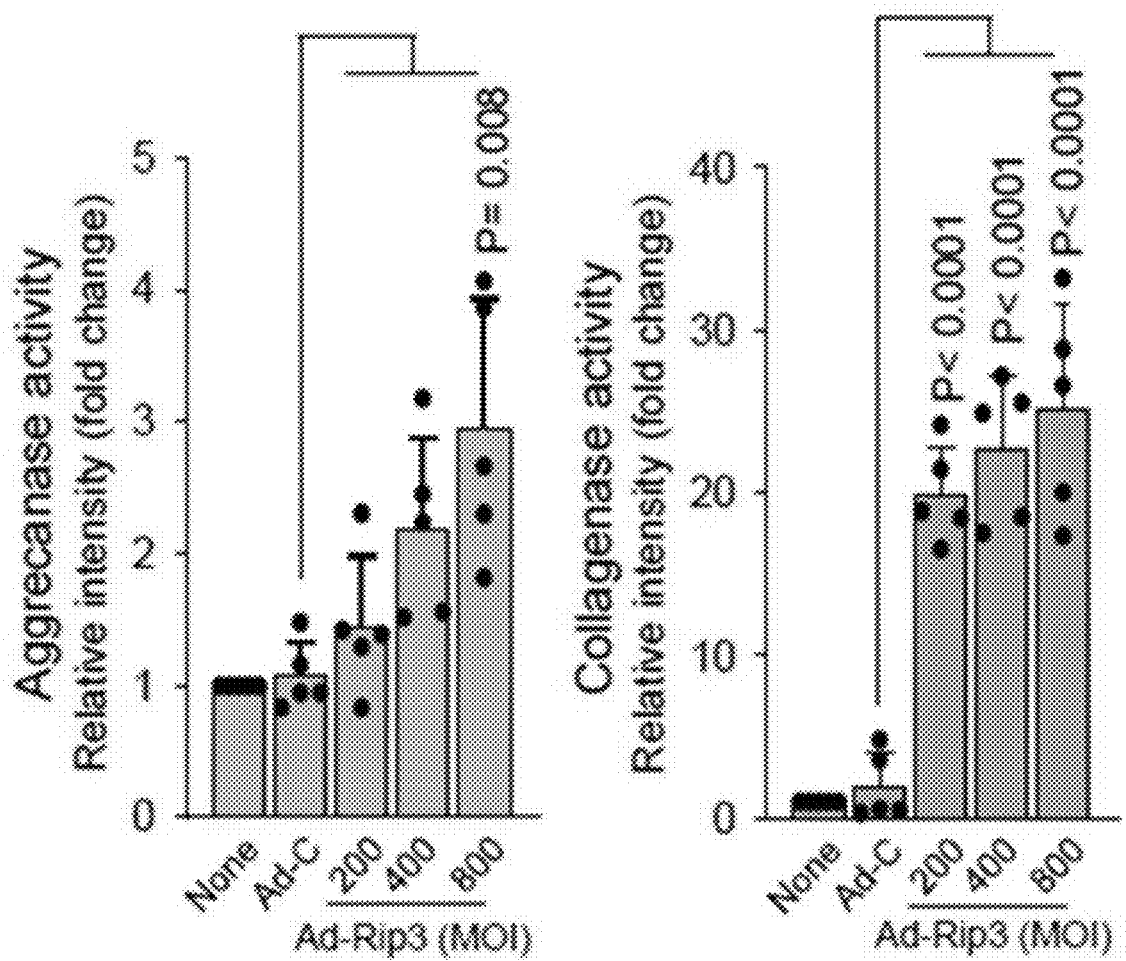
Figure 4E:
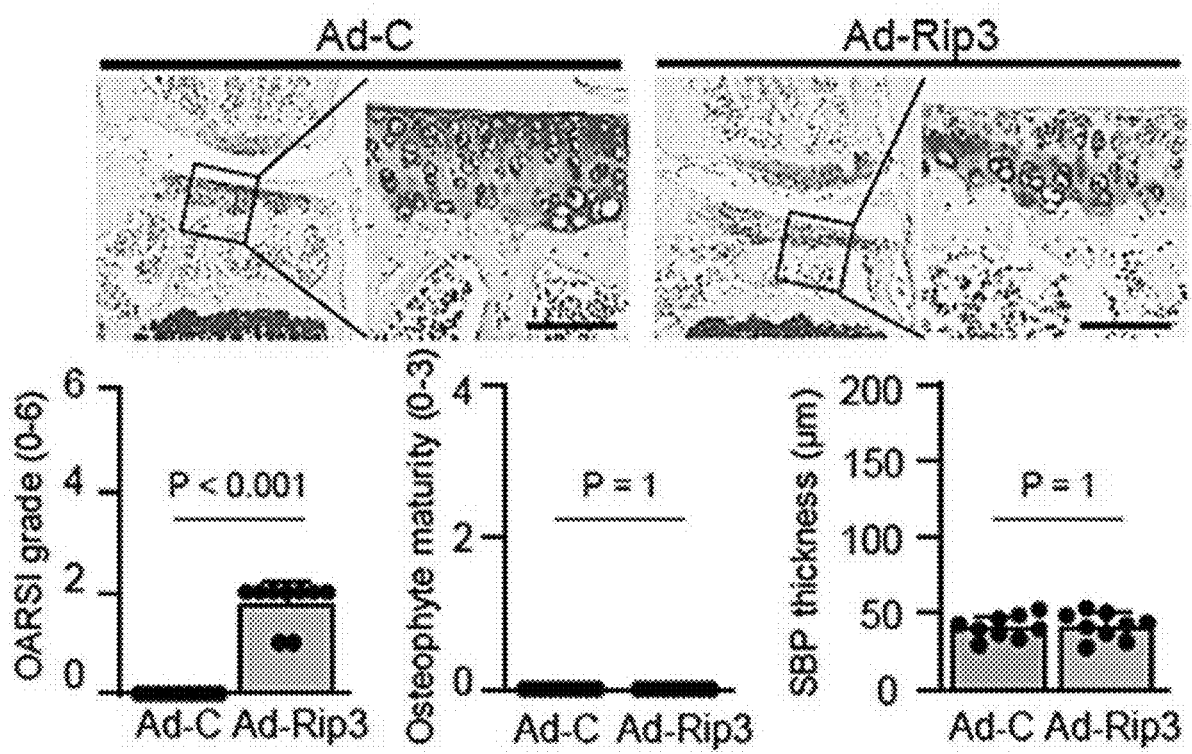
Figure 4F:
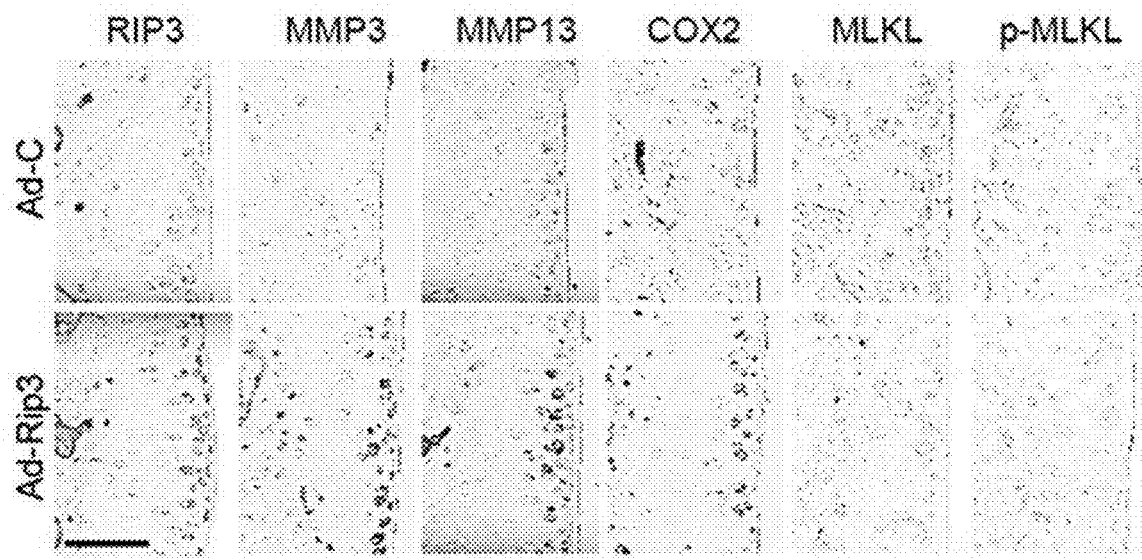
Figure 5A:
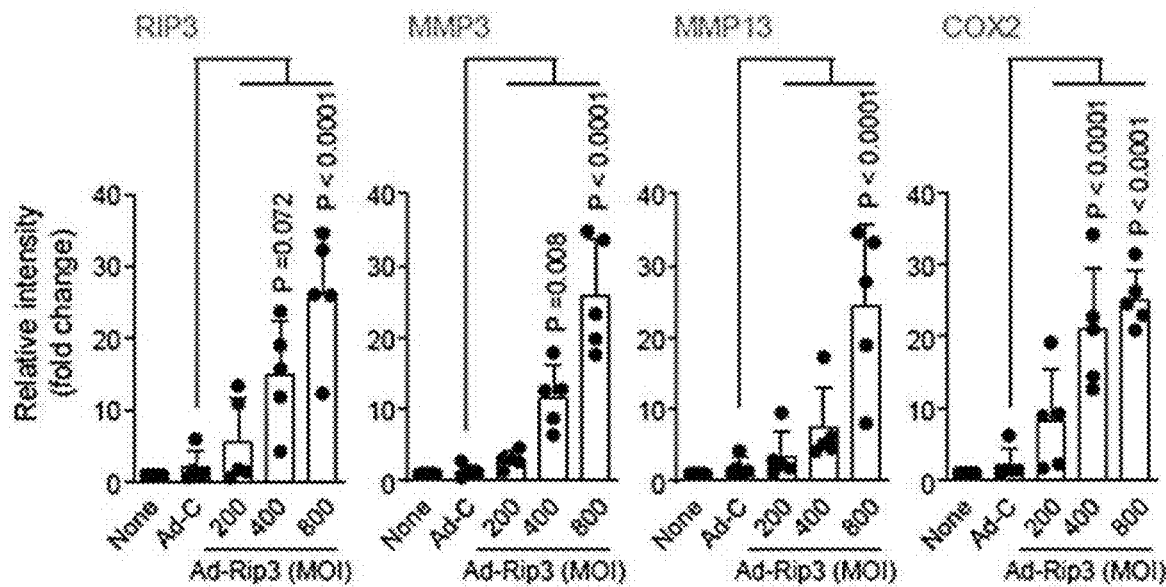
FIGS. 5A to 5G show that elevated RIP3 expression does not induce chondrocyte death.
Figure 5B:
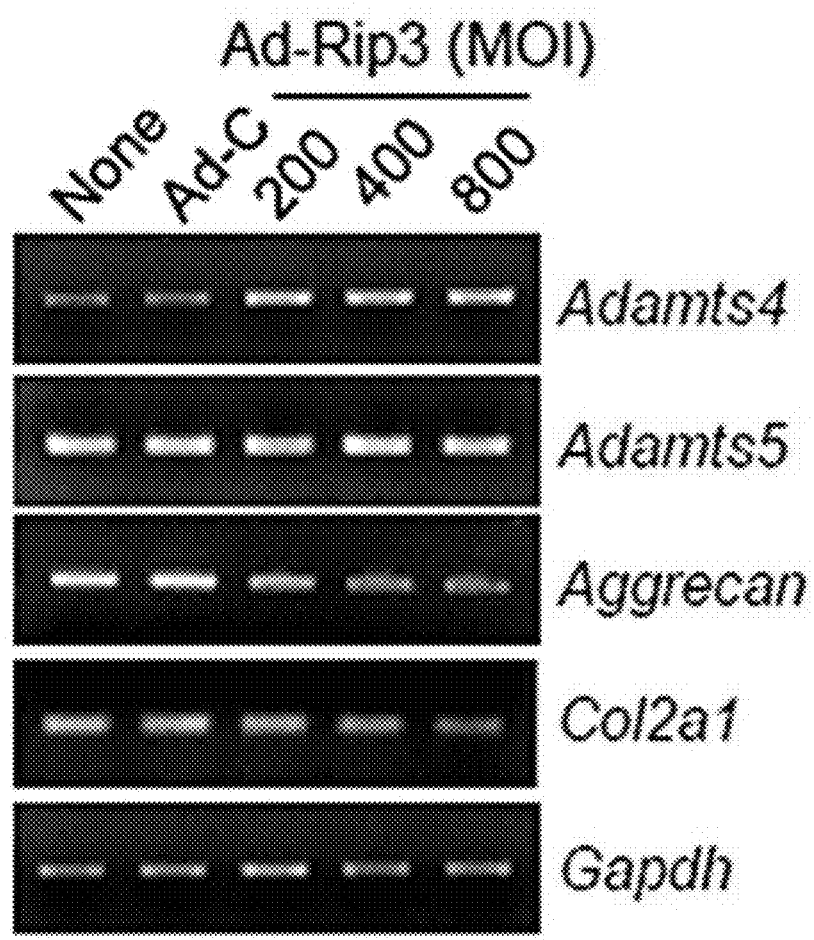
Figure 5C:
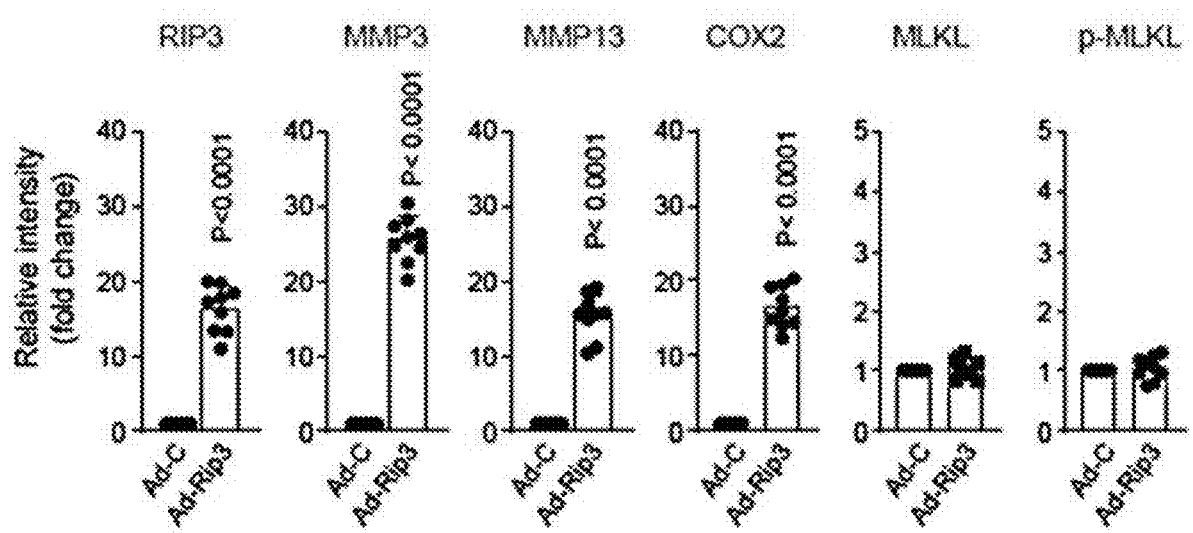
Figure 5D:
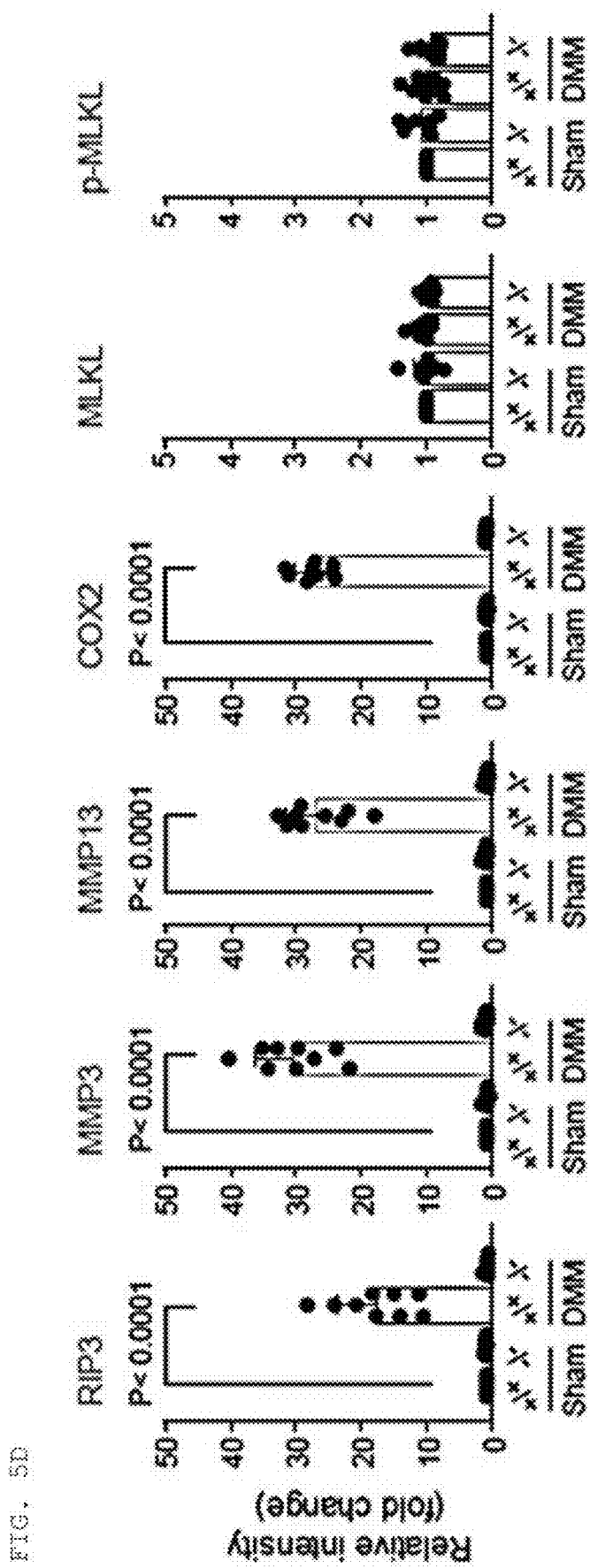
Figure 6A:
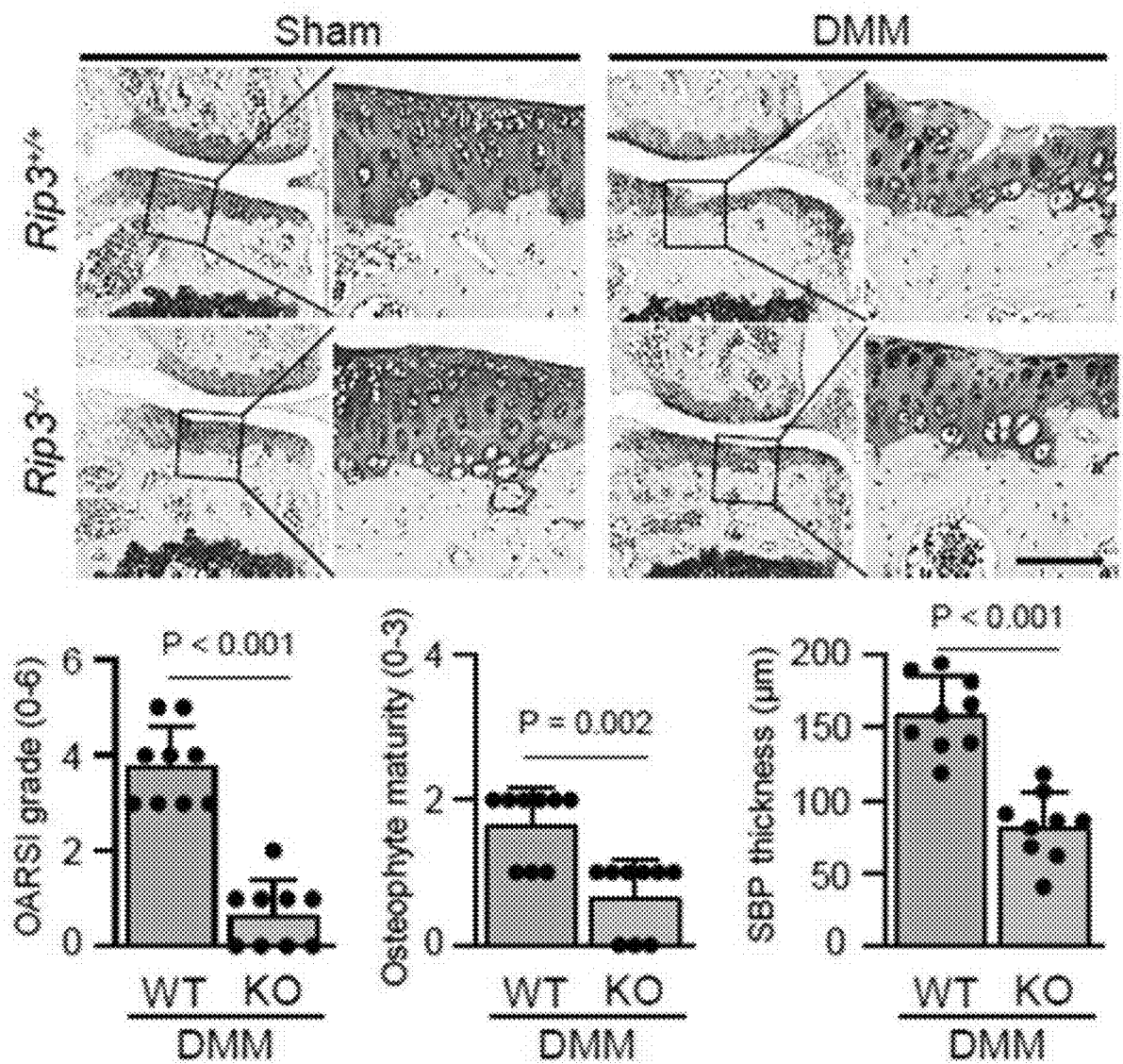
FIGS. 6A and 6B show reduced osteoarthritis pathogenesis in Rip3 knockout mice, in which WT and Rip3 knockout mice were subjected to DMM surgery (n=9).
Figure 6B:
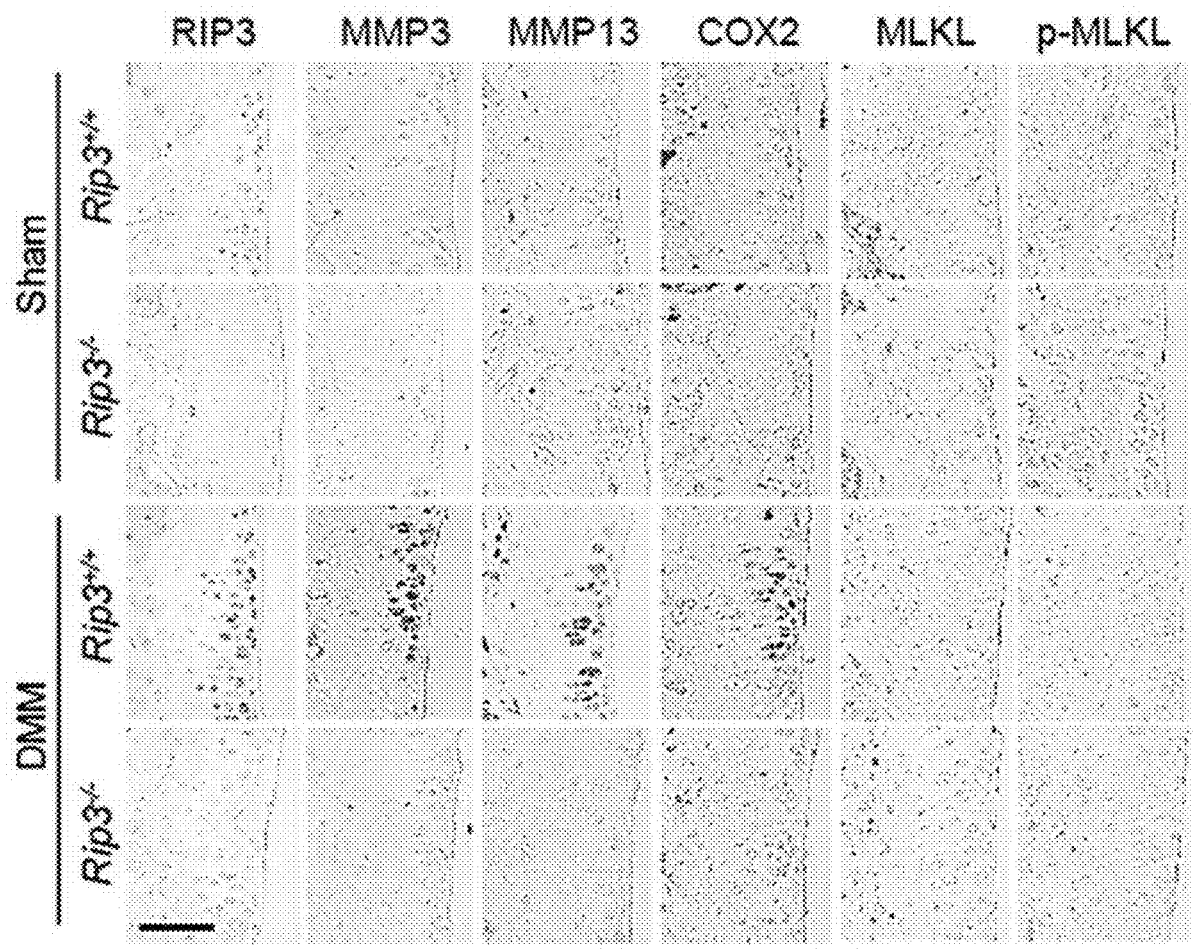

In order to further evaluate RIP3-induced gene expression, expression of 150 upregulated and 71 downregulated genes in osteoarthritis cartilage by GSEA was investigated (Table 3), indicating that the osteoarthritis signature genes were upregulated in RIP3-overexpressing chondrocytes (FIG. 2F).

sion in cartilage and increased the expression of MMP3. MMP13 and COX2 (FIG. 4F and FIG. 5C). In order to verify these effects. DMM-induced osteoarthritis models, which were most suitable for the development of human osteoarthritis in Rip3-deficient mice, were established. Cartilage destruction, osteoarthritis manifestation, and catabolic factor expression were significantly reduced in these mice compared to WT mice (FIGS. 6A and 6B; FIG. 5D). Consistent with RIP3 upregulation in human osteoarthritic cartilage.

TABLE 3

| Genes upregulated in osteoarthritic cartilage (150 genes) | | | | | | |
|---|---|---|---|---|---|---|
| 3830406C13Rik | Cdkn2b | Ebf3 | Hey2 | Mtss1 | Rab23 | Tgfbi |
| Abracl | Cdkn3 | Egr2 | Hhipl1 | Ncapg | Rcan1 | Tmem100 |
| Adamts14 | Cenpf | Epha3 | Hmga2 | Nedd4l | Rhbdl2 | Tmem119 |
| Adamts5 | Cenpk | Eva1a | Homer2 | Nedd9 | S100a4 | Tmem200a |
| Adamts6 | Cep55 | Evi2a | Hunk | Ngf | Sema3c | Tmem59l |
| Adgrg1 | Chst13 | Fam132b | Ier3 | Nt5e | Serpine1 | Tnfaip6 |
| Adtrp | Cited4 | Fam167a | Iqgap3 | Ntf3 | Serpine2 | Tnfrsf12a |
| AI661453 | Ckb | Fam60a | Itga3 | Ociad2 | Sgk1 | Tom1l1 |
| Akr1c20 | Clic3 | Fat3 | Kcne4 | Ogn | Sik1 | Top2a |
| Anln | Col13a1 | Fgf9 | Kcnn4 | Osbpl3 | Slc2a5 | Trim36 |
| Arhgap44 | Col18a1 | Fhl2 | Kcns3 | P3h2 | Slc38a5 | Uroc1 |
| Arl4a | Col1a1 | Foxf1 | Kif20a | Pamr1 | Slc6a6 | Vcan |
| Arntl2 | Col7a1 | Fstl3 | Lamb3 | Pcdh10 | Slitrk6 | Veph1 |
| Aspm | Cpeb2 | Fzd10 | Lif | Pcdh18 | Sntb1 | Vwc2 |
| Aspn | Csdc2 | Galnt7 | Lmo2 | Pgm2l1 | Sqrdl | Wisp1 |
| Atrnl1 | D330045A20Rik | Gja1 | Lrrc8c | Plaur | St6galnac5 | Wnt5a |
| B3gnt2 | Diras1 | Gjb2 | Lrrc8e | Plekhg1 | Stx1a | Zfp365 |
| B3gnt5 | Dkk3 | Glis3 | Lum | Popdc3 | Syt11 | Zfp367 |
| Bmpr1b | Dnajc12 | Glrb | Map1b | Postn | Sytl2 | |
| C1galt1 | Dner | Gmnn | Mob3b | Prex2 | Tbx3 | |
| Car12 | Dsg2 | Gpc4 | Moxd1 | Ptges | Tenm3 | |
| Cdk1 | Dusp4 | Gria2 | Msx2 | R3hdml | Tfpi | |
| Genes downregulated in osteoarthritic cartilage (71 genes) | | | | | | |
| Agtr2 | Cmtm5 | Evx1 | Il17rb | Pde3b | Sgsm1 | Tmem176b |
| Alx4 | Cmya5 | Fam198a | Il18bp | Piezo2 | Slc14a1 | Tnfrsf4 |
| Apol9b | Col11a2 | Fbln7 | Kif1a | Ppp1r1b | Slc25a27 | Wnk2 |
| Atp1b2 | Col16a1 | Fgf14 | Lgi4 | Prx | Slitrk4 | Zcchc5 |
| C530008M17Rik | Crim1 | Frzb | Lrrtm2 | Ptger3 | Sncg | Zfp385c |
| Cacna1c | Cyp39a1 | Gpc5 | Mpped2 | Rarres2 | Srl | |
| Cacna2d2 | Dact1 | Gprc5b | Myh14 | Rcan2 | Steap4 | |
| Capn6 | Dcc | Grin2c | Myoz3 | Rflna | Stk32b | |
| Cdhr1 | Ddit4 | Gucy1a3 | Nfam1 | Rspo3 | Tac1 | |
| Ces1a | Erich3 | Hmgcll1 | Nrxn2 | Sdc3 | Tceal5 | |
| Chrdl2 | Esr1 | Igf2 | Obscn | Sez6l | Tmem176a | |

Example 3. Modulation of Osteoarthritis Pathogenesis by RIP3

MMP3, MMP13, ADAMTS4 and ADAMTS5 are known to play an important role in osteoarthritis pathogenesis, and Cox2 is mainly involved in inflammation and eventually leads to cartilage matrix degradation by activation of collagenase and aggrecanase. In order to investigate the association between elevated RIP3 expression and osteoarthritis pathogenesis, the present inventors identified the expression of upregulated catabolic factors (MMP3. MMP13. COX2 and ADAMTS4) and downregulated anabolic factors (Col2a1 and Aggrecan) in articular chondrocytes (FIGS. 4A to 4C; FIGS. 5A and 5B), and these genes are all known to disrupt cartilage in osteoarthritis. MMP3 and MMP13 have collagenase activity, and Adamts4 and Adamts5 mainly function as aggrecanase 1 and 2, respectively. The present inventors found that aggrecanase and collagenase activities were upregulated by Ad-Rip3 infection (FIG. 4D). Consistent with the findings for chondrocytes, Ad-Rip3 induced severe cartilage destruction and osteoarthritis symptoms in WT mice compared to Ad-C. and immunohistochemical staining showed that Ad-Rip3 triggered RIP3 overexpres- RIP3 deficiency was found to attenuate osteoarthritis in the DMM-induced mouse model, suggesting that RIP3 plays a key role in osteoarthritis pathogenesis.

Figure 5E:
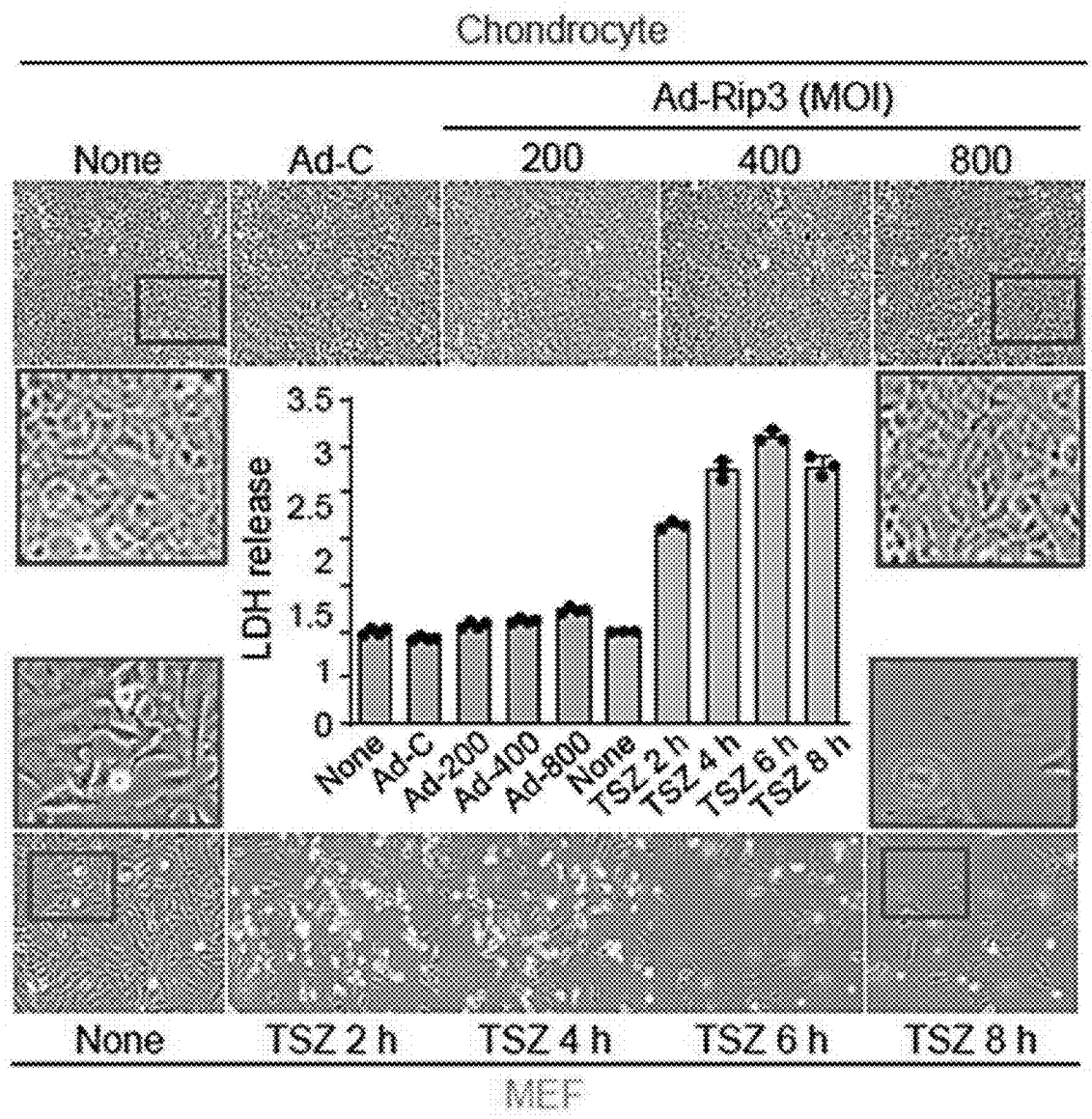
Figure 5F:
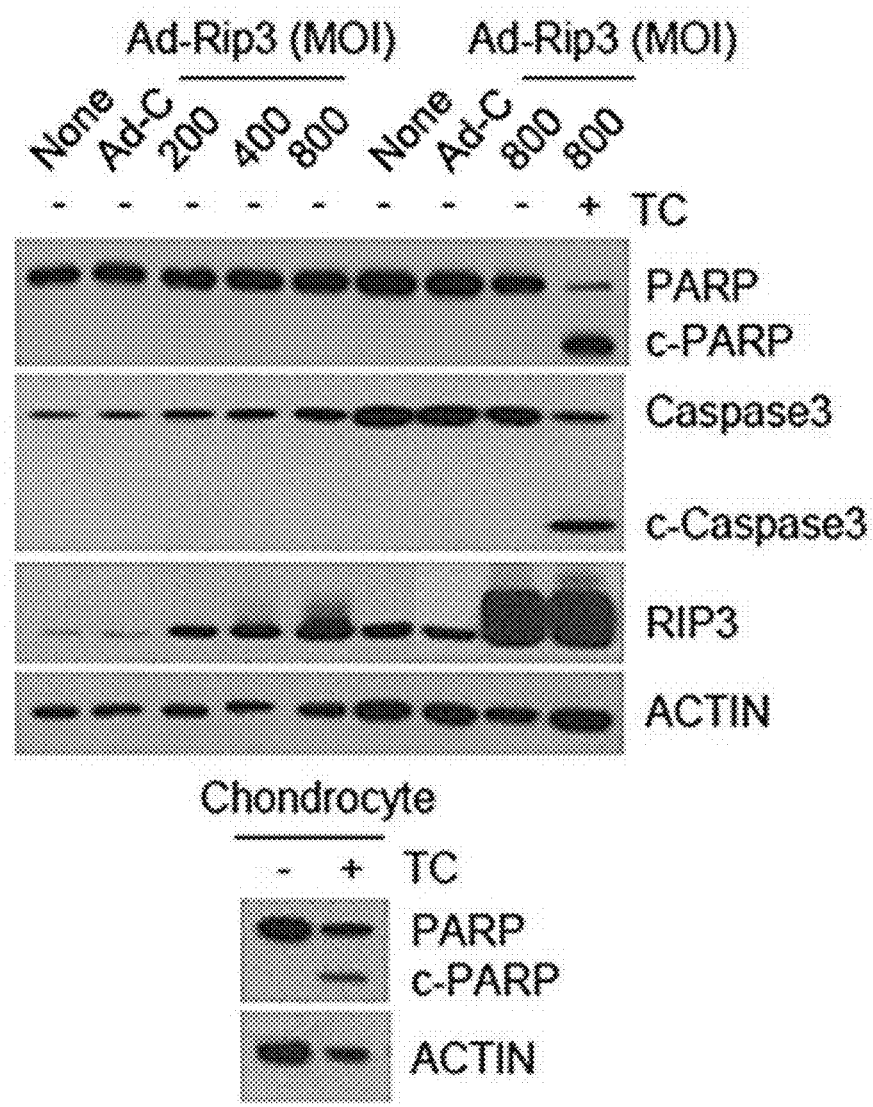
Figure 5G:
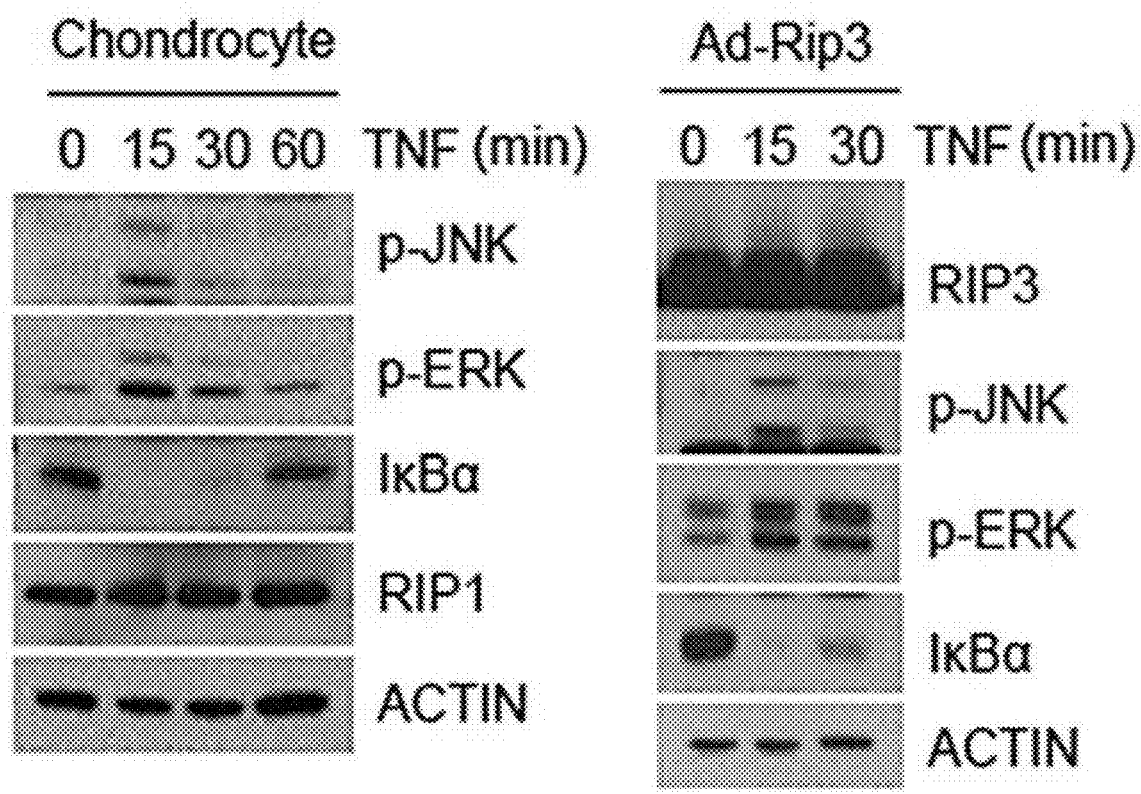

Since osteoarthritis and elevated RIP3 expression are both closely associated with cell death, the present inventors observed cytotoxicity in Ad-Rip3-infected chondrocytes to thereby determine whether RIP3 overexpression triggers the cell death pathway, which accelerates the development of osteoarthritis. Ad-Rip3-induced RIP3 overexpression did not alter chondrocyte morphology or LDH release (FIG. 5E) or did not induce PARP cleavage (FIG. 5F) despite TNF-mediated apoptosis-induced PARP and caspase 3 cleavage, suggesting that cell death is not implicated in RIP3-mediated osteoarthritis pathogenesis. However. RIP3 overexpression induced TNF-mediated signaling (FIG. 5G), indicating that RIP3 upregulation is capable of potentiating osteoarthritis pathogenesis through non-canonical MLKL-independent functions.

Example 4. TRIM24 as Negative Regulator of RIP3-Mediated Osteoarthritis Pathogenesis Signature In order to understand the basic mechanism of RIP3-mediated alterations in chondrocyte molecular patterns.

Figure 7A:
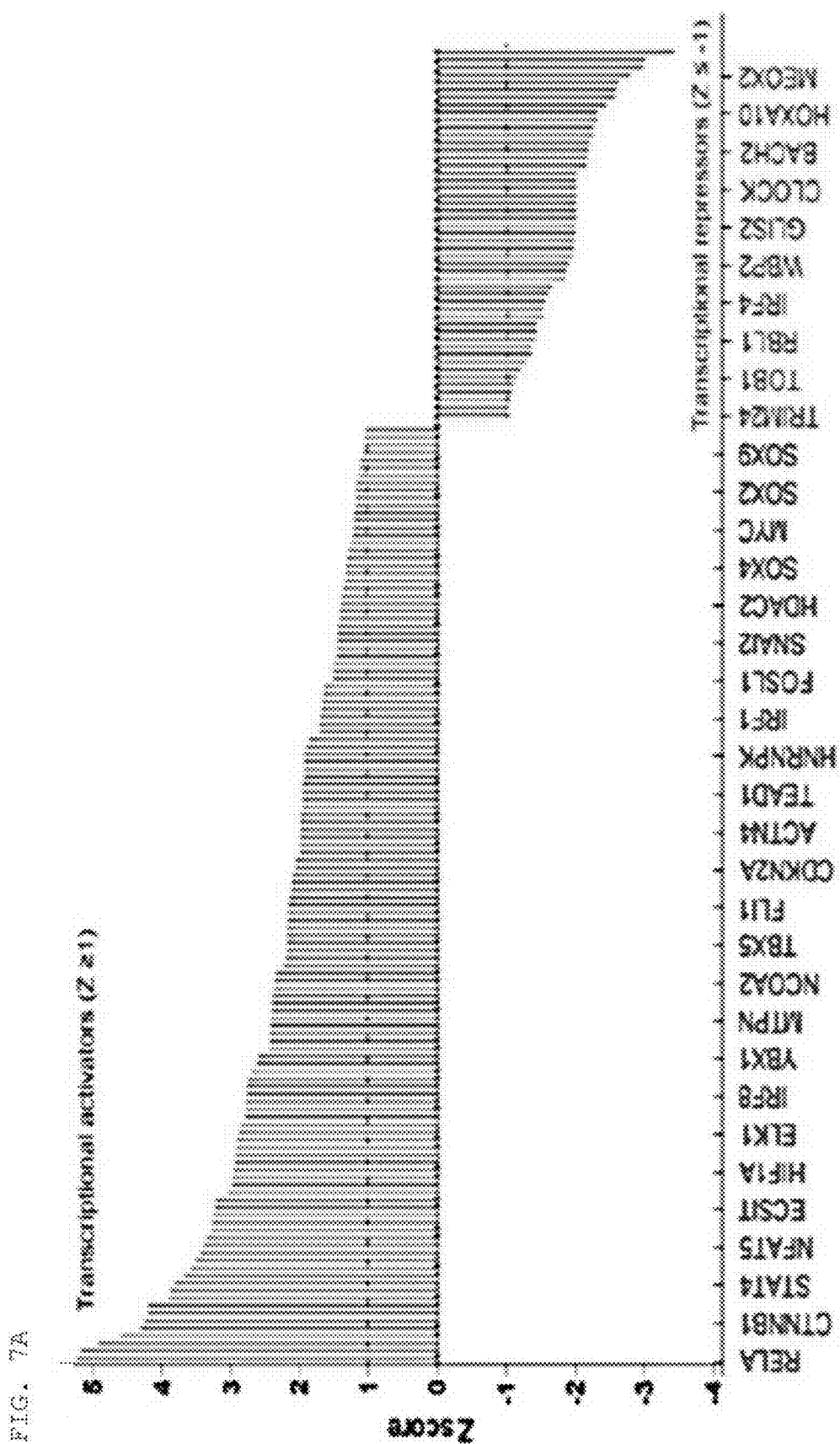
FIGS. 7A to 7D show that RIP3 overexpression alters gene expression patterns through the negative regulator TRIM24.
Figure 7B:
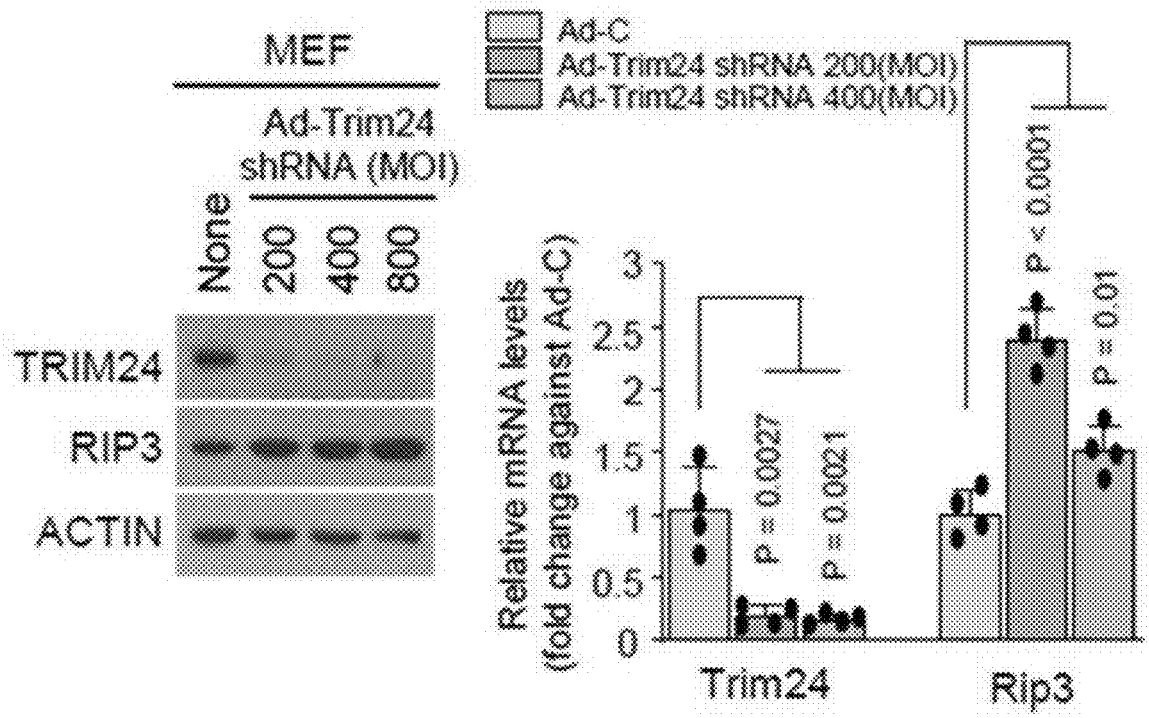
Figure 7C:
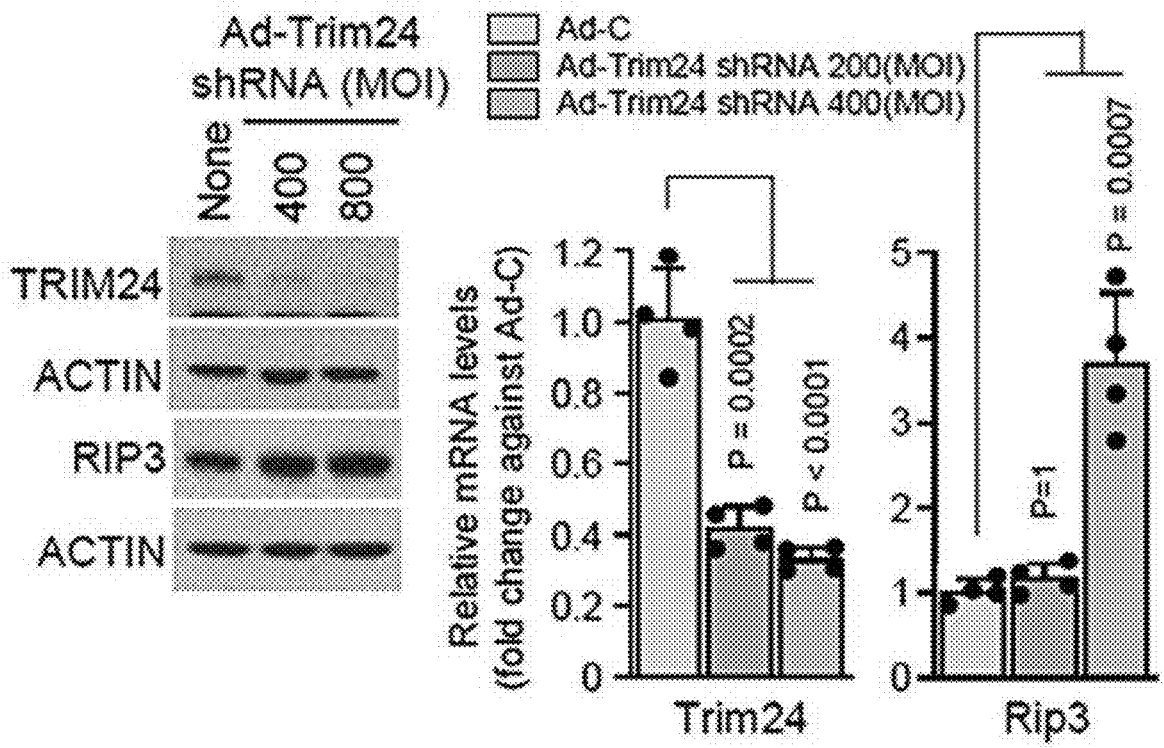
Figure 7D:
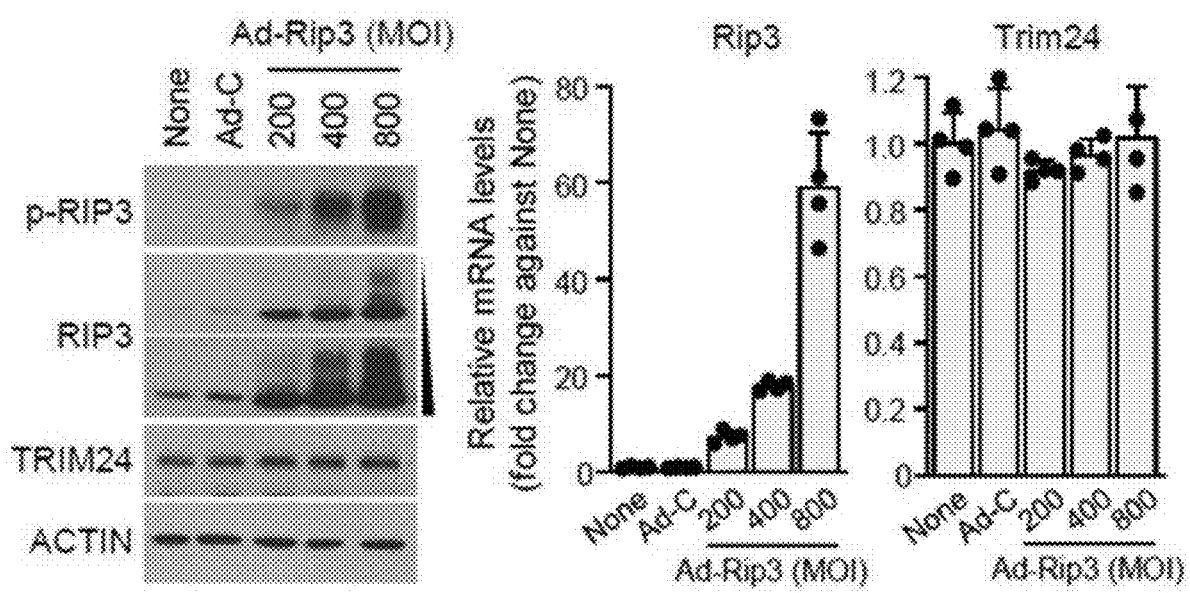
Figure 8A:
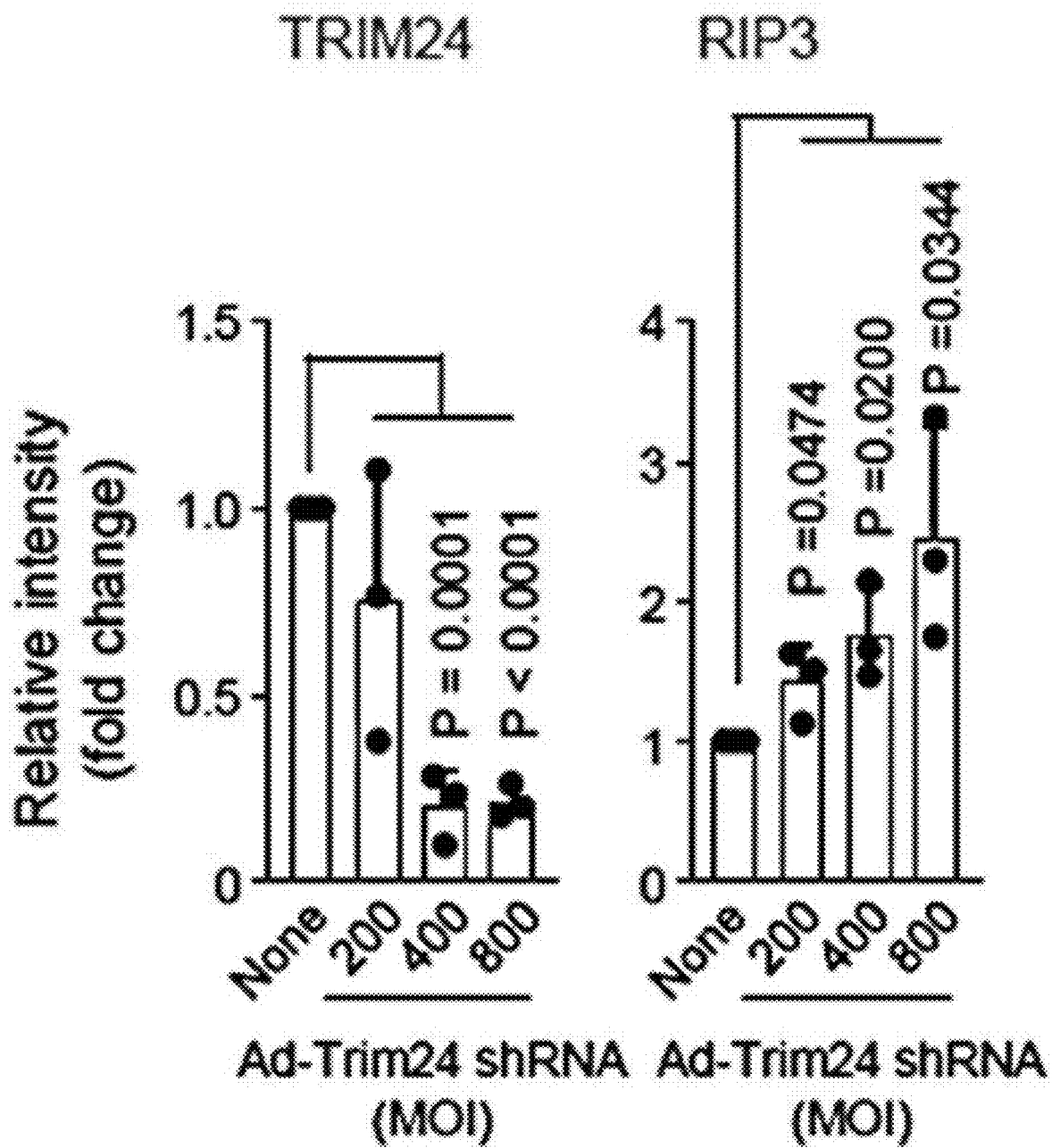
FIGS. 8A to 8F show that TRIM24 downregulation induces osteoarthritis-related gene expression.
Figure 8B:
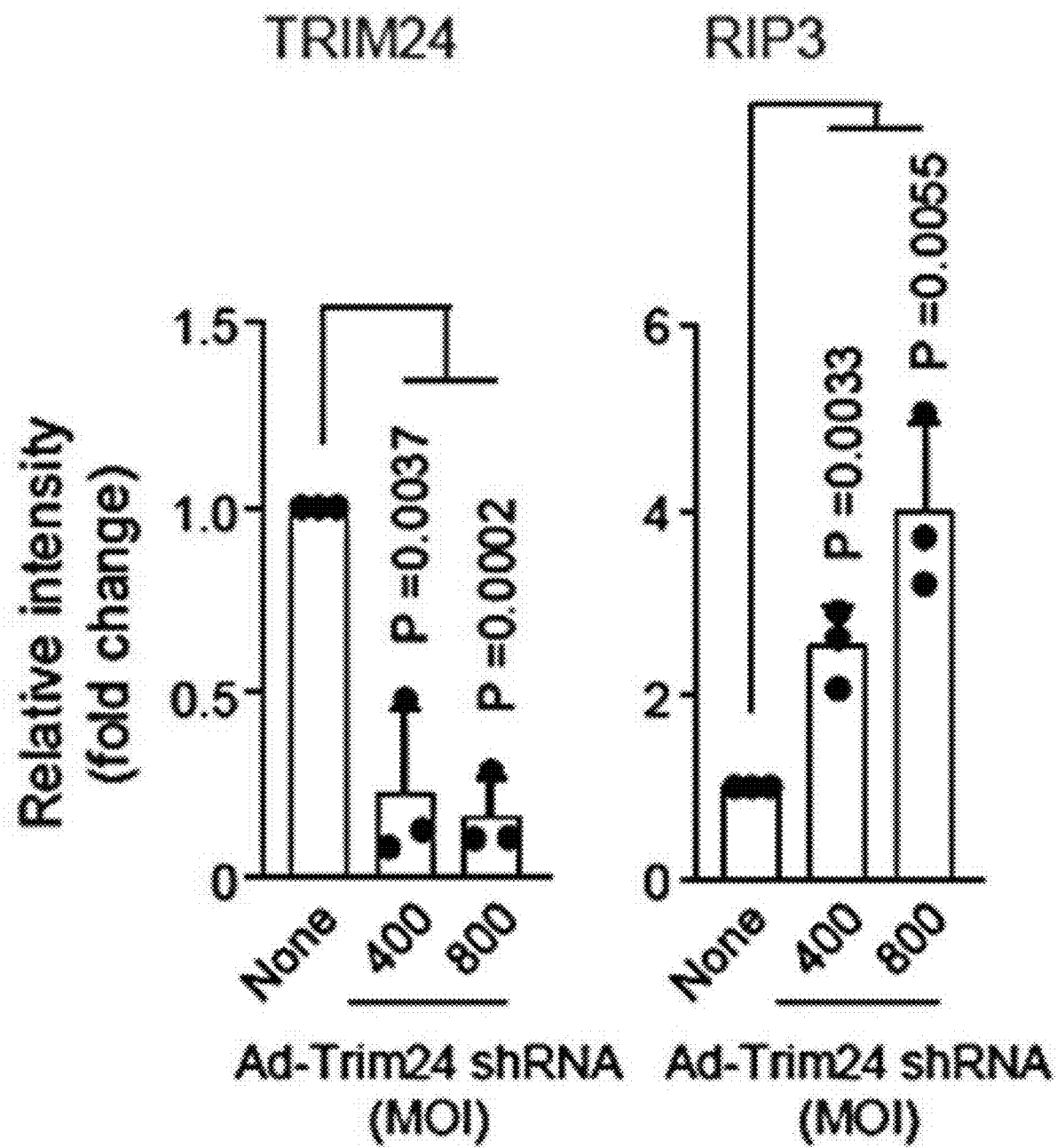
Figure 8C:
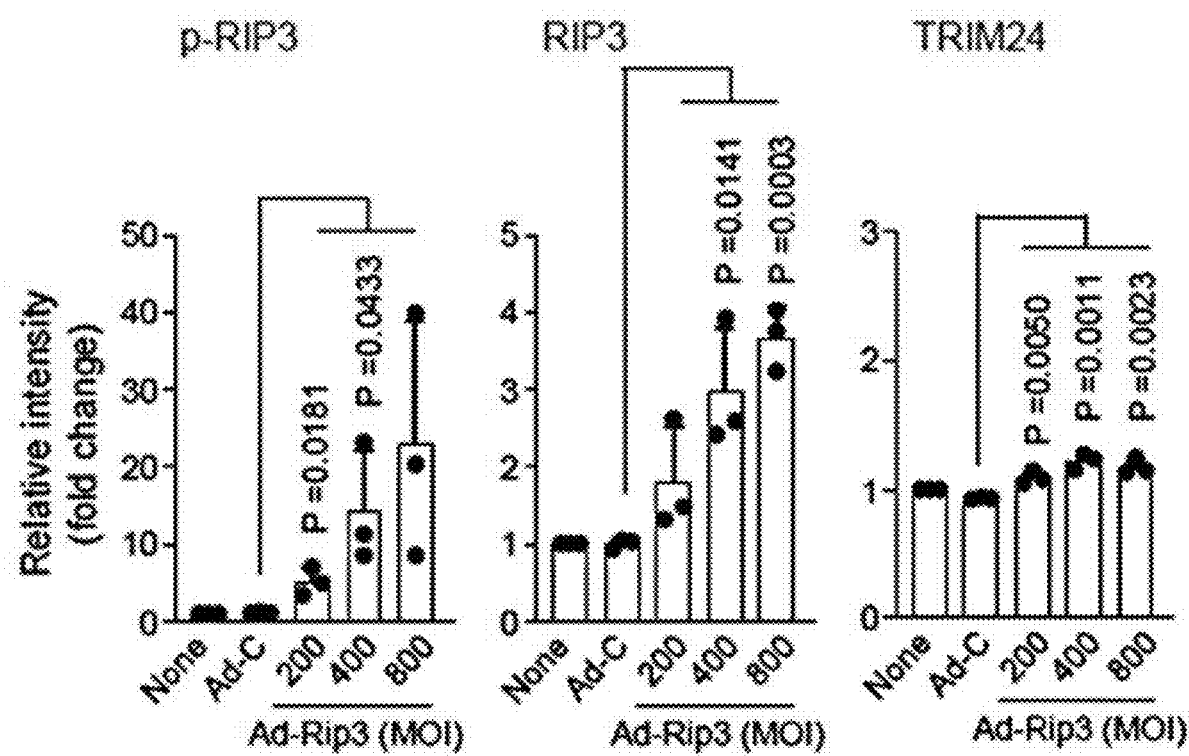

Ingenuity Pathway Analysis was performed to predict the upstream regulators responsible for these alterations. Consequently; the present inventors found 367 differentially expressed gene transcripts (FIG. 7A). Of the 69 negative upstream regulators, TRIM24, which is an important transcriptional coregulator that modulates TNFα signaling through NF-κ and interacts with retinoic acid receptor alpha (RARα) in a ligand-dependent manner to attenuate RARα-mediated transcription in mice, was selected. Although there have been reports on the function of TRIM24 in other tissues and diseases, whether TRIM24 modulation occurs in cartilage and other joint tissues is still unknown. In order to determine whether TRIM24 is a negative upstream regulator of RIP3 transcription, expression thereof in primary mouse articular chondrocytes was knocked down using Ad-Trim24 shRNA. Although TRIM24 downregulation enhanced Rip3 mRNA expression (FIGS. 7B and 7C; FIGS. 8A and 8B), RIP3 overexpression did not affect TRIM24 mRNA or protein expression (FIG. 7D; FIG. 8C), indicating that TRIM24 is a negative upstream regulator of RIP3 transcription.

Figure 8D:
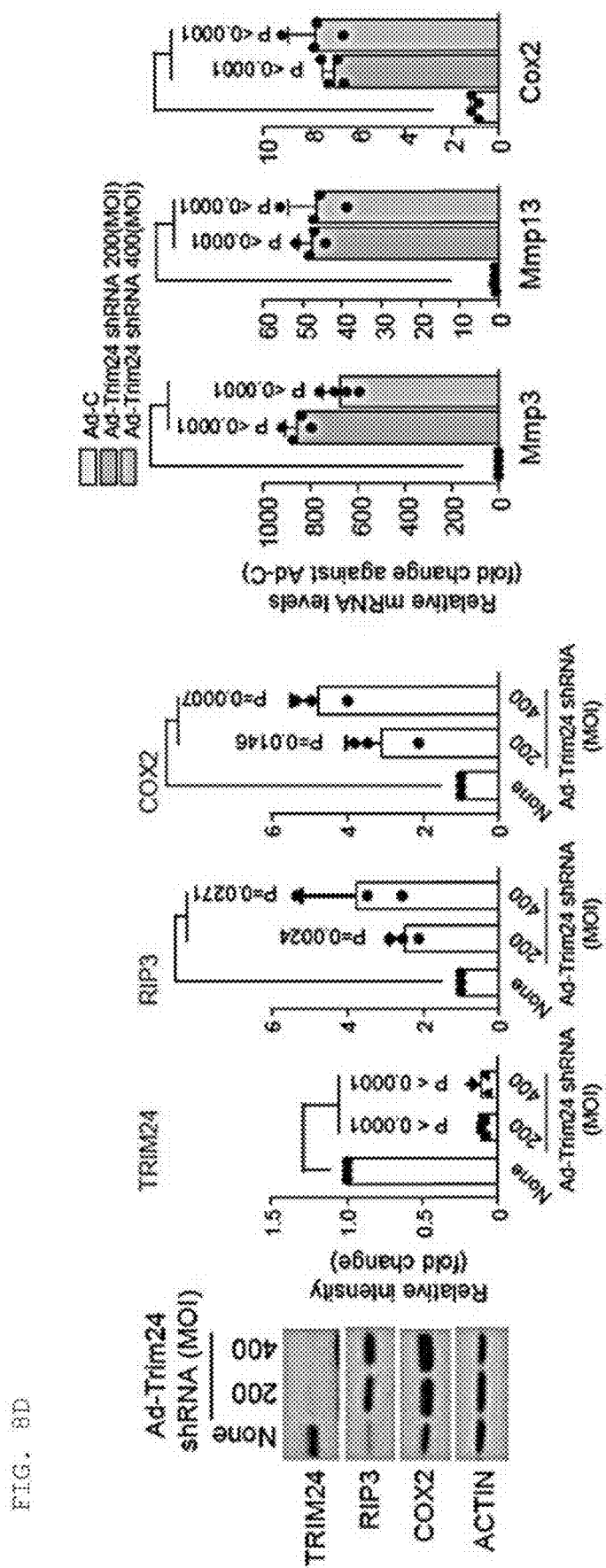
Figure 8E:
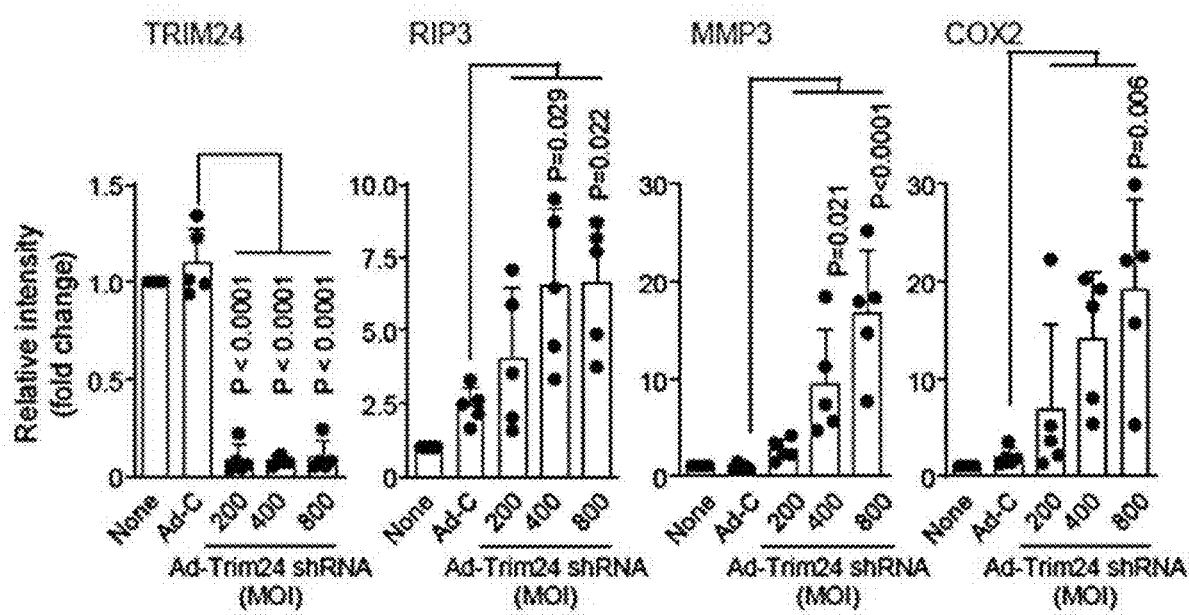
Figure 8F:
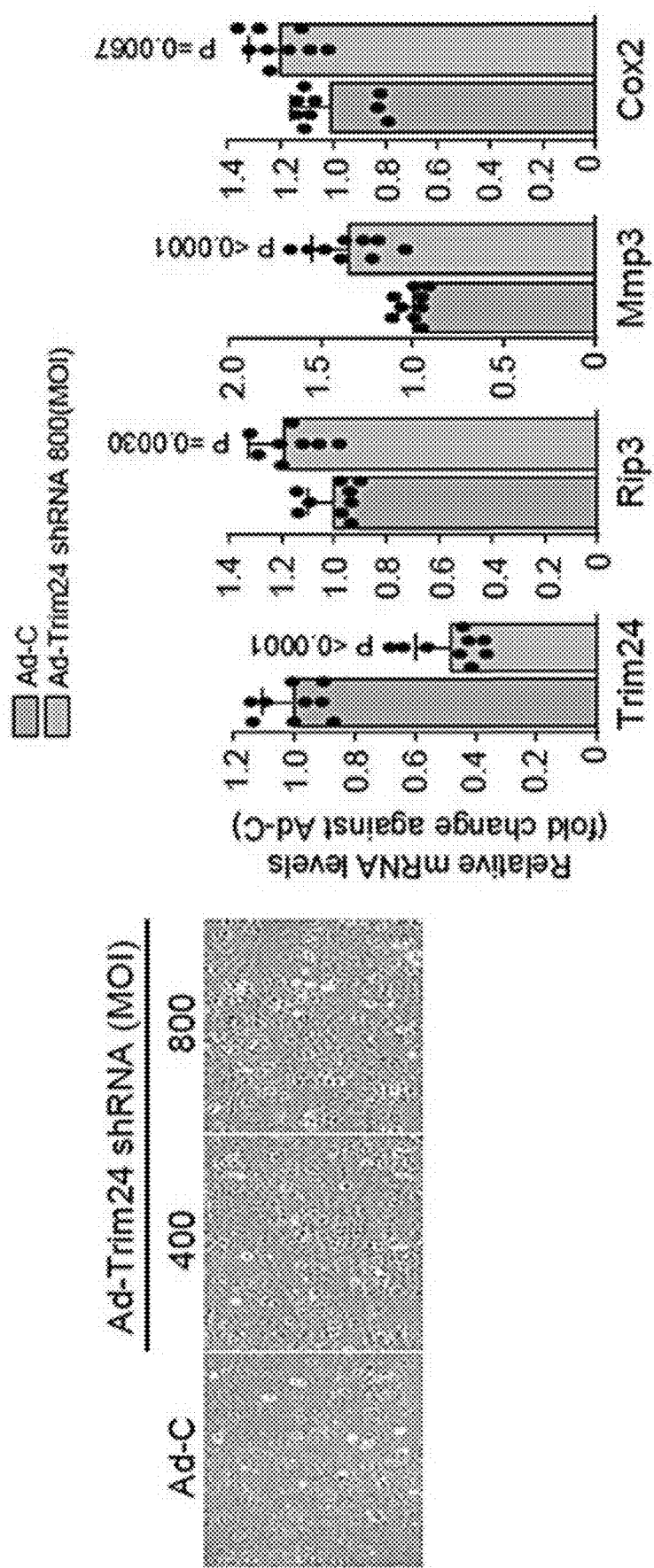
Figure 9A:
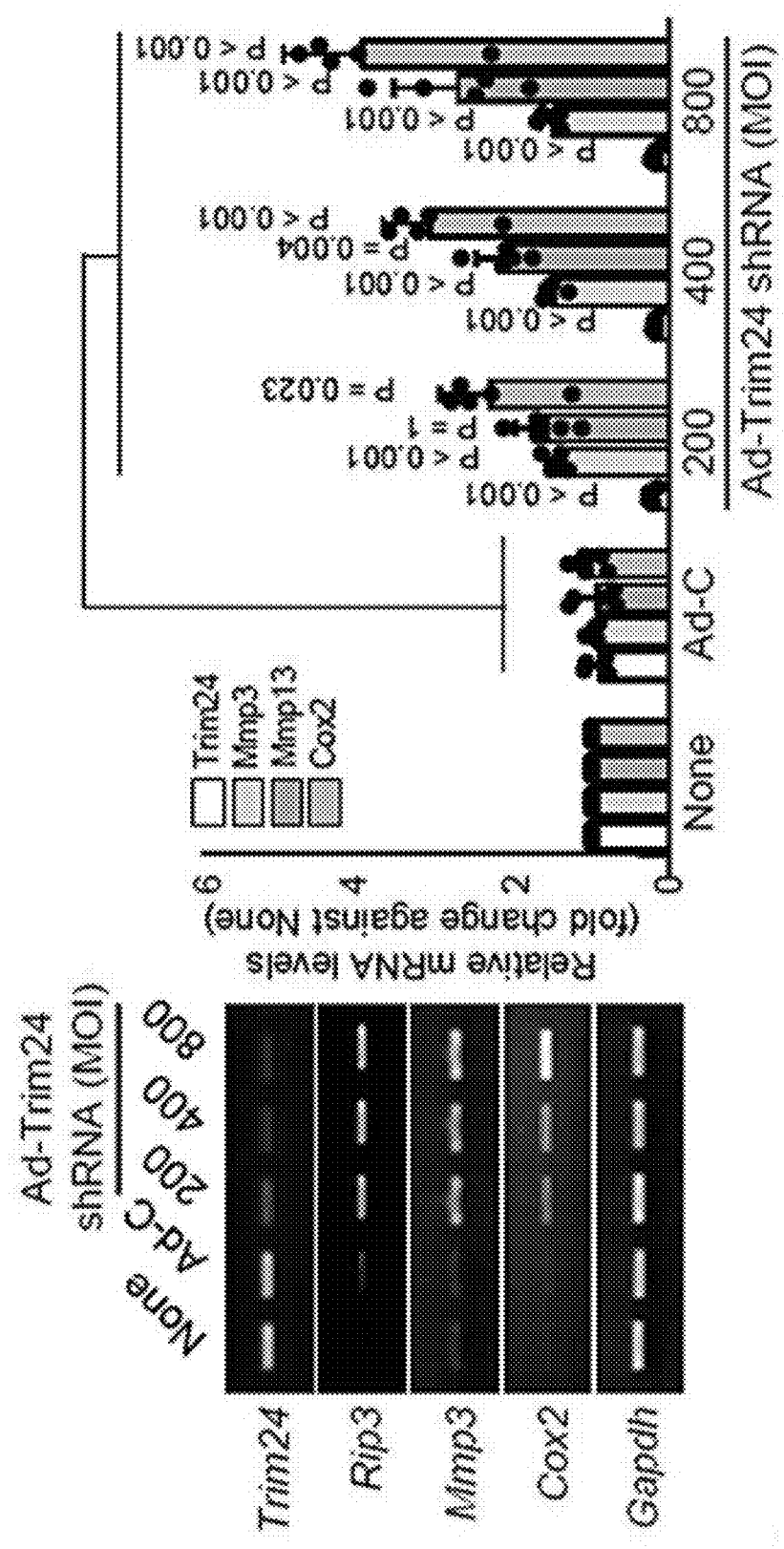
FIGS. 9A to 9E show that TRIM24 is the upstream regulator of RIP3 expression.
Figure 9B:
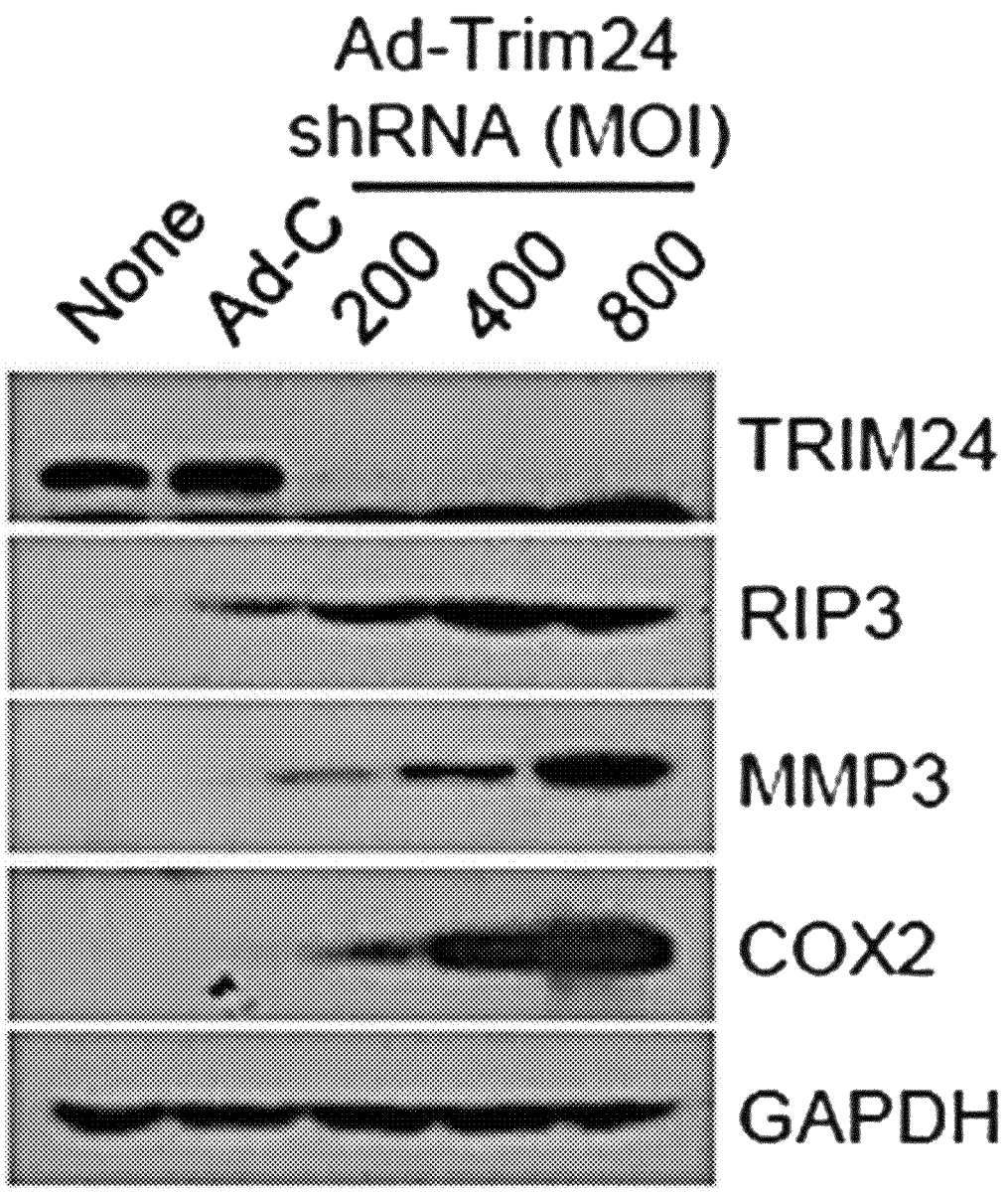
Figure 9C:
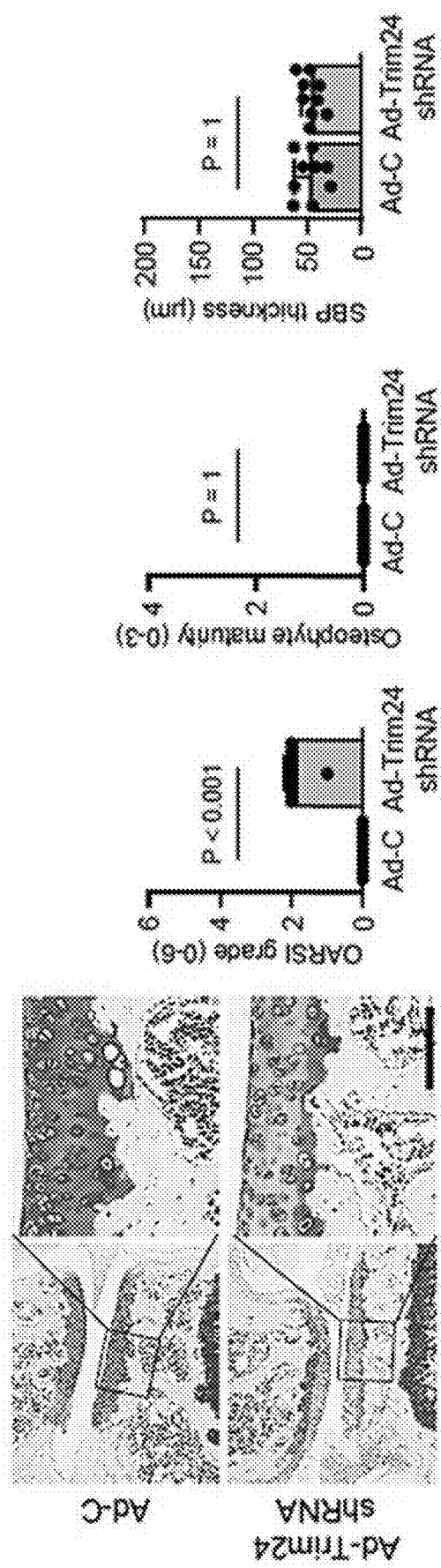
Figure 9D:
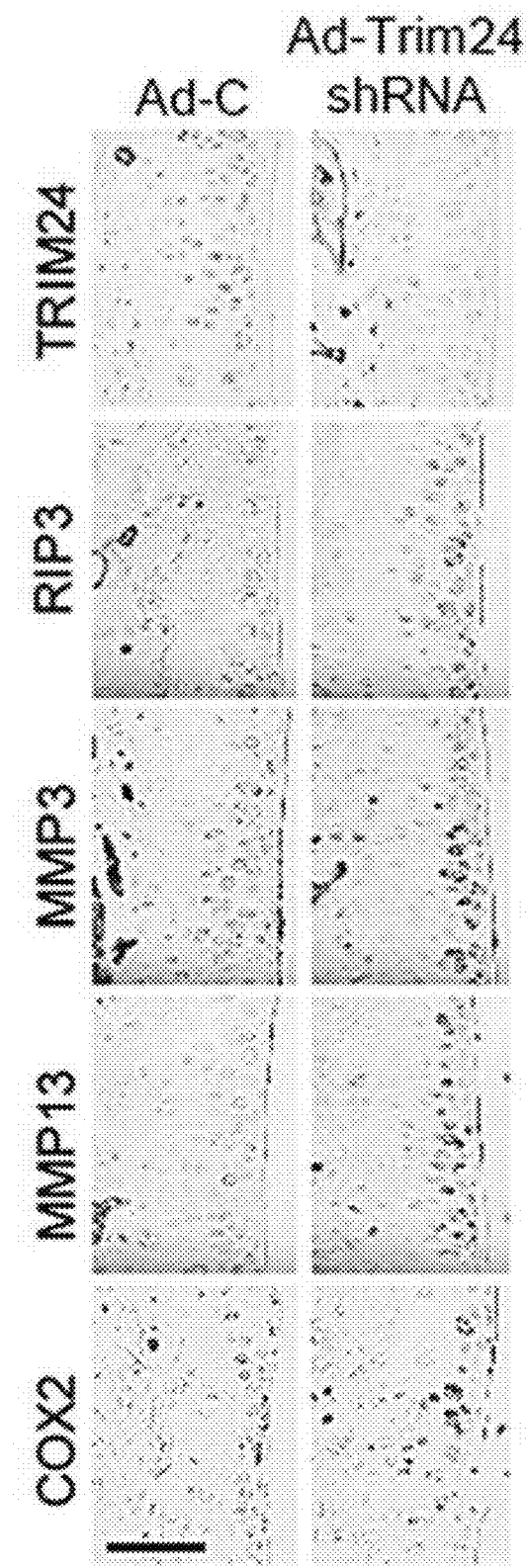
Figure 9E:
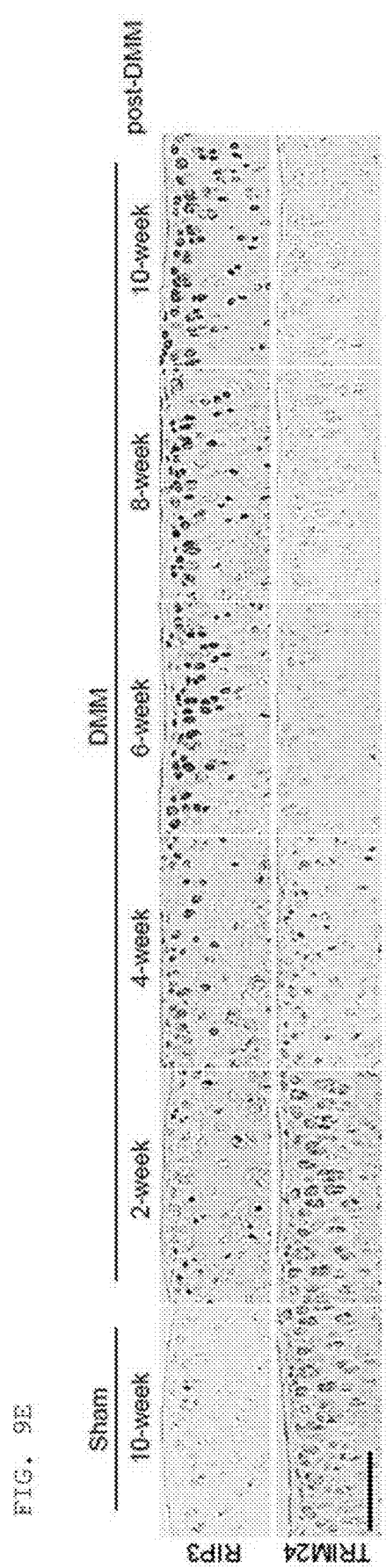
Figure 10A:
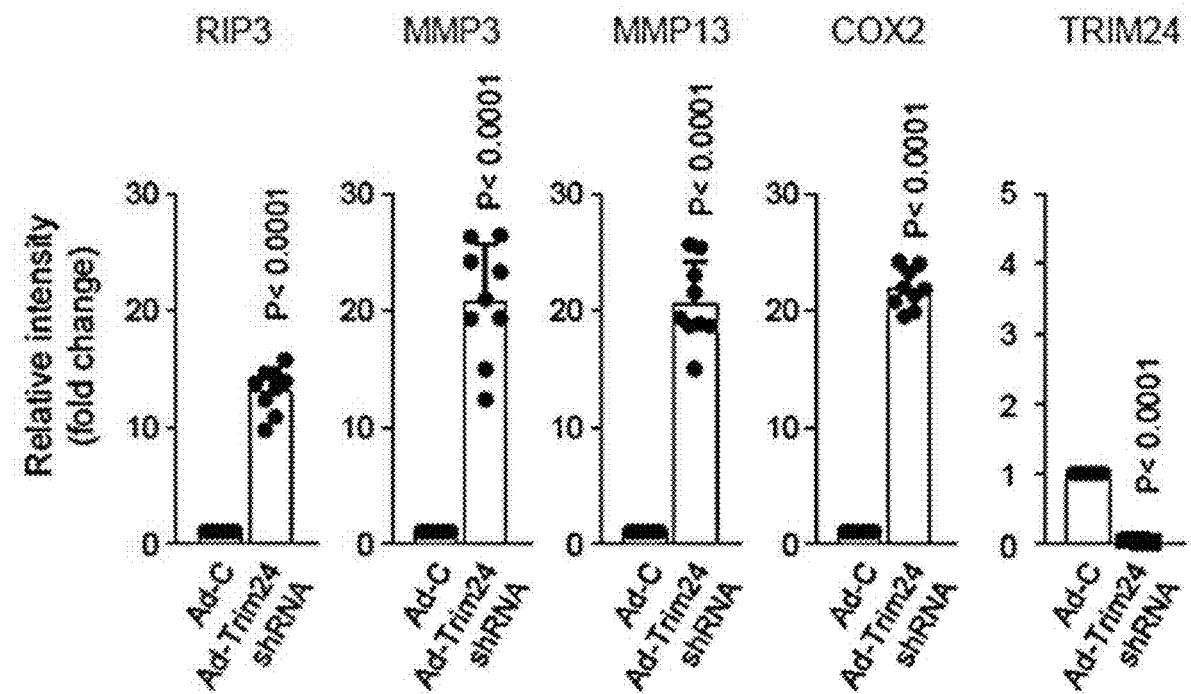
FIGS. 10A to 10C show that TRIM24 expression and RIP3 expression are inversely correlated in DMM-induced osteoarthritis models.
Figure 10B:
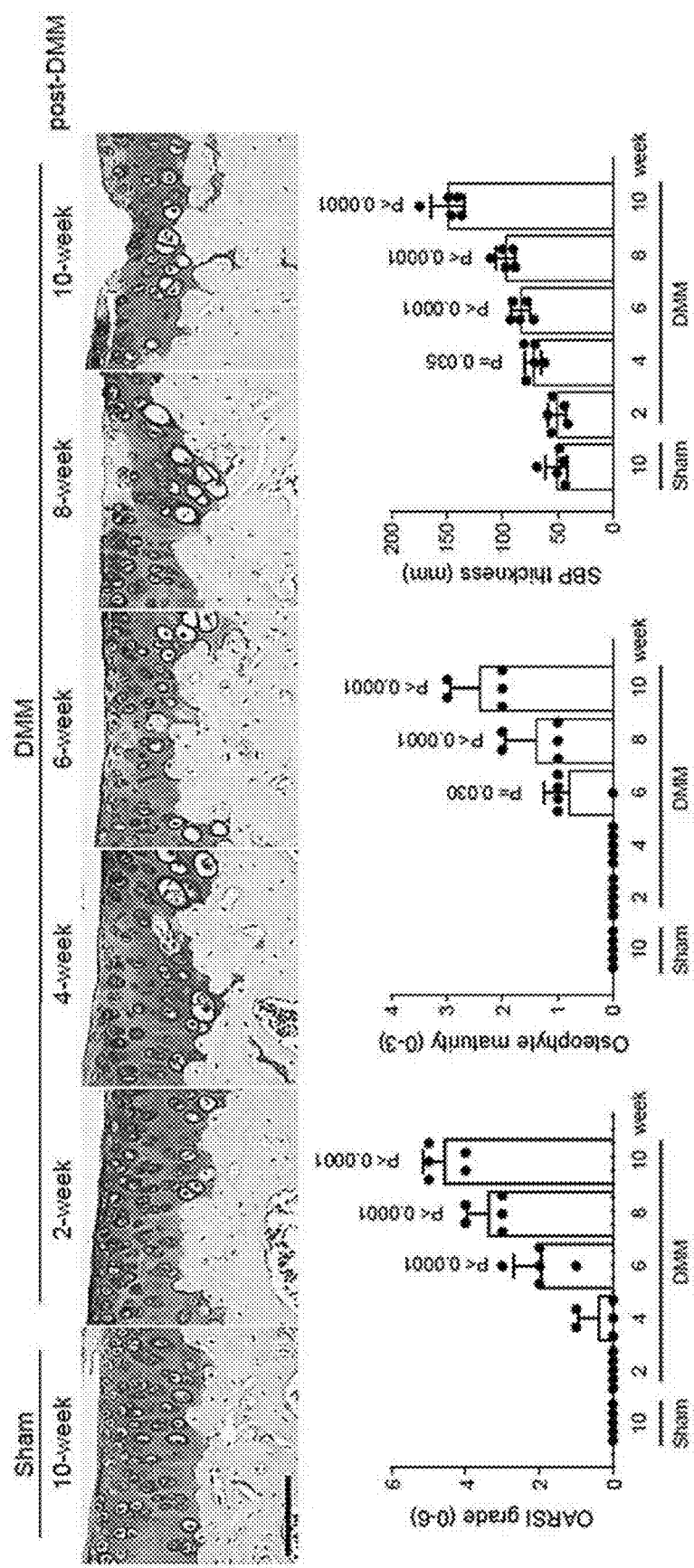
Figure 10C:
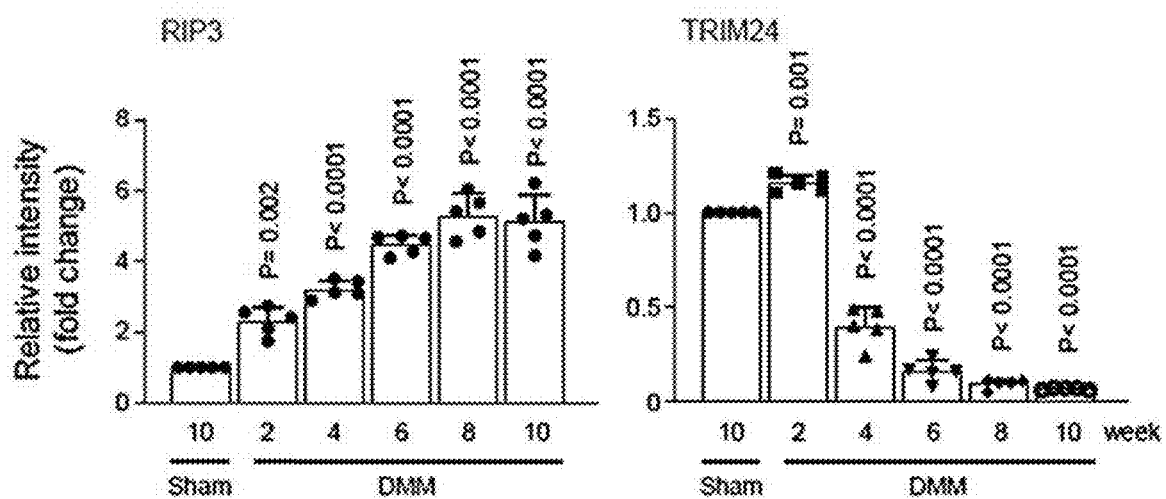

Next, the present inventors investigated whether regulating RIP3 transcription through TRIM24 knockdown in MEFs elicits changes in osteoarthritis-related gene expression patterns. MEFs infected with Trim24 shRNA increased RIP3 and COX2 protein expression, as well as Mmp3, Mmp13, and Cox2 mRNA expression (FIG. 8D). Similarly, chondrocytes infected with Ad-Trim24 shRNA also increased RIP3, MMP3. MMP13, and COX2 expression (FIGS. 9A, 9B, 8E, and 8F), indicating that RIP3 could be a molecular target of TRIM24-mediated negative regulation. Ad-Trim24 shRNA-mediated TRIM24 knockdown in mouse knee joint tissue significantly increased cartilage destruction, osteophyte formation, subchondral bone plate thickness (FIG. 9C), and catabolic factor expression (MMP3, MMP13 and COX2) (FIG. 9D and FIG. 10A). In order to clarify the contribution of the TRIM24-RIP3 axis to the development or progression of osteoarthritis disease, the present inventors examined the time-course expression profiles of Trim24 and RIP3 in mouse osteoarthritis cartilage samples after DMM surgery. Osteoarthritis manifestations, such as cartilage destruction, osteophyte formation, and subchondral bone sclerosis, were gradually increased at 4 to 6 weeks after DMM surgery (FIG. 10B), whereas Trim24 showed a 50% reduction at 4 weeks after induction of osteoarthritis, whereas in contrast, RIP3 expression was increased by 30% above normal at 4 weeks, by 80% at 6 weeks, and by 100% at 8 weeks and 10 weeks (FIG. 10E and FIG. 9C). Therefore, it was found that TRIM24 negatively regulates elevated RIP3 expression to thus accelerate osteoarthritis pathogenesis due to increased MMP3, MMP13, and COX2 from 6 weeks, and based on the inverse correlation between TRIM24 and RIP3, it is possible to predict the rates of development and progression of osteoarthritis.

Example 5. Identification of Drugs Associated with RIP3 Expression Using CMap

Figure 11A:
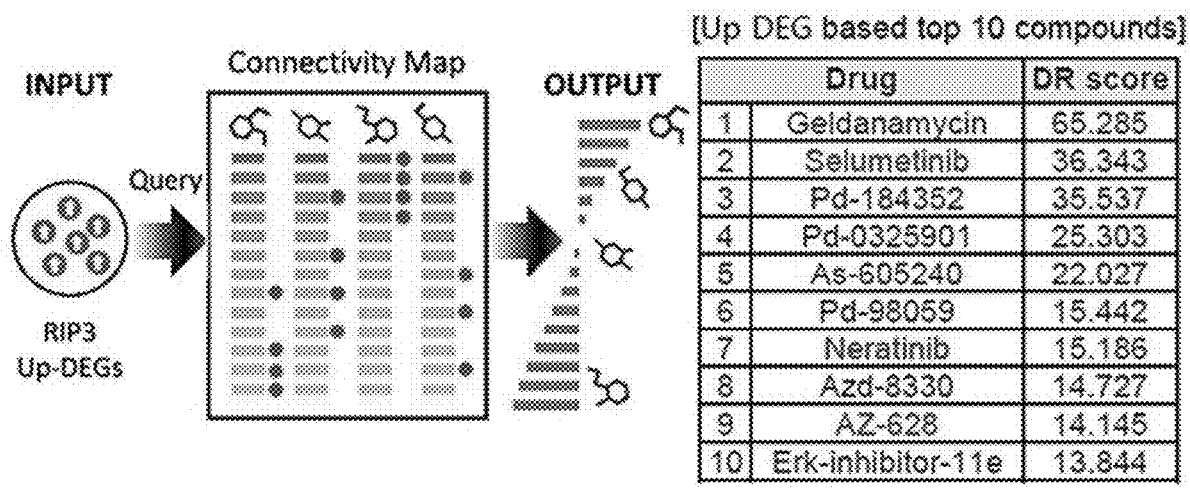
FIGS. 11A to 11G show that AZ-628 attenuates RIP3 kinase activity and reduces RIP3-mediated osteoarthritis pathogenesis.
Figure 11B:
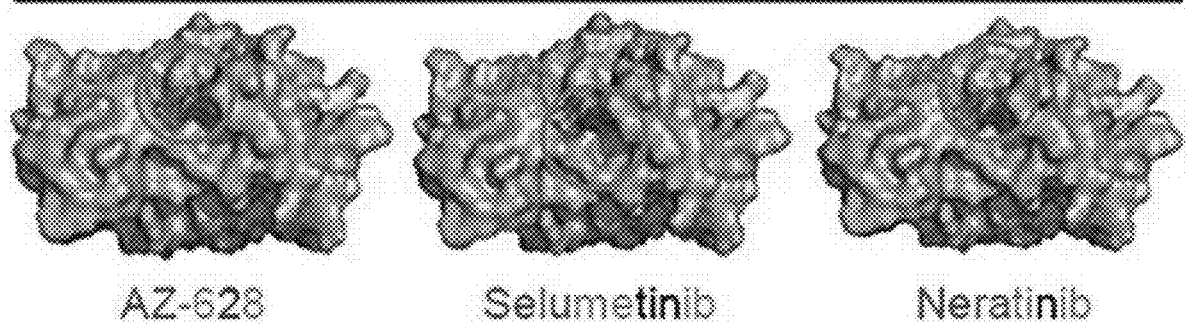
Figure 12A:
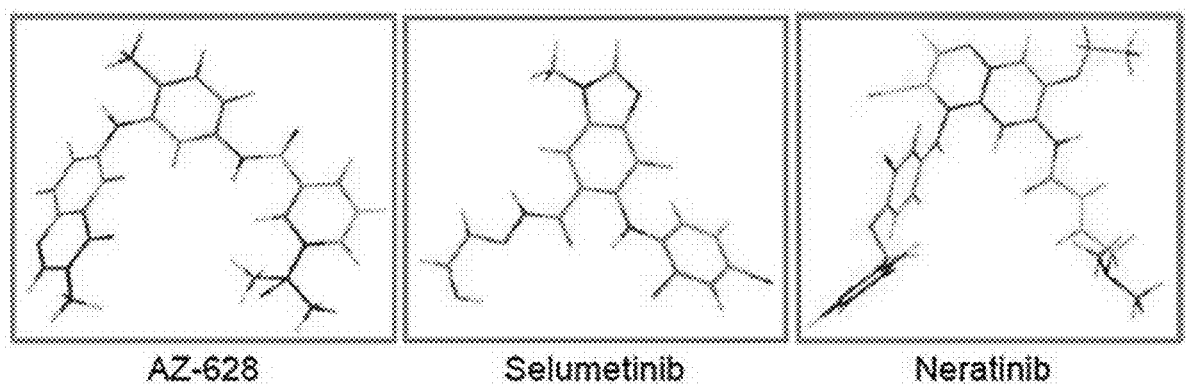

Limitations are imposed on directly targeting TRIM24 in drug development because of the diverse functions of TRIM24 as a transcriptional coregulator in the body. Therefore, the present inventors identified drugs capable of blocking osteoarthritis pathogenesis by inhibiting RIP3 through in silico compound screening using a CMap approach. Briefly, the present inventors searched for compounds with opposite expression signatures following RIP3 overexpression, prioritizing genes that were downregulated after upregulation by RIP3 overexpression in chondrocytes from the drug-induced transcriptome data of about 20,000 small molecules in the CMap database (FIG. 11A). The present inventors identified selumetinib, neratinib, and AZ-628, among candidate compounds that have not been previously associated with osteoarthritis (FIG. 11A and FIG. 12A). In molecular docking analysis, 9 compounds exhibited good RIP3 binding affinity (binding energy<−7.0 kcal/mol) and 5 compounds exhibited moderate RIP3 interaction (binding energy>−7.0 kcal/mol; FIG. 11B).

Figure 11C:
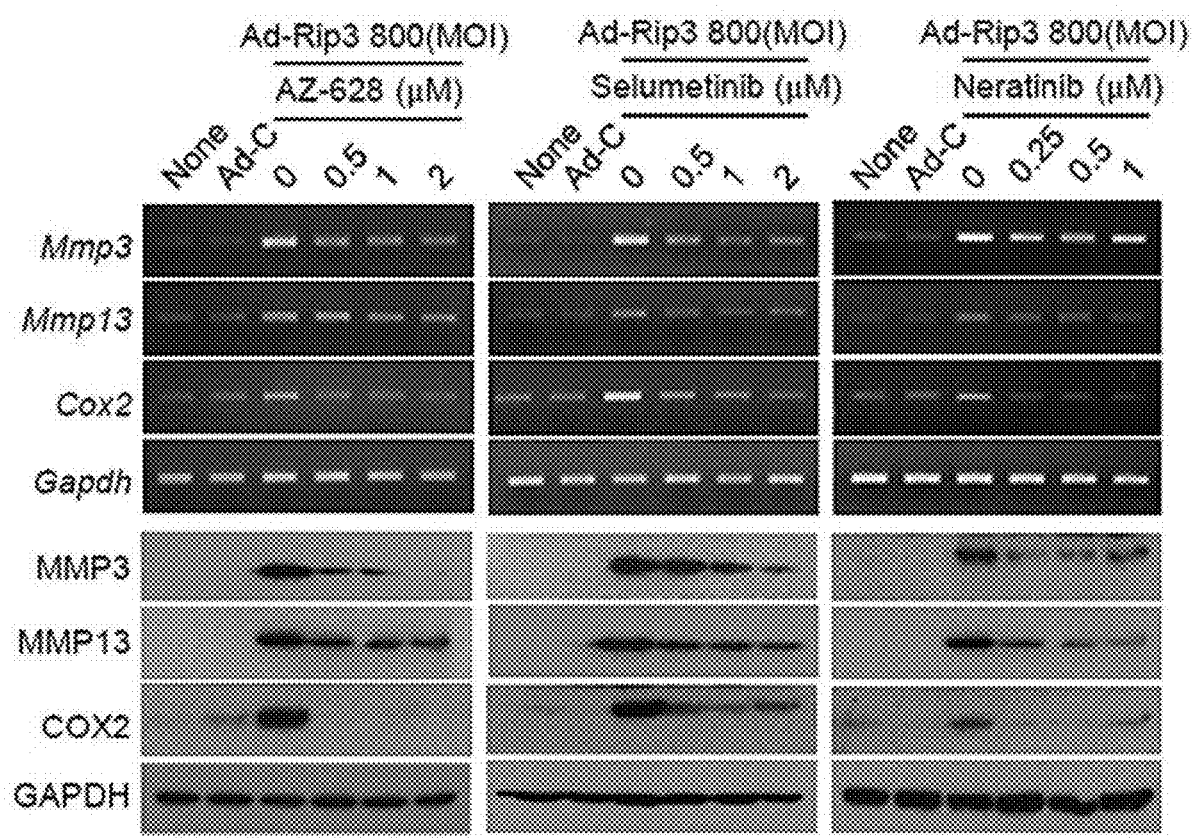
Figure 12B:
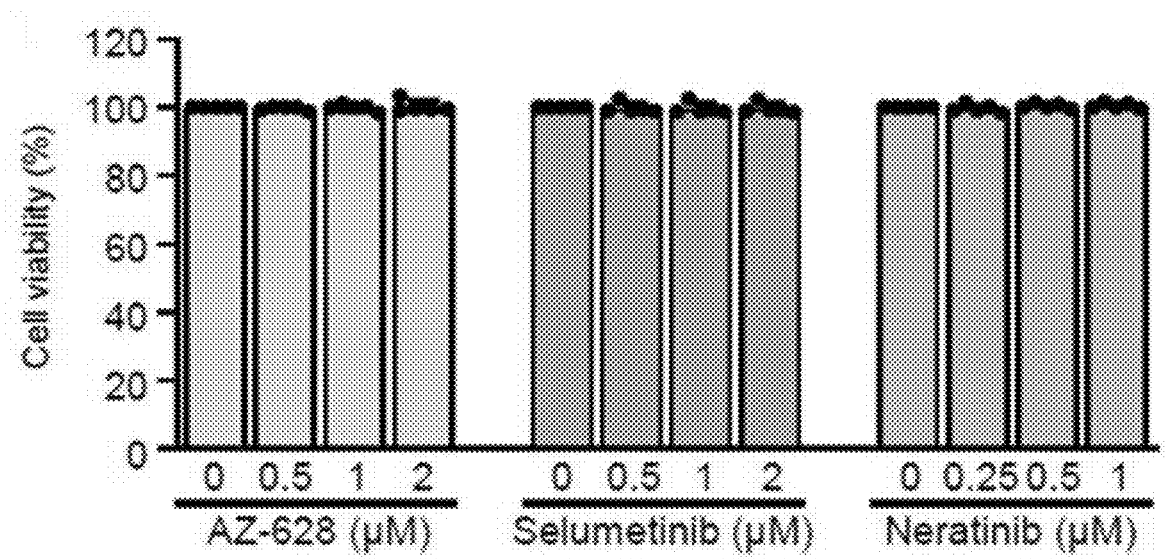
Figure 12D:
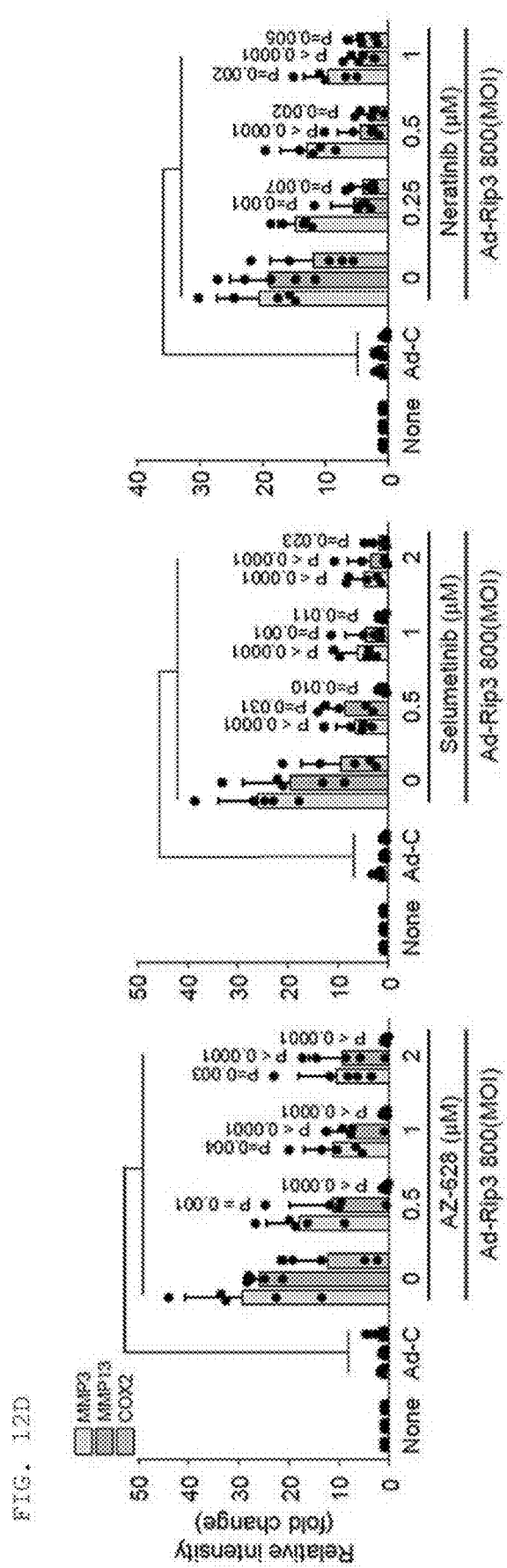

Based on the results of testing the cytotoxic effects of these compounds in chondrocytes, it was found that AZ-628 and selumetinib had no toxicity at 2 μM, whereas neratinib had no toxicity at 1 μM (FIG. 12B). Moreover, based on the results of investigating whether these compounds inhibit RIP3-mediated osteoarthritis pathogenesis, it was found that RIP3 overexpression-induced MMP3, MMP13, and COX2 expression was reduced in a dose-dependent manner (FIGS. 11C, 12C and 12D), and also that these compounds inhibited RIP3 activity. AZ-628 exhibited higher binding affinity than selumetinib or neratinib and more effectively inhibited the osteoarthritis manifestations in RIP3-overexpressing chondrocytes (FIG. 11C), which was further investigated. RIP3 overexpression leads to spontaneous autophosphorylation, and may potentiate osteoarthritis pathogenesis. Therefore, osteoarthritis could be attenuated by inhibiting RIP3 kinase activity using anticancer drugs that target RIP3 kinase, such as dabrafenib (DAB) and sorafenib.

Figure 11D:
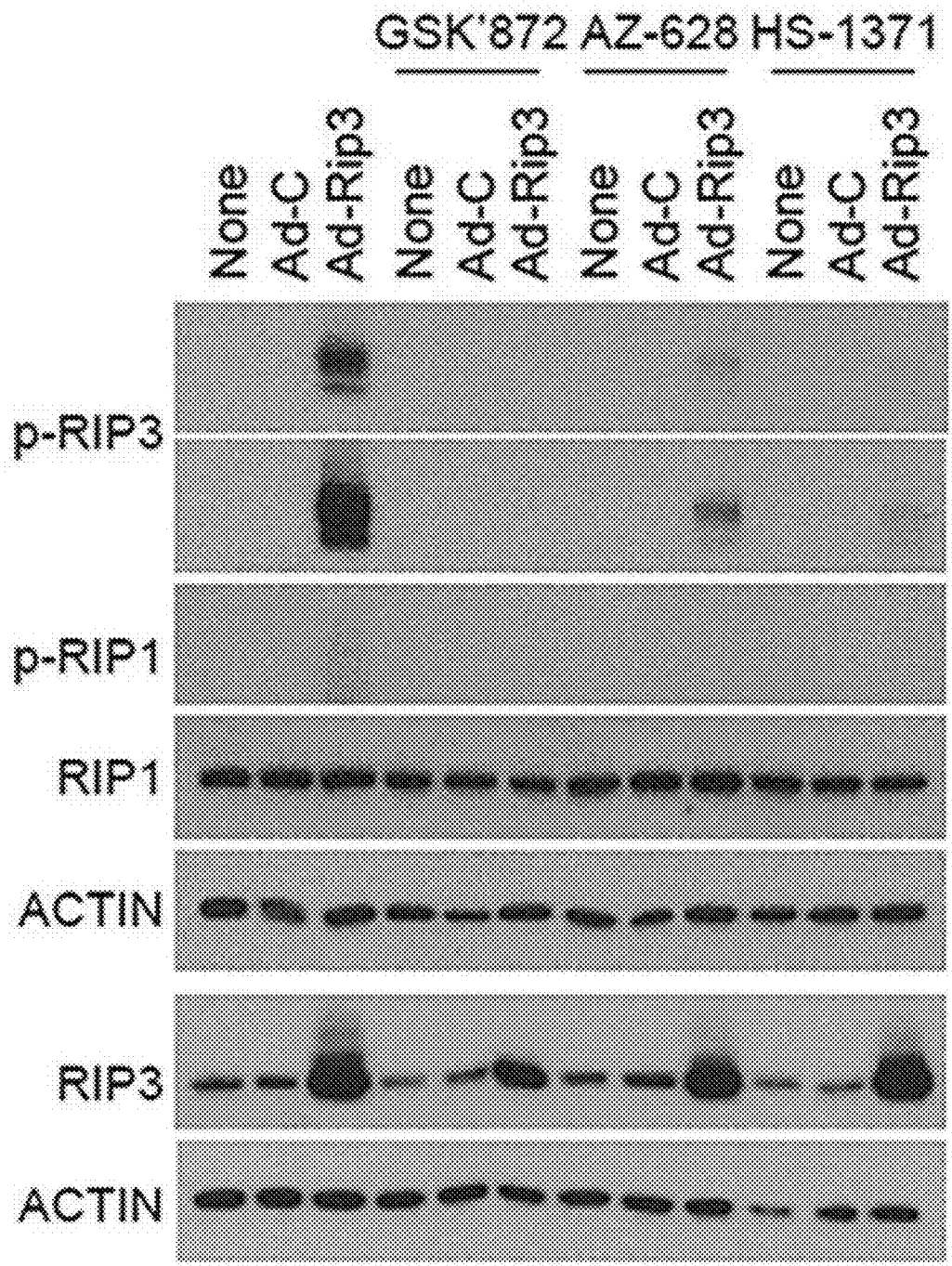
Figure 11E:
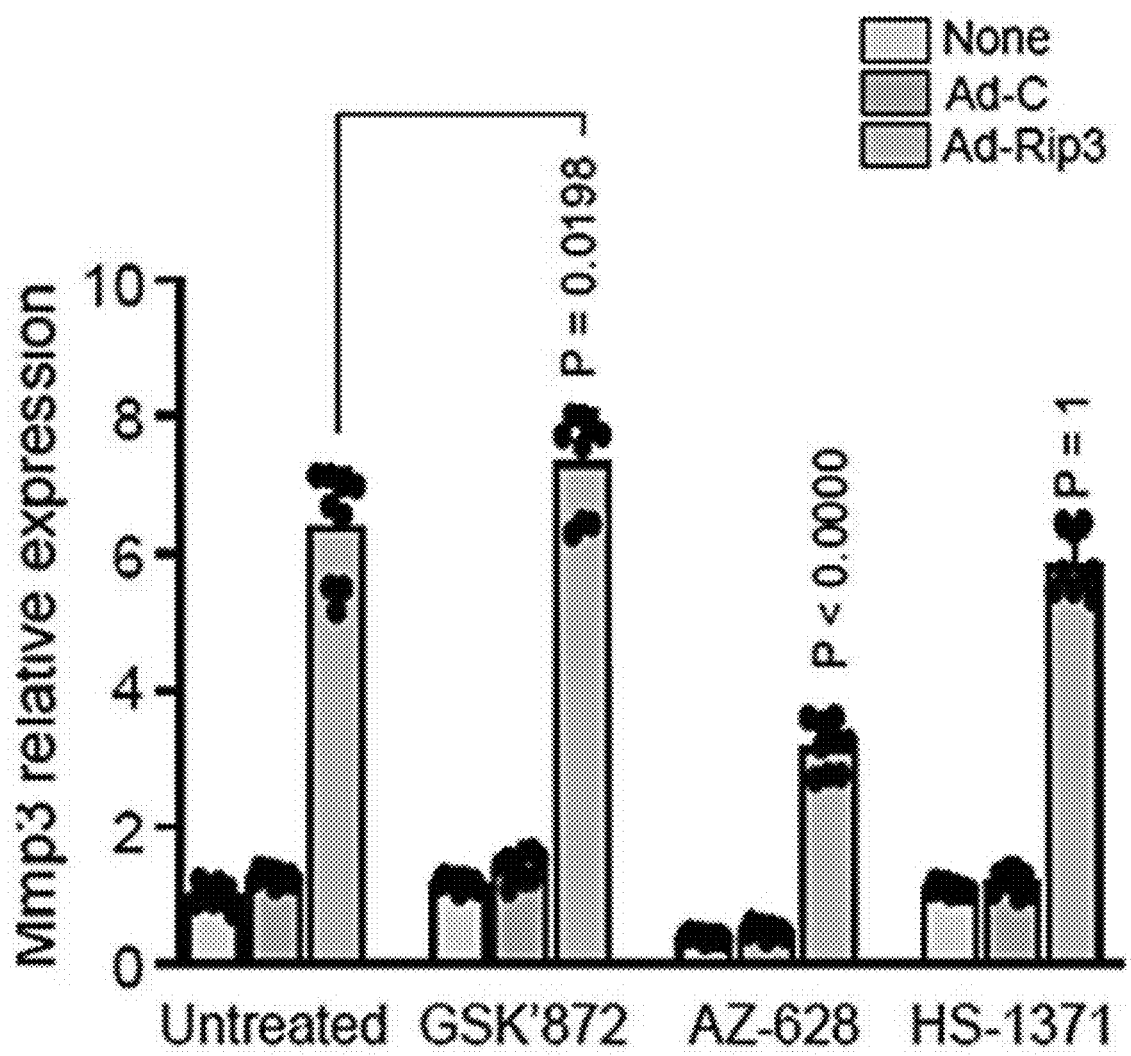
Figure 11F:
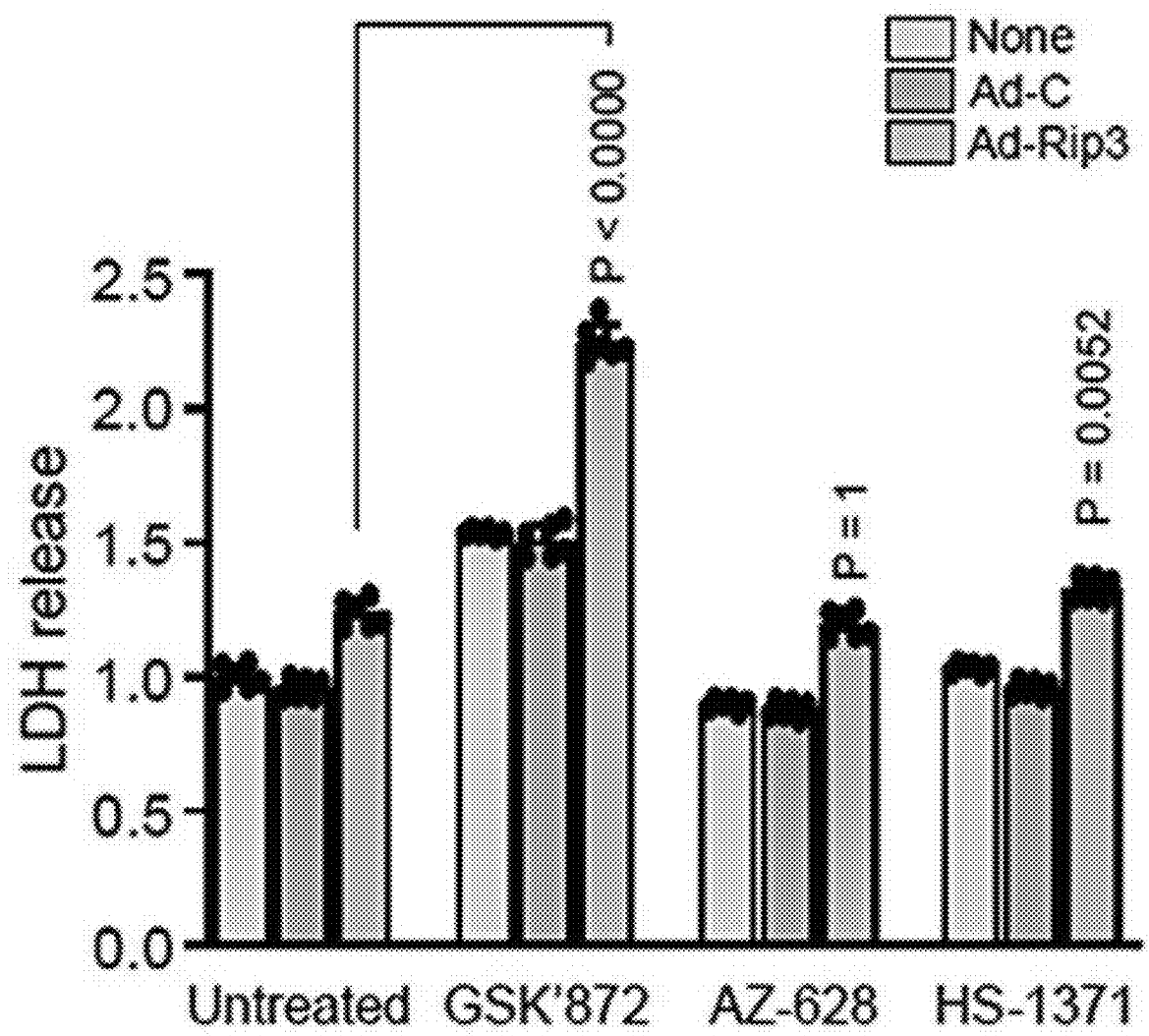
Figure 13B:
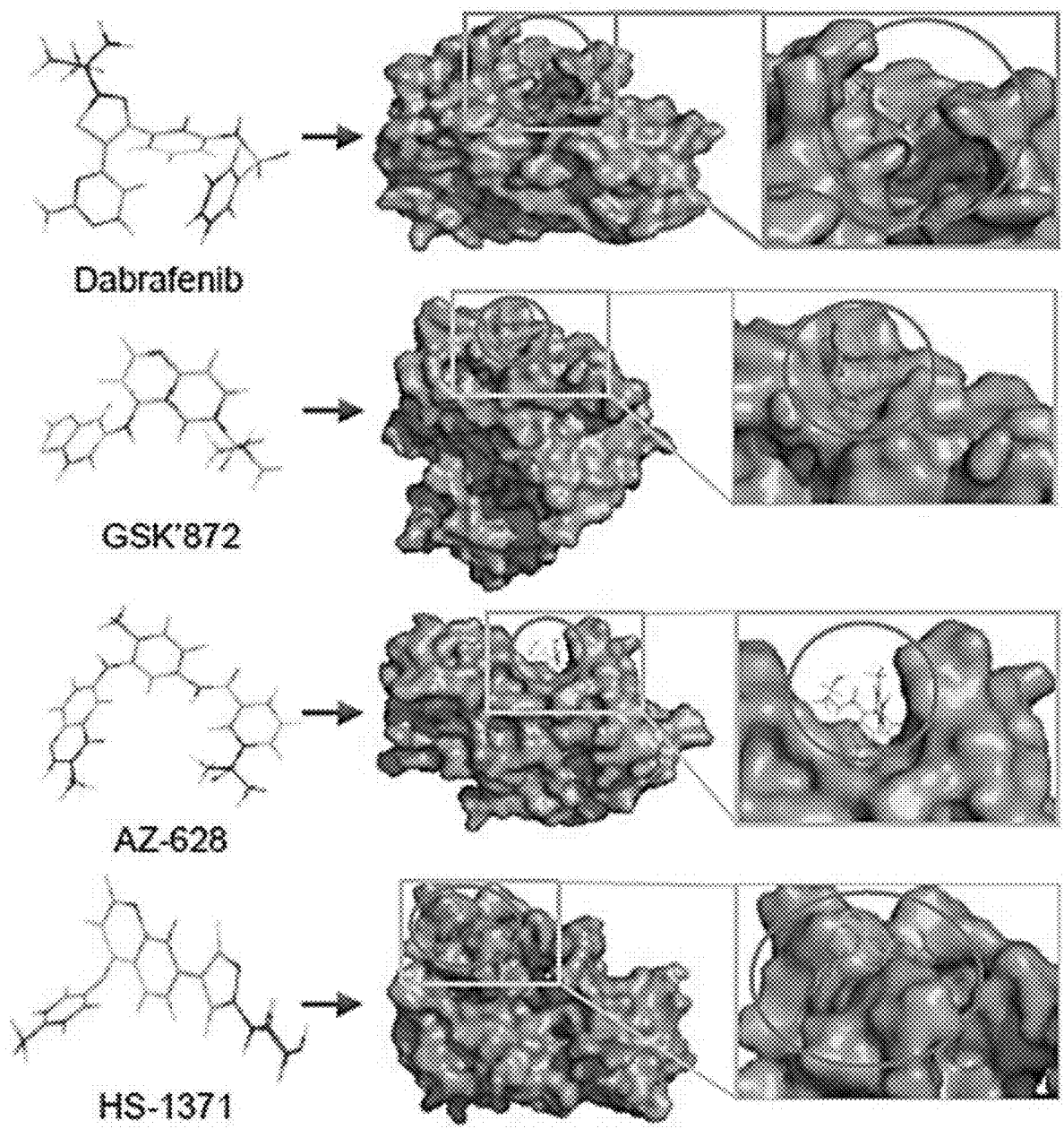
Figure 13C:
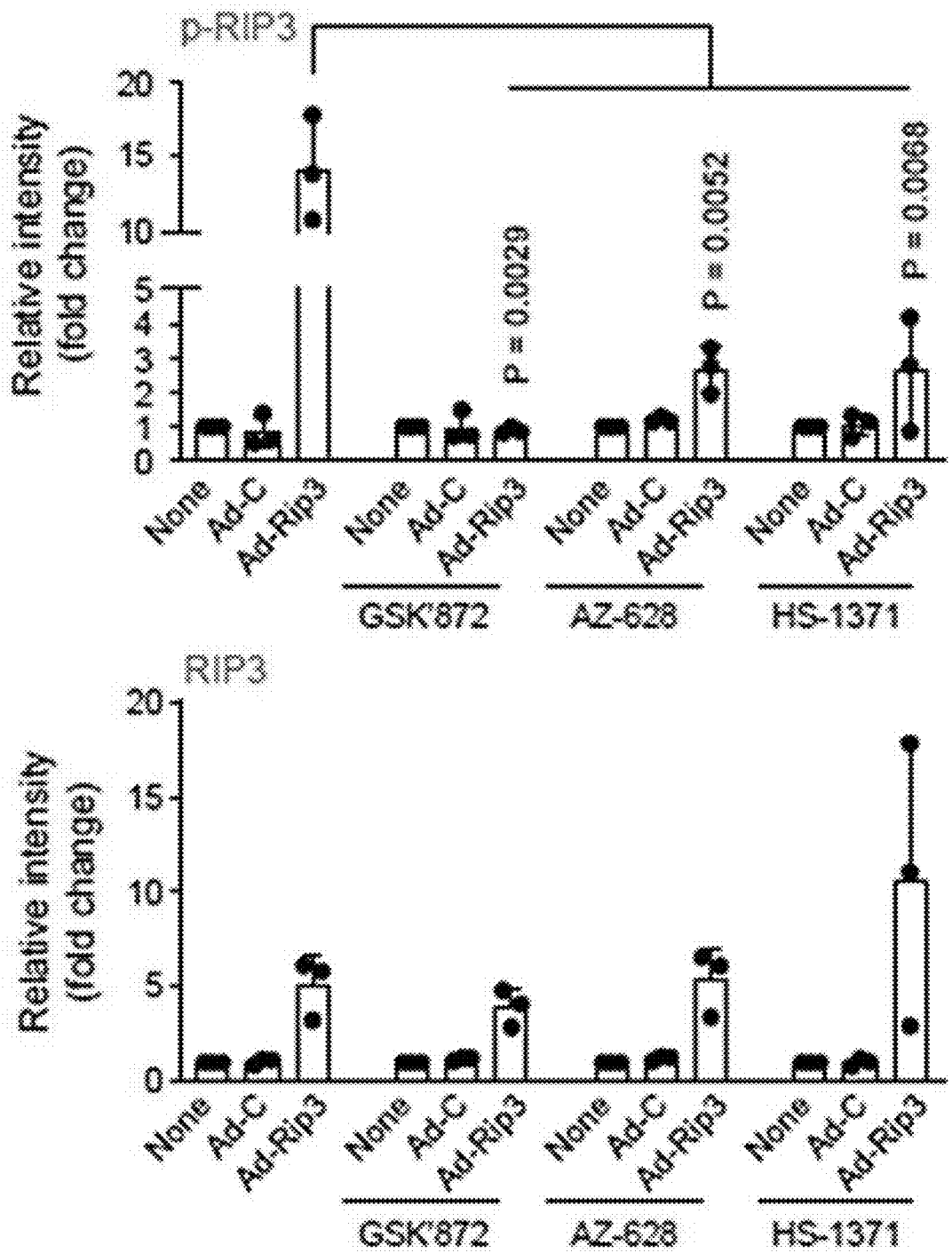
Figure 13D:
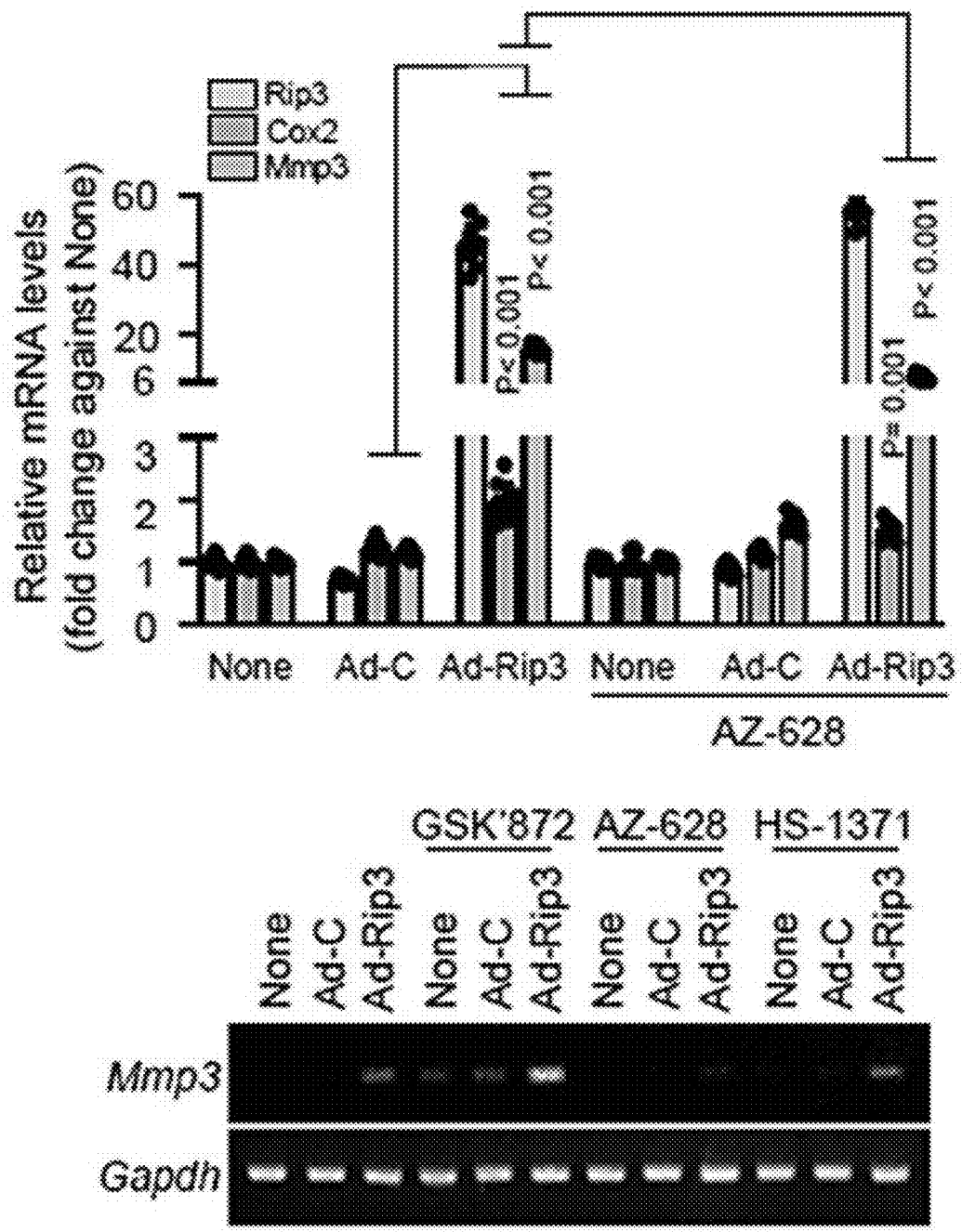
Figure 13E:
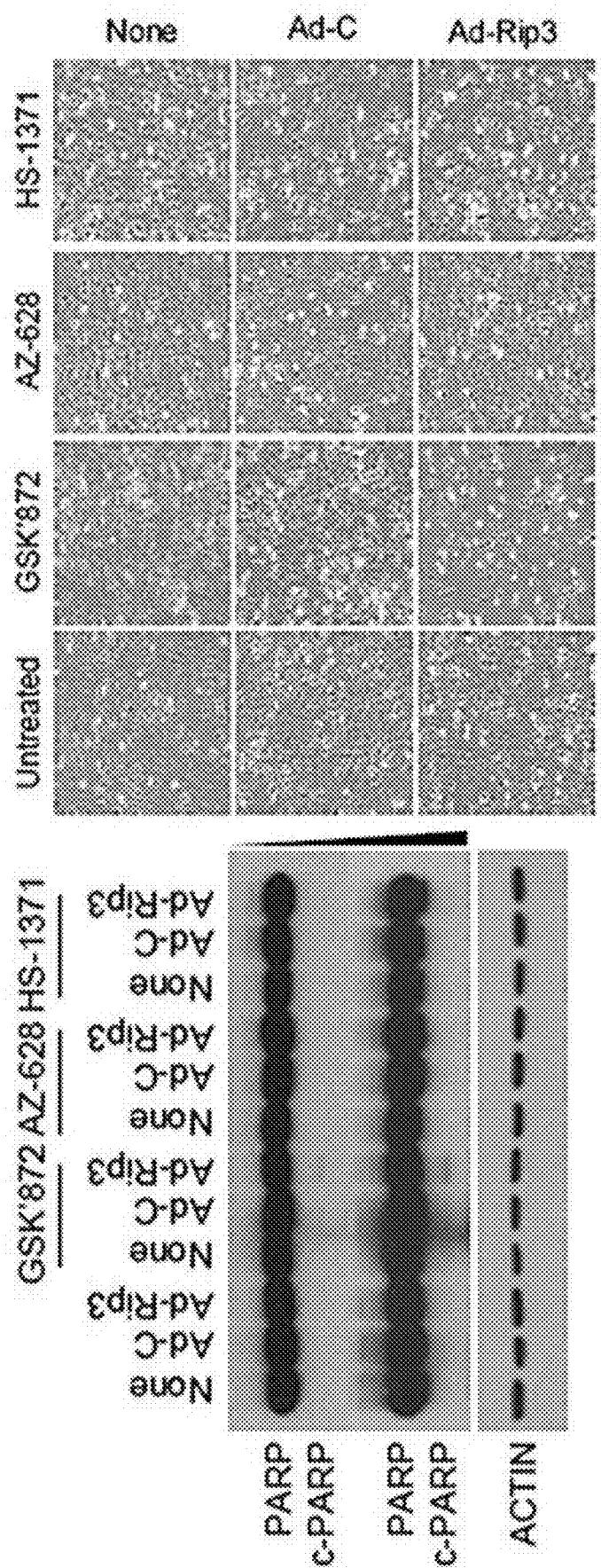

Example 6. Suppression of RIP3 Activity by RIP3 Kinase Inhibition in Osteoarthritis Pathogenesis Previously known RIP3 kinase inhibitors have type I (DAB and GSK 843), II (sorafenib, GSK 067 and HS-1371), III, or unclassified (GSK 872, GSK 840) kinase binding modes, and DAB and HS-1371 have shown therapeutic potential for RIP3-mediated inflammatory diseases. In order to investigate the ability thereof to regulate RIP3, the in vitro binding affinities of DAB, GSK 872, HS-1371 and AZ-628 were investigated (FIGS. 13A and 13B), and the effects thereof on RIP3-overexpressing chondrocytes were examined. All four compounds almost completely inhibited RIP3 phosphorylation (FIG. 11D and FIG. 13C), but Mmp3 and Cox2 expression only decreased in AZ-628-treated chondrocytes (FIG. 11E and FIG. 13D). GSK 872 and HS-1371 exhibited greater cytotoxic effects on chondrocytes than AZ-628 (FIG. 11F and FIG. 13E), indicating that binding thereof could induce conformational changes in RIP3 and chondrocyte apoptosis (FIG. 13E).

Figure 11G:
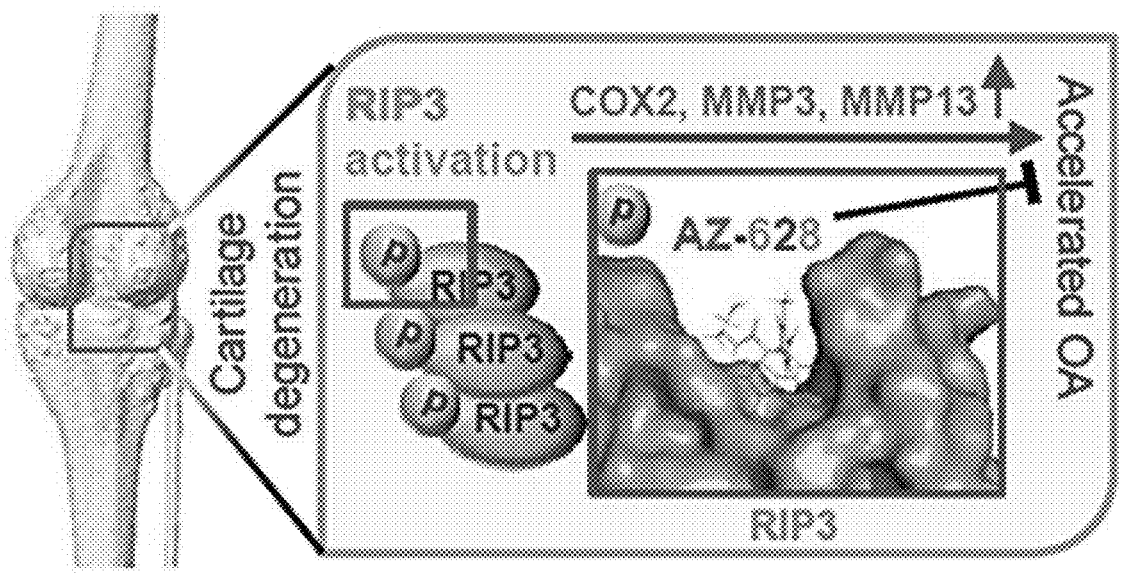
Figure 13F:
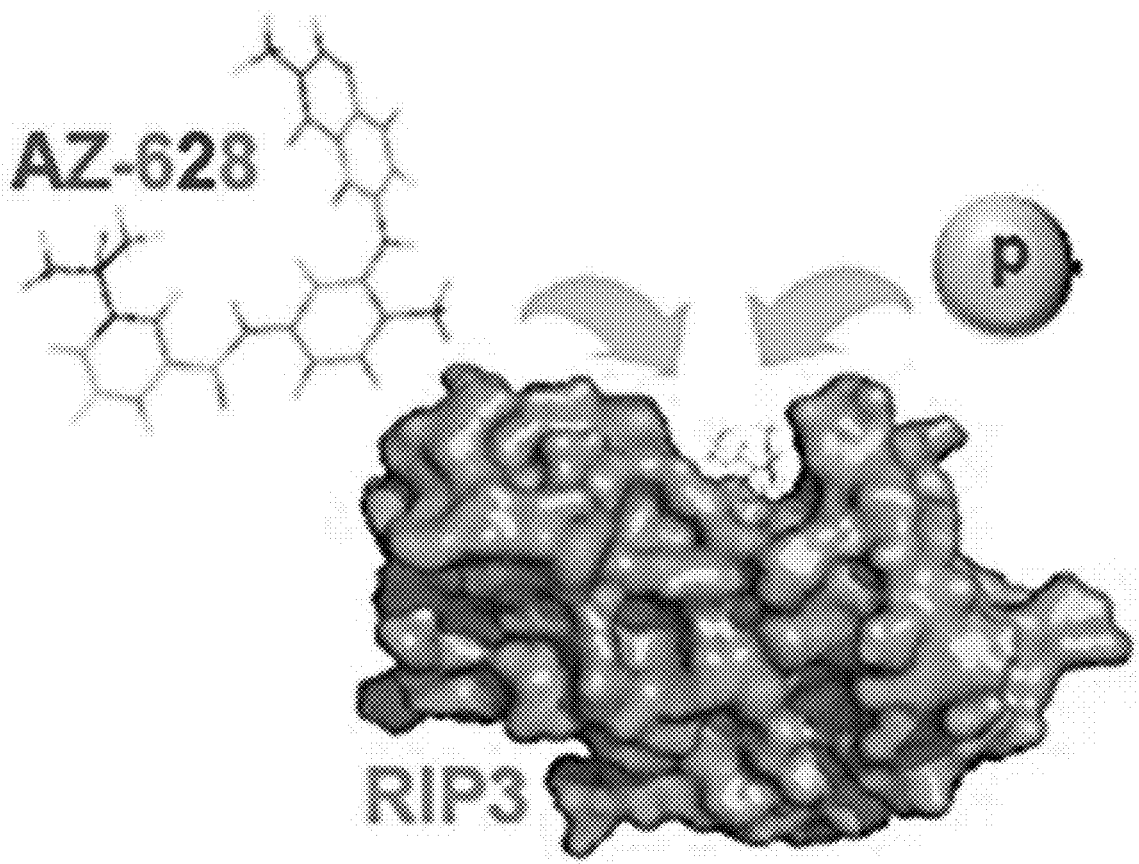

Collectively, these data suggest that AZ-628 is a potent RIP3 kinase inhibitor capable of blocking RIP3-mediated osteoarthritis pathogenesis. TRIM24-RIP3 axis perturbation accelerated osteoarthritis pathogenesis by altering gene expression, rather than RIP3-mediated necroptotic cell death in chondrocytes, while RIP3 kinase activity inhibition by AZ-628 attenuated osteoarthritis-related gene expression without chondrocyte toxicity. Therefore, the involvement of RIP3 kinase activity in cartilage pathophysiology suggests that a material that modulates RIP3 expression and activity is capable of being used as an effective therapeutic agent for osteoarthritis (FIG. 11G and FIG. 13F).

Example 7. Genetic Information

The genetic information used in the present invention is as follows.
  mouse RIPK3: UniGene ID Mm.46612
  mouse Trim24 shRNA: UniGene ID Mm.41063

INDUSTRIAL APPLICABILITY

In the present invention, it was first identified that TRIM24 and RIP3 are capable of being used as biomarkers for diagnosing osteoarthritis by confirming the tendency of TRIM24 expression to decrease and RIP3 expression to increase at the onset of osteoarthritis. TRIM24 enables prediction of disease progression due to gradually decreasing expression at the onset, whereas RIP3 expression is increased, which not only enables prediction of disease progression, but also suggests therapeutic potential through modulation of RIP3 activity. These two proteins are capable of confirming the change in the expression level from the onset of osteoarthritis, thus enabling early diagnosis of osteoarthritis and effectively blocking the progression of osteoarthritis at an early stage.

Although specific embodiments of the present invention have been disclosed in detail as described above, it will be obvious to those skilled in the art that the description is merely of preferable exemplary embodiments and is not to be construed as limiting the scope of the present invention. Therefore, the substantial scope of the present invention will be defined by the appended claims and equivalents thereof.

The invention claimed is:

1. A method for diagnosing osteoarthritis of a test subject, comprising:
   (a) obtaining a biosample from the test subject;
   (b) contacting the biosample of the test subject with an agent for measuring an expression or activity level of TRIM24 and an agent for measuring an expression or activity level of RIP3;
   (c) determining that the expression or activity level of TRIM24 of the biosample of the test subject is lower than that of a normal biosample and that the expression or activity level of RIP3 of the biosample of the test subject is higher than that of a normal biosample; and
   (d) diagnosing the test subject as having osteoarthritis,
   wherein the agent for measuring an expression or activity level of the RIP3 is a primer set comprising a first primer comprising the nucleotide sequence of SEQ ID NO: 17 and a second primer comprising the nucleotide sequence of SEQ ID NO: 18, and
   wherein the agent for measuring an expression or activity level of the TRIM24 is a primer set comprising a first primer comprising the nucleotide sequence of SEQ ID NO: 23 and a second primer comprising the nucleotide sequence of SEQ ID NO: 24.

2. The method according to claim 1, wherein the TRIM24 comprises the amino acid sequence of SEQ ID NO: 25.

3. The method according to claim 1, wherein the RIP3 comprises the amino acid sequence of SEQ ID NO: 26.

4. A method for diagnosing and treating osteoarthritis in a test subject, comprising steps of:
   (a) obtaining a biosample from the test subject;
   (b) contacting the biosample of the test subject with an agent for measuring an expression or activity level of RIP3 and an agent for measuring an expression or activity level of TRIM24, wherein the agent for measuring an expression or activity level of the RIP3 is a primer set comprising a first primer comprising the nucleotide sequence of SEQ ID NO: 17 and a second primer comprising the nucleotide sequence of SEQ ID NO: 18, and wherein the agent for measuring an expression or activity level of the TRIM24 is a primer set comprising a first primer comprising the nucleotide sequence of SEQ ID NO: 23 and a second primer comprising the nucleotide sequence of SEQ ID NO: 24;
   (c) determining that the expression or activity level of the RIP3 of the biosample of the test subject is higher than that of a normal biosample and that the expression or activity level of the TRIM24 of the biosample of the test subject is lower than that of a normal biosample;
   (d) diagnosing the test subject as having osteoarthritis; and
   (e) administering to the test subject a RIP3 inhibitor.

5. The method of claim 4, wherein the RIP3 inhibitor is selumetinib, neratinib, AZ-628, dabrafenib (DAB), GSK'843, sorafenib, GSK'067, HS-1371 GSK'872, GSK'840, or a combination thereof.

* * * * *

```
                        SEQUENCE LISTING

<160> NUMBER OF SEQ ID NOS: 26

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gaagacgaca tcaccatcca g                                            21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ctgtctttgt cacccacaca tg                                           22

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
catccgaaac cctgtcaact tg                                           22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gcccatcatc ttccacaata gc                                           22

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
```
atgtcgtgcg tcaagttatg g											21

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
tcagtcccat ccgtaacctt tg										22

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
cacactggta agtggggcaa ga										22

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
ggattgtgtt gtttcagggt tcg										23

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
ggtctggtgc ctggtctgat gat										23

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gtcctttcaa ggagaatggt gc										22

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
tcactgccac ccagaagac											19

<210> SEQ ID NO 12
<211> LENGTH: 19
<212> TYPE: DNA

```
<213> ORGANISM: Artificial Sequence
<220> FEATURE:
<223> OTHER INFORMATION: Primer

<400> SEQUENCE: 12
tgtaggccat gaggtccac                                                   19

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
ctgtgtgtgg ttgtgtgctc atcctac                                          27

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
ggcaaatccg gtgtataatt cacaatc                                          27

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
tgatggacct tctggtcttc tggc                                             24

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
catccacatg gttgggaagt tctg                                             24

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
atgtcgtgcg tcaagttatg g                                                21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
cataggaagt ggggctacga t                                                21
```

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
cagtgggact tcgtgtccg                                                    19

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
caagctgtgt aggtagcaca tc                                                22

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
cgaatgaaac tcatgcaaca aca                                               23

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
aggtgccgta acctgtatgt aa                                                22

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
tgtgaaggac actactgagg tt                                                22

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
gctctgatac acgtcttgca g                                                 21

<210> SEQ ID NO 25
<211> LENGTH: 1050
<212> TYPE: PRT
<213> ORGANISM: Homo sapiens

```
<400> SEQUENCE: 25

Met Glu Val Ala Val Glu Lys Ala Val Ala Ala Ala Ala Ala Ala Ser
1               5                   10                  15

Ala Ala Ala Ser Gly Gly Pro Ser Ala Ala Pro Ser Gly Glu Asn Glu
                20                  25                  30

Ala Glu Ser Arg Gln Gly Pro Asp Ser Glu Arg Gly Gly Glu Ala Ala
            35                  40                  45

Arg Leu Asn Leu Leu Asp Thr Cys Ala Val Cys His Gln Asn Ile Gln
    50                  55                  60

Ser Arg Ala Pro Lys Leu Leu Pro Cys Leu His Ser Phe Cys Gln Arg
65                  70                  75                  80

Cys Leu Pro Ala Pro Gln Arg Tyr Leu Met Leu Pro Ala Pro Met Leu
                85                  90                  95

Gly Ser Ala Glu Thr Pro Pro Val Pro Ala Pro Gly Ser Pro Val
                100                 105                 110

Ser Gly Ser Ser Pro Phe Ala Thr Gln Val Gly Val Ile Arg Cys Pro
            115                 120                 125

Val Cys Ser Gln Glu Cys Ala Glu Arg His Ile Ile Asp Asn Phe Phe
    130                 135                 140

Val Lys Asp Thr Thr Glu Val Pro Ser Ser Thr Val Glu Lys Ser Asn
145                 150                 155                 160

Gln Val Cys Thr Ser Cys Glu Asp Asn Ala Glu Ala Asn Gly Phe Cys
                165                 170                 175

Val Glu Cys Val Glu Trp Leu Cys Lys Thr Cys Ile Arg Ala His Gln
            180                 185                 190

Arg Val Lys Phe Thr Lys Asp His Thr Val Arg Gln Lys Glu Glu Val
    195                 200                 205

Ser Pro Glu Ala Val Gly Val Thr Ser Gln Arg Pro Val Phe Cys Pro
210                 215                 220

Phe His Lys Lys Glu Gln Leu Lys Leu Tyr Cys Glu Thr Cys Asp Lys
225                 230                 235                 240

Leu Thr Cys Arg Asp Cys Gln Leu Leu Glu His Lys Glu His Arg Tyr
                245                 250                 255

Gln Phe Ile Glu Glu Ala Phe Gln Asn Gln Lys Val Ile Ile Asp Thr
            260                 265                 270

Leu Ile Thr Lys Leu Met Glu Lys Thr Lys Tyr Ile Lys Phe Thr Gly
    275                 280                 285

Asn Gln Ile Gln Asn Arg Ile Ile Glu Val Asn Gln Asn Gln Lys Gln
290                 295                 300

Val Glu Gln Asp Ile Lys Val Ala Ile Phe Thr Leu Met Val Glu Ile
305                 310                 315                 320

Asn Lys Lys Gly Lys Ala Leu Leu His Gln Leu Glu Ser Leu Ala Lys
                325                 330                 335

Asp His Arg Met Lys Leu Met Gln Gln Gln Glu Val Ala Gly Leu
            340                 345                 350

Ser Lys Gln Leu Glu His Val Met His Phe Ser Lys Trp Ala Val Ser
    355                 360                 365

Ser Gly Ser Ser Thr Ala Leu Leu Tyr Ser Lys Arg Leu Ile Thr Tyr
370                 375                 380

Arg Leu Arg His Leu Leu Arg Ala Arg Cys Asp Ala Ser Pro Val Thr
385                 390                 395                 400

Asn Asn Thr Ile Gln Phe His Cys Asp Pro Ser Phe Trp Ala Gln Asn
                405                 410                 415
```

```
Ile Ile Asn Leu Gly Ser Leu Val Ile Glu Asp Lys Glu Ser Gln Pro
            420                 425                 430

Gln Met Pro Lys Gln Asn Pro Val Val Glu Gln Asn Ser Gln Pro Pro
            435                 440                 445

Ser Gly Leu Ser Ser Asn Gln Leu Ser Lys Phe Pro Thr Gln Ile Ser
            450                 455                 460

Leu Ala Gln Leu Arg Leu Gln His Met Gln Gln Val Met Ala Gln
465                 470                 475                 480

Arg Gln Gln Val Gln Arg Arg Pro Ala Pro Val Gly Leu Pro Asn Pro
                485                 490                 495

Arg Met Gln Gly Pro Ile Gln Gln Pro Ser Ile Ser His Gln Gln Pro
            500                 505                 510

Pro Pro Arg Leu Ile Asn Phe Gln Asn His Ser Pro Lys Pro Asn Gly
            515                 520                 525

Pro Val Leu Pro Pro His Pro Gln Gln Leu Arg Tyr Pro Pro Asn Gln
            530                 535                 540

Asn Ile Pro Arg Gln Ala Ile Lys Pro Asn Pro Leu Gln Met Ala Phe
545                 550                 555                 560

Leu Ala Gln Gln Ala Ile Lys Gln Trp Gln Ile Ser Ser Gly Gln Gly
                565                 570                 575

Thr Pro Ser Thr Thr Asn Ser Thr Ser Thr Pro Ser Ser Pro Thr
            580                 585                 590

Ile Thr Ser Ala Ala Gly Tyr Asp Gly Lys Ala Phe Gly Ser Pro Met
            595                 600                 605

Ile Asp Leu Ser Ser Pro Val Gly Gly Ser Tyr Asn Leu Pro Ser Leu
            610                 615                 620

Pro Asp Ile Asp Cys Ser Ser Thr Ile Met Leu Asp Asn Ile Val Arg
625                 630                 635                 640

Lys Asp Thr Asn Ile Asp His Gly Gln Pro Arg Pro Pro Ser Asn Arg
                645                 650                 655

Thr Val Gln Ser Pro Asn Ser Ser Val Pro Ser Pro Gly Leu Ala Gly
            660                 665                 670

Pro Val Thr Met Thr Ser Val His Pro Pro Ile Arg Ser Pro Ser Ala
            675                 680                 685

Ser Ser Val Gly Ser Arg Gly Ser Ser Gly Ser Ser Lys Pro Ala
            690                 695                 700

Gly Ala Asp Ser Thr His Lys Val Pro Val Val Met Leu Glu Pro Ile
705                 710                 715                 720

Arg Ile Lys Gln Glu Asn Ser Gly Pro Pro Glu Asn Tyr Asp Phe Pro
                725                 730                 735

Val Val Ile Val Lys Gln Glu Ser Asp Glu Glu Ser Arg Pro Gln Asn
            740                 745                 750

Ala Asn Tyr Pro Arg Ser Ile Leu Thr Ser Leu Leu Leu Asn Ser Ser
            755                 760                 765

Gln Ser Ser Thr Ser Glu Glu Thr Val Leu Arg Ser Asp Ala Pro Asp
            770                 775                 780

Ser Thr Gly Asp Gln Pro Gly Leu His Gln Asp Asn Ser Ser Asn Gly
785                 790                 795                 800

Lys Ser Glu Trp Leu Asp Pro Ser Gln Lys Ser Pro Leu His Val Gly
                805                 810                 815

Glu Thr Arg Lys Glu Asp Asp Pro Asn Glu Asp Trp Cys Ala Val Cys
            820                 825                 830
```

-continued

```
Gln Asn Gly Gly Glu Leu Leu Cys Cys Lys Cys Pro Lys Val Phe
            835                 840                 845

His Leu Ser Cys His Val Pro Thr Leu Thr Asn Phe Pro Ser Gly Glu
850                 855                 860

Trp Ile Cys Thr Phe Cys Arg Asp Leu Ser Lys Pro Glu Val Glu Tyr
865                 870                 875                 880

Asp Cys Asp Ala Pro Ser His Asn Ser Glu Lys Lys Thr Glu Gly
                885                 890                 895

Leu Val Lys Leu Thr Pro Ile Asp Lys Arg Lys Cys Glu Arg Leu Leu
            900                 905                 910

Leu Phe Leu Tyr Cys His Glu Met Ser Leu Ala Phe Gln Asp Pro Val
            915                 920                 925

Pro Leu Thr Val Pro Asp Tyr Tyr Lys Ile Ile Lys Asn Pro Met Asp
        930                 935                 940

Leu Ser Thr Ile Lys Lys Arg Leu Gln Glu Asp Tyr Ser Met Tyr Ser
945                 950                 955                 960

Lys Pro Glu Asp Phe Val Ala Asp Phe Arg Leu Ile Phe Gln Asn Cys
                965                 970                 975

Ala Glu Phe Asn Glu Pro Asp Ser Glu Val Ala Asn Ala Gly Ile Lys
            980                 985                 990

Leu Glu Asn Tyr Phe Glu Glu Leu  Leu Lys Asn Leu Tyr  Pro Glu Lys
            995                 1000                1005

Arg Phe  Pro Lys Pro Glu Phe  Arg Asn Glu Ser Glu  Asp Asn Lys
    1010                1015                1020

Phe Ser  Asp Asp Ser Asp Asp  Asp Phe Val Gln Pro  Arg Lys Lys
    1025                1030                1035

Arg Leu  Lys Ser Ile Glu Glu  Arg Gln Leu Leu Lys
    1040                1045                1050

<210> SEQ ID NO 26
<211> LENGTH: 518
<212> TYPE: PRT
<213> ORGANISM: Homo sapiens

<400> SEQUENCE: 26

Met Ser Cys Val Lys Leu Trp Pro Ser Gly Ala Pro Ala Pro Leu Val
1               5                   10                  15

Ser Ile Glu Glu Leu Glu Asn Gln Glu Leu Val Gly Lys Gly Gly Phe
            20                  25                  30

Gly Thr Val Phe Arg Ala Gln His Arg Lys Trp Gly Tyr Asp Val Ala
        35                  40                  45

Val Lys Ile Val Asn Ser Lys Ala Ile Ser Arg Glu Val Lys Ala Met
    50                  55                  60

Ala Ser Leu Asp Asn Glu Phe Val Leu Arg Leu Glu Gly Val Ile Glu
65                  70                  75                  80

Lys Val Asn Trp Asp Gln Asp Pro Lys Pro Ala Leu Val Thr Lys Phe
                85                  90                  95

Met Glu Asn Gly Ser Leu Ser Gly Leu Leu Gln Ser Gln Cys Pro Arg
            100                 105                 110

Pro Trp Pro Leu Leu Cys Arg Leu Leu Lys Glu Val Val Leu Gly Met
        115                 120                 125

Phe Tyr Leu His Asp Gln Asn Pro Val Leu Leu His Arg Asp Leu Lys
    130                 135                 140

Pro Ser Asn Val Leu Leu Asp Pro Glu Leu His Val Lys Leu Ala Asp
145                 150                 155                 160
```

```
Phe Gly Leu Ser Thr Phe Gln Gly Gly Ser Gln Ser Gly Thr Gly Ser
                165                 170                 175

Gly Glu Pro Gly Gly Thr Leu Gly Tyr Leu Ala Pro Glu Leu Phe Val
            180                 185                 190

Asn Val Asn Arg Lys Ala Ser Thr Ala Ser Asp Val Tyr Ser Phe Gly
        195                 200                 205

Ile Leu Met Trp Ala Val Leu Ala Gly Arg Glu Val Glu Leu Pro Thr
    210                 215                 220

Glu Pro Ser Leu Val Tyr Glu Ala Val Cys Asn Arg Gln Asn Arg Pro
225                 230                 235                 240

Ser Leu Ala Glu Leu Pro Gln Ala Gly Pro Glu Thr Pro Gly Leu Glu
            245                 250                 255

Gly Leu Lys Glu Leu Met Gln Leu Cys Trp Ser Ser Glu Pro Lys Asp
        260                 265                 270

Arg Pro Ser Phe Gln Glu Cys Leu Pro Lys Thr Asp Glu Val Phe Gln
    275                 280                 285

Met Val Glu Asn Asn Met Asn Ala Ala Val Ser Thr Val Lys Asp Phe
290                 295                 300

Leu Ser Gln Leu Arg Ser Ser Asn Arg Arg Phe Ser Ile Pro Glu Ser
305                 310                 315                 320

Gly Gln Gly Gly Thr Glu Met Asp Gly Phe Arg Arg Thr Ile Glu Asn
            325                 330                 335

Gln His Ser Arg Asn Asp Val Met Val Ser Glu Trp Leu Asn Lys Leu
        340                 345                 350

Asn Leu Glu Glu Pro Pro Ser Ser Val Pro Lys Lys Cys Pro Ser Leu
    355                 360                 365

Thr Lys Arg Ser Arg Ala Gln Glu Glu Gln Val Pro Gln Ala Trp Thr
370                 375                 380

Ala Gly Thr Ser Ser Asp Ser Met Ala Gln Pro Gln Thr Pro Glu
385                 390                 395                 400

Thr Ser Thr Phe Arg Asn Gln Met Pro Ser Pro Thr Ser Thr Gly Thr
            405                 410                 415

Pro Ser Pro Gly Pro Arg Gly Asn Gln Gly Ala Glu Arg Gln Gly Met
        420                 425                 430

Asn Trp Ser Cys Arg Thr Pro Glu Pro Asn Pro Val Thr Gly Arg Pro
    435                 440                 445

Leu Val Asn Ile Tyr Asn Cys Ser Gly Val Gln Val Gly Asp Asn Asn
    450                 455                 460

Tyr Leu Thr Met Gln Gln Thr Thr Ala Leu Pro Thr Trp Gly Leu Ala
465                 470                 475                 480

Pro Ser Gly Lys Gly Arg Gly Leu Gln His Pro Pro Val Gly Ser
            485                 490                 495

Gln Glu Gly Pro Lys Asp Pro Glu Ala Trp Ser Arg Pro Gln Gly Trp
        500                 505                 510

Tyr Asn His Ser Gly Lys
    515
```